US012697047B2

(12) United States Patent
Getman

(10) Patent No.: US 12,697,047 B2
(45) Date of Patent: Aug. 4, 2026

(54) SYSTEM FOR DETERMINATION AND CHANGE OF PHYSIOLOGICAL RESPONSE AND EMOTIONAL STATE

(71) Applicant: Anya L. Getman, Sandy, OR (US)

(72) Inventor: Anya L. Getman, Sandy, OR (US)

(73) Assignee: Anya L. Getman, Sandy, OR (US)

( * ) Notice: Subject to any disclaimer, the term of this patent is extended or adjusted under 35 U.S.C. 154(b) by 207 days.

(21) Appl. No.: 18/634,310

(22) Filed: Apr. 12, 2024

(65) Prior Publication Data

US 2024/0252060 A1      Aug. 1, 2024

Related U.S. Application Data

(63) Continuation-in-part of application No. 16/836,704, filed on Mar. 31, 2020, now abandoned.
(Continued)

(51) Int. Cl.
*A61B 5/00*          (2006.01)
*A61B 5/01*          (2006.01)
(Continued)

(52) U.S. Cl.
CPC .......... *A61B 5/1101* (2013.01); *A61B 5/0022* (2013.01); *A61B 5/0077* (2013.01); (Continued)

(58) Field of Classification Search
CPC ..... A61B 5/1101; A61B 5/0077; A61B 5/165; A61B 5/6887; A61B 2560/0462
See application file for complete search history.

(56) References Cited

U.S. PATENT DOCUMENTS

| | | | |
|---|---|---|---|
| 5,219,346 A | 6/1993 | Wagnieres et al. | |
| 5,334,181 A | 8/1994 | Rubinsky et al. | |
(Continued)

FOREIGN PATENT DOCUMENTS

| | | |
|---|---|---|
| AU | 2012332233 A1 | 5/2014 |
| CN | 101386814 A | 3/2009 |
(Continued)

OTHER PUBLICATIONS

Hoy et al. article titled "Miniaturized probe for femtosecond laser microsurgery and two-photon imaging", Hoy et al, {Jul. 26, 2011), retrieved Sep. 26, 2021 from hllps://www.ncbi.nlm.nih.gov/pmc/articles/PMC3143712/ (8 pages).
(Continued)

*Primary Examiner* — Unsu Jung
*Assistant Examiner* — James Moss
(74) *Attorney, Agent, or Firm* — Aurora Consulting LLC; Albert Du; Ashley Sloat

(57)          ABSTRACT

The techniques described herein relate to a system including: a housing including a gripping area and an exterior wall portion; a receptacle coupled to the housing, or at least partially defined by the housing; a sensor array, including a camera and an accelerometer, wherein the camera is located in an interior of the housing facing toward the exterior wall portion; and a communication nexus in communication with the sensor array including a processor coupled to memory. The processor can detect a tremor in a person using information from the camera and the accelerometer when the person holds the housing by the gripping area. The exterior wall portion can include a material that is opaque or reflective when viewed from the exterior of the housing but is translucent or transparent when viewed from the interior of the housing.

20 Claims, 23 Drawing Sheets

Related U.S. Application Data

(60) Provisional application No. 62/827,195, filed on Apr. 1, 2019, provisional application No. 62/827,193, filed on Apr. 1, 2019.

(51) Int. Cl.

| | |
|---|---|
| *A61B 5/0255* | (2006.01) |
| *A61B 5/11* | (2006.01) |
| *A61B 5/16* | (2006.01) |
| *A61B 5/22* | (2006.01) |
| *G16H 50/20* | (2018.01) |
| *A61B 5/0205* | (2006.01) |
| *A61B 5/0531* | (2021.01) |
| *A61B 5/145* | (2006.01) |

(52) U.S. Cl.
CPC .............. *A61B 5/01* (2013.01); *A61B 5/0255* (2013.01); *A61B 5/1123* (2013.01); *A61B 5/163* (2017.08); *A61B 5/165* (2013.01); *A61B 5/225* (2013.01); *A61B 5/6887* (2013.01); *A61B 5/741* (2013.01); *A61B 5/742* (2013.01); *A61B 5/746* (2013.01); *G16H 50/20* (2018.01); *A61B 5/02055* (2013.01); *A61B 5/0531* (2013.01); *A61B 5/14542* (2013.01); *A61B 2560/0242* (2013.01); *A61B 2560/0462* (2013.01); *A61B 2562/0219* (2013.01); *A61B 2562/0247* (2013.01); *A61B 2562/0252* (2013.01); *A61B 2562/0271* (2013.01); *A61B 2562/063* (2013.01); *A61B 2562/066* (2013.01)

(56) References Cited

U.S. PATENT DOCUMENTS

| | | | |
|---|---|---|---|
| 5,618,995 A | 4/1997 | Otto et al. | |
| 5,646,709 A | 7/1997 | Carter | |
| 6,322,578 B1 | 11/2001 | Houle et al. | |
| 6,385,474 B1 | 5/2002 | Rather et al. | |
| 6,627,613 B2 | 9/2003 | Strobel | |
| 7,527,624 B2 | 5/2009 | Dubnack et al. | |
| 7,598,860 B2 | 10/2009 | Niemi | |
| 7,744,869 B2 | 6/2010 | Simon | |
| 7,851,758 B1 | 12/2010 | Scanlon et al. | |
| 7,854,511 B2 | 12/2010 | Molnar et al. | |
| 8,399,866 B2 | 3/2013 | Balakin | |
| 9,589,374 B1 | 3/2017 | Gao et al. | |
| 9,622,662 B2 | 4/2017 | Zuzak et al. | |
| 9,814,339 B2 * | 11/2017 | DiMaria-Ghalili ... | G01F 23/292 |
| 10,052,026 B1 | 8/2018 | Tran | |
| 10,321,842 B2 | 6/2019 | Garten et al. | |
| 10,376,195 B1 | 8/2019 | Reid et al. | |
| 11,678,812 B1 * | 6/2023 | Jovanov ............... | A61B 5/4875 340/573.1 |
| 2004/0088748 A1 | 5/2004 | Perry | |
| 2005/0065436 A1 | 3/2005 | Ho et al. | |
| 2012/0283605 A1 | 11/2012 | Lewis, Jr. | |
| 2012/0289869 A1 | 11/2012 | Tyler | |
| 2014/0223462 A1 | 8/2014 | Aimone et al. | |
| 2015/0164584 A1 | 6/2015 | Davalos et al. | |
| 2015/0256799 A1 | 9/2015 | Saggiomo et al. | |
| 2015/0297109 A1 | 10/2015 | Garten et al. | |
| 2015/0320363 A1 | 11/2015 | De Haan | |
| 2015/0335288 A1 | 11/2015 | Toth et al. | |
| 2016/0220850 A1 | 8/2016 | Tyler | |
| 2018/0156881 A1 | 6/2018 | Poole et al. | |
| 2018/0164390 A1 | 6/2018 | Poole et al. | |
| 2018/0168527 A1 | 6/2018 | Poole et al. | |
| 2018/0224512 A1 | 8/2018 | Poole et al. | |
| 2019/0018096 A1 | 1/2019 | Poole et al. | |
| 2019/0053760 A1 | 2/2019 | Gerald, II | |
| 2019/0178962 A1 | 6/2019 | Poole et al. | |
| 2019/0220661 A1 | 7/2019 | Wang et al. | |
| 2019/0336101 A1 | 11/2019 | Chiang et al. | |
| 2020/0365275 A1 | 11/2020 | Barnett et al. | |
| 2021/0345926 A1 * | 11/2021 | Son ........................... | G08B 3/10 |
| 2022/0142580 A1 * | 5/2022 | Chung ................... | A61B 5/165 |

FOREIGN PATENT DOCUMENTS

| | | |
|---|---|---|
| CN | 201905995 | 7/2011 |
| EP | 1133334 A1 | 9/2001 |
| WO | 8907468 A1 | 8/1989 |
| WO | 9639960 | 12/1996 |
| WO | 0163542 A1 | 8/2001 |
| WO | 2005023121 A1 | 3/2005 |
| WO | 2008054487 A2 | 5/2008 |
| WO | 2009097220 A2 | 8/2009 |
| WO | 2017079761 A1 | 5/2017 |

OTHER PUBLICATIONS

IR Wireless (infrared wireless) retrieved Sep. 14, 2021 from hllps://searchmobilecomputing.lechtargel.com/definition/IR-wireless (3 pages).

Khairi et al. article titled "Contact and non-contact ultrasonic measurement in the food industry" {Dec. 1, 2015) retrieved Sep. 14, 2021 from hllps://www.researchgate.net/publication/285546493_Contact_and_non-:contact_ultrasonic_ measurement_in _the _food _industry_ A _review, 10 pages.

Khalili et al. "Contribution of human oocyte architecture to success of in vitro maturation technology", Khalili et al, (Jan. 2013), published on Iran J Reprod Med, v.11(1), PMC3941380, retrieved Sep. 27, 2021 fromhttps://www.ncbi.nlm.nih. Jov/pmc/articles/PMC3941380/ (10 pages).

Laws-King et al. article titled "Fertilization of human oocytes by microinjection of a single spermatozoon under the zona pellucida", Andrea aws-King et al, {Oct. 1987), Fertility and Sterility (6 pages).

Lee et al. article titled "Analysis of chromosome constitution of human spermatozoa with normal and aberrant head morphologies • lier injection into mouse oocytes", Lee et al, (1996), Human Reproduction, vol. 11, No. 9 (5 pages).

Markhede et al. article titled "Extra-abdominal desmoid tumors", Markhede et al, {Jul. 8, 2009), Acta Orthopaedica Scandinavica, 57:1 (pp. 8).

Microsoft Bing "Handheld Tens Unit" retrieved Sep. 14, 2021 from https://www. bing.com!shop?q=handheld+tens+unit&qs=n&form=SHOPSB&sp=1&pq=handheld+lens+unit&sc=0-18&sk=&cvid=5E57EA01AEB3 . . . (1 page).

Microsoft Bing "Handheld ultrasound devices," retrieved Sep. 16, 2021 from https://www.bing.com/shop?q=handheld+ultrasound devices &FORM=SHOPPA&originIGUID=E018626F2D6B4C4B 98E5335F6F8F51BA (1 page).

Miotto et al. article titled "Reflecting health: smart mirrors for personalized medicine," Digital Medicine, www.nature.com/npjdigitalmed, Scripps Research Translational Institute, Received: Aug. 7, 2018, Accepted: Oct. 17, 2018, Published online: Nov. 8, 2018 (7 pages).

Mobarak et al. "Autologous mitochondrial microinjection; a strategy to improve the oocyte quality and subsequent reproductive outcome during aging", Halimeh Mobarak el. al, (2019) (15 Pages).

Muller et al. "The Use of Sarmazenil in the Treatment of a Moxidectin Intoxication in a Foal", Muller et al, (2005), J Vet ntem Med; 19, pp. 348-349 (2 pages).

Nagarkar et al. article titled "GA-based multi-objective optimization of active nonlinear quarter car suspension system" Oct. 13, 2018) retrieved Sep. 14, 2021 from https://link.springer.com/article/10.1186/s40712-018-0096-8 (20 pages).

Neuwelt MD et al. article titled "Outwitting the Blood-Brain Barrier", Neuwelt et al, {Nov. 15, 2016), Oncology Journal, vol. 30, Issue 11 (6 pages).

Ngoc, QE Gateshead article titled "Subcutaneous Self injection for anti-coagulation treatment," (Sep. 1, 2013) retrieved Sep. 14, 2021 (4 pages).

Okamura et al. article titled "Quinoline and Benzimidazole Derivatives: Candidate Probes for In Vivo Imaging of Tau Pathology in Alzheimer's Disease", Nobuyuki Okamura et al, {Nov. 23, 2005), The Journal of Neuroscience, pp. 10857-10862 (6 pages).

(56) References Cited

OTHER PUBLICATIONS

Pielemeier et al. article titled "A high-resolution lime-frequency representation for musical instrument signals" {Sep. 24, 1993) retrieved Sep. 14, J021 from https://asa.scitation.org/doi/abs/10. 1121/1.415426, 3 pages.

Pietrangelo Ann article titled "Parasitic Worms in Humans: Know the Facts," {Mar. 17, 2019) retrieved Sep. 15, 2021 from hllps://www.healthline.com/health/worms-in-humans (12 pages).

Quach Katyanna article titled "No, really. You can see through walls using drones and Wi-Fi," {Jun. 20, 2017) retrieved Sep. 14, 2021 from https://www_theregister.co.uk/2017/06/20/drones_and_wifi_see_thru_walls/ (9 pages).

Quinn et al. article titled "Effect of Purification of Bovine Serum Albumin on the Interaction of Human Semen with Mouse Ova in vitro," (1980), Biology of Reproduction 22, 134-140 (8 pages). Intentionally Left Blank.

Sawamura et al. article titled "Development of a Handpiece and Probes for a Microsurgical Ultrasonic Aspirator: Instrumentation and l\pplication", Yutaka Sawamura et al, {Dec. 1999), Neurosurgery (11 pages).

Shaham, Shai article titled "Methods in cell biology", Shai, {Jan. 2, 2006), The Online Review of C. elegans Biology [Internet]. Pasadena CA): WormBook; 2005-2018, 77 pages retrieved Sep. 27, 2021 from https:/lwww.ncbi.nlm.nih.gov/books/NBK19784/ (45 pages).

Simons, Anya L. "Robotic Trajectory Control Employing Anyanet Neural Architecture," A Thesis Submitted to the Graduate Faculty of Rensselaer Polytechnic Institute, Troy, NY, Dec. 1992 (172 pages).

Smart Tech Solutions, Learn Smart Technology, "RF exposure to Humans, and much more" {Feb. 1, 2014) retrieved Sep. 14, 2021 from hllps://wade4wireless.com/2014/02/01 /rf-exposure-to-humans-and-much-more/ (6 pages).

Sullivan, Ben article titled "So How Exactly Does a GIF Cause a Seizure?" Motherboard Tech By Vice retrieved Sep. 15, 2021 from https://l.co/X4nR7dKS4J (10 pages).

Super small 4mm 650nm 0.5mw 1mw 5mw Red dot laser module Miniature laser head retrieved Sep. 14, 2021 rom https:/lwww.civillaser.com/index.php?rnain_page=product_info&products_id=487&gclid=Cj0KCQjwsYbOBRCOARIsAHbLPhGuzYi-K6SI3EIALC1qCYI8Mp-3gCQ77-16Ty5QwW80Gf8px8w6LWgaAhK8EALw_wcB, 5 pages.

Tesarik et al. article titled "Spermatid injection into human oocytes. I. Laboratory techniques and special features of zygote :levelopment", Tesarik et al, (1996), Human Reproduction, vol. 11, No. 4, pp. 772-779 (8 pages).

The Mysteries of IP65, IP66, and IP67 Rated Enclosures Explained Feb. 19, 2014 retrieved Sep. 14, 2021 from http:/lwww.budind.com/blog/2014/02/lhe-mysteries-of-ip-raled-enclosures-explained/, 6 pages.

The use of seat effective amplitude transmissibility (SEAT) values to predict dynamic seat comfort retrieved Sep. 14, 2021 from https:/lwww .semanticscholar.org/paper/The-use--0f-seat-effective-amplilude-(SEA T)-values-Niekerk-Dielemeier/f9385950e17b583a04338be68a3b4e05db2c6b09, 3 pages.

The Worlds first portable Auto Defibrillator (Mar. 9, 2015) retrieved Sep. 15, 2021 from hllps://www.youtube.com/ , vatch?v=-Be6oEPaqCs, 3 pages.

TP-Link AC750 Wireless Portable Nano Travel Router retrieved Sep. 14, 2021 from https://www.amazon.com/TP-ink-Wireless-Portable-Travel-Router/dp/B07V2R7W11/, 9 pages.

Transducer for Hifu High Intensity Focus Ultrasound Factory Price 4mhz-gathered Piezoelectric Ceramics printed Sep. 15, 2021, 7:55 AM, hllps://www.alibaba.com/product-detail/transducer-for-HIFU-High-inlensity-focus_ 60599016748.html?src=sern_ggl&rnark=google_shopping&src (7 pages).

Traumatic bleeding stopped cold using snake venom (Jul. 18, 2021) retrieved Sep. 15, 2021 from hllps://www.:lailykos.com/slories/2021/7/17/2040356/-Traumatic-bleeding-stopped-cold-using-snake-venom-visible-light-and-somecool-chemistry, 29 pages.

Tubular photo sensor retrieved Sep. 14, 2021 from https://www.automationdirecl.com/adc/shopping/catalog/ sensors (4 pages).

U.S. Depart of Labor, OSHA article titled "Saving Sudden Cardiac Arrest Victims in the Workplace" retrieved Sep. 15, 2021, The Wayback Machine—https://web.archive.org/web/20191201171943/https://www.osha.gov/Publications/3185.htm (2 pages).

Vajta et al. article titled "Open pulled straw {OPS) vitrification: A new way to reduce cryoinjuries of bovine ova and embryos", etrieved Feb. 6, 2020 from https://onlinelibrary.wiley.com/doi/abs/10.1002/{SICI) 1098-2795{199809)51 :1<53::AID- MRD6>3.0. CO;2-V (2 pages).

Van Andel et al. article titled "The Van Andel Transparent Glass Microsurgical Cannula", Andel et al, {May 1, 1990), retrieved Sep. 27, J021 from https://www.healio.com/ophthalmology/journals/osli/1990-5-21-5/%7B413cef68-33bb-43be-85fa-99ebf55e444a% 7D/lhe-van-andel-transparent-glass-microsurgical-cannula (3 pages).

Verma et al. article titled "Clinical Management of Epileptic Seizures in a Labrador retriever Dog", retrieved Feb. 7, 2020 from www.nexusacademicpublishers.com/table_contents_detail/13/91/html (4 pages).

Wikipedia "Caenorhabditis elegans" retrieved Sep. 27, 2021 from https://en.wikipedia.org/wiki/Caenorhabditis_elegans (22 pages).

Wikipedia "Functional magnetic resonance imaging" {Sep. 13, 2021) retrieved Sep. 14, 2021 from https://en.wikipedia.org/wiki/runctional_magnetic_resonance_imaging (28 pages).

Wikipedia "Jet Injector" retrieved Sep. 14, 2021 from hllps://en.wikipedia.org/wiki/Jet_injector (8 pages).

Wikipedia "Physics of magnetic resonance imaging" retrieved Sep. 14, 2021 from https://en.wikipedia.org/wiki/Physics_of_magnetic_resonance_imaging (18 pages).

Wikipedia "R (programming language)," https://en.wikipedia.org/wiki/R_(programming_language), printed Sep. 14, 2021, 11:22 PM (18 pages).

Wikipedia article titled Implantable cardioverter-defibrillator, (Aug. 11, 2021) retrieved Sep. 14, 2021 from hllps://en.wikipedia.org/wiki/ mplanlable_cardioverter-defibrillator (9 pages).

Wikipedia Inductive charging retrieved Sep. 14, 2021 from hllps://en.wikipedia.org/wiki/Inductive_charging (14 pages).

Wikipedia Whole body vibration, (Aug. 2, 2021) retrieved Sep. 14, 2021 from https://en.wikipedia.org/wiki/Nhole_body_vibration (11 pages).

Wikipedia Wireless power transfer, (Sep. 3, 2021) retrieved Sep. 14, 2021 from hllps://en.wikipedia.org/wiki/Nireless_power_transfer (29 pages).

Wish "PDT 4 Colors LED Light Photodynamic Facial Skin Care Rejuvenation Photon Therapy Machine," printed Sep. 14, 2021, 11:59 PM (3 pages).

Wonderly, Kimberly article titled Want to Know About Insulin Jet Injectors, (Aug. 20, 2018) retrieved Sep. 14, 2021 from hllps://www.healthline.com/ health/type-2-diabetes/insulin-jet-injectors#use (10 pages).

"Ablation for Arrhythmias" retrieved Sep. 27, 2021 from hllps://www.heart.org/en/health-topics/arrhythmia/ prevention—treatment-of-arrhythmia/ablation-for-arrhythmias (5 pages).

"Clarity 40Hz Light Kit—Gamma Light Therapy" retrieved Sep. 14, 2021 from https://gammalighttherapy.corn/collections/40hz-light-devices/products/gamma-40-hz-light-therapy-kit (5 pages).

"Compatible Draeger Flow Sensor—8403735" retrieved Sep. 27, 2021 from hllps://www.cablesandsensors.com/products/compatible-draeger-flow-sensor-8403735?variant=33810255112 (5 pages).

"DJI Ronin-SC Gimbal Stabilizer" retrieved Sep. 14, 2021 from https://www.bhphotovideo.com/c/producl/1492980-REG, 5 pages.

"Horse Wormer Guide, Horse Wormers Frequently Asked Questions", retrieved Feb. 7, 2020 from https://www.horse.com/contenl/wormer/horse-wormer-guide/ (4 pages).

"How to Calculate Confidence Levels" {Nov. 9, 2020) retrieved Sep. 14, 2021 from https://sciencing.com/calculate- ::onfidence-levels-2844.hlml, 6 pages.

"Is it possible to convert a mobile phone into a sonar device" {Aug. 21, 2014) retrieved Sep. 14, 2021 from hllps://NWW.quora.com/Is-it-possible-to-convert-a-mobile-phone-into-a-sonar-device, 3 pages.

"Microsurgical Probe-Microsurgical Probe Manufacturers, Suppliers and Exporters on Alibaba.com Temperature Instruments" retrieved

(56) References Cited

OTHER PUBLICATIONS

Sep. 27, 2021 from hllps://www.alibaba.com/trade/search?fsb=y &IndexArea=product_en&Calld=&SearchText=microsurgical+ probe+ (5 pages).

"Mu-Metal—Amorphous Magnetic shielding materials" retrieved Sep. 15, 2021 from The Wayback Machine—https://web.archive. org/ web/20180815085309/hllps://hollandshielding.com/Mu-Metal-Amorphous-Magnetic-shielding-materials (1 page).

"Oocyte Development" Embryology—Sep. 28, 2021, retrieved Sep. 27, 2021 from https://embryology.med.unsw.edu.au/embryology/ index. php/Oocyte _ Development (18 pages).

"Oxymap" retrieved Sep. 15, 2021 from hllps://www.oxymap.com/ (2 pages).

"Proteus EPSRC Interdisciplinary Research Collaboration, Lighting Up the Lung, Detecting Disease," retrieved Sep. 14, 2021 from https://proteus.ac.uk/, (2 pages).

"Supercapacitor," Wikipedia printed Sep. 14, 2021, 11:47 PM, https://en.wikipedia.org/wiki/Supercapacitor (53 pages).

"Surgery for brain tumours", Cancer Research UK, retrieved Feb. 6, 2020 from https://www.cancerresearchuk.org/about-cancer/ brain-tumours/treatment/surgery/remove-brain-tumour (5 pages).

"Tumor cell expansion challenges current physics," University of Barcelona, dated Sep. 25, 2018, Science Daily (3 pages).

20 Portable Health Gadgets That Can Change Your Life {Aug. 21, 2021) retrieved Sep. 14, 2021 from https://ravelaway.me/portable-health-gadgets/, 25 pages.

2007 Schools Wikipedia Selection "Colour" retrieved Sep. 27, 2021 from hllps://www.cs.mcgill.ca/-rwesl/wikispeedia/wpcd/wp/c/Color. htm (7 pages).

3rd International Symposium Current and Future Applications of Focused Ultrasound 2012 {Oct. 14, 2012) retrieved Sep. 15, 2021 from https://www.osa.org/en-us/meetings/global_calendar/ events/ 2012/3rd_international_ symposium_current_ and _future_ app/, 2 pages.

555 Timer Oscillator Kil retrieved Sep. 14, 2021 from https://slore. synthrolek.com/555_ Timer_Oscillator_Kil, 5 pages.

5-Mode TENS Unit By Vive—Portable Muscle Stimulator for Pain Relief {Sept. 5, 2019) retrieved Sep. 15, 2021 from https:/lwww. youtube.com/walch?,=nd0TdjdEo8U, 3 pages.

A Completely New Type of Camera Can Actually See Through The Human Body {Sep. 5, 2017) retrieved Sep. 14, J021 from https:/ lwww.sciencealert.com/scientists-have-developed-a-camera-that-can-see-through-the-human-body, 5 pages.

A concerning new study links miscarriages to cellphone radiation. How worried should we be?{Feb. 15, 2018) retrieved Sep. 15, 2021 from hllps://www.vox.com/science-and-heallh/2018/2/15/17008482/ cellphones-cancer-miscarriage-heallh, 6 pages.

Amazon.com "Magnasonic LED Pocket Pico Video Projector" retrieved Sep. 14, 2021 from https://www.amazon.com/ Magnasonic- Rechargeable-Hi-Resolution-Presentations-PP60/dp/ B016N98GG6 (11 pages).

Amazon.com "Philips HeartStart Home AED Defibrillator Value Package with Slim Carry Case, Adult AED Training Pads Cartiridge, AED Wall Mount and American Red Cross Deluxe Personal Safety Emergency Pack," retrieved Sep. 14, 2021 from https://www.amazon. com/HeartStart-861284-Philips-Home-Defibrillator/dp/ B00064CED6 (9 pages).

American Conference on Human Vibration, Information Circular 9513, Proceedings of the Second American Conference on Human Vibration, Chicago, IL, Jun. 4-6, 2008, retrieved Sep. 14, 2021 (147 pages).

Ascariasis {Dec. 22, 2020) retrieved Sep. 15, 2021 from hllps:// www.mayoclinic.org/diseases-conditions/ascariasis/ , ymptoms-causes/syc—20369593, 6 pages.

Belykh et al. article titled "Intraoperative Fluorescence Imaging for Personalized Brain Tumor Resection", Belykh et al, {Oct. 17, 2016) (27 pages).

Can music help someone with Alzheimer's?{Apr. 6, 2021) retrieved Sep. 14, 2021 from https://www.mayoclinic.org/ :liseases-conditions/ alzheimers-disease/expert-answers/music-and-alzheimers/faq-20058173, 3 pages.

Capacitive coupling {Jun. 17, 2021) retrieved Sep. 14, 2021 from hllps://en.wikipedia.org/wiki/Capacitive_coupling, 3 pages.

Car Proximity Wireless parking sensor system retrieved Sep. 15, 2021 from hllps://www.alibaba.com/product-detail/Car-Proximily-Wireless-Parking-Aid-Sensors_60782468582.html?spm=a2700. galleryofferlisl.0.0.e6ca7fdcxm9QL6, 6 pages.

Chiang et al. article titled "Resonance mode and sound pressure produced by circular diaphragms of electrostatic and piezoelectric speakers", Chiang et al, {Jan. 1, 2018), Applied Acoustics, vol. 129, pp. 365-378, retrieved Sep. 26, 2021 from hllps://www.sciencedirecl. com/science/article/abs/pii/S0003682X17302712 (2 pages).

Clarius Portable Ultrasound Review—The Medical Futurist {Sep. 27, 2018) retrieved Sep. 15, 2021 from https://www.youtube.com/ watch? ,=ZHKXyG_CBxE, 3 pages.

Cold Laser Therapy Pen retrieved Sep. 14, 2021, 11:58 PM, The LTP-50 Cold Laser Therapy Pen features a 100 mw 660nm AC powered cold laser, 5 pages.

Correia, Lino R. et al. article titled "Ultrasonic detection of bone fragent in mechanically deboned chicken breasts," Jan. 2008, Innovative Food Science & Emerging Technologies, https://www. researchgate.net/publication222428475_Ultrasonic_detection_of_ bone_fragment_in_mechanically_deboned_chicken_breasts (7 pages).

Couser et al. article titled "Retinal Oximetry," {Jul. 13, 2021) retrieved Sep. 15, 2021 from https://eyewiki.aao.org/Retinal_ Oximetry (4 pages).

Cumeras I Khan, Josep article titled "Building a Smart Mirror," U Science Tech Facultatde Ciencies I Tecnologia UVIC-UCC (47 pages), Jun. 2016.

Da Vinci Surgical System {Aug. 15, 2021) retrieved Sep. 14, 2021 from hllps://en.wikipedia. org/wiki/ Da_Vinci_Surgical_System, 4 pages.

Dahlia, John article titled "Historic breakthrough: WVU Rockefeller Neuroscience team first to use ultrasound to treat Alzheimers" (Oct. 29, 2018) retrieved Sep. 15, J021 from https://www.wvnews. com/statejoumal/news/historic-breakthrough-wvu-rockefeller-neuroscience-team-first-to-use-ultrasound/article (5 pages).

Doctors identify brain abnormalities in U.S. Embassy victims from Cuba attack {Dec. 6, 2017) retrieved Sep. 15, 2021 rom https:// www.nbcnews.com/news/us-news/doctors-identify-brain-abnormalities-u-s-embassy-victims-cuba-attack-n826996, 7 pages.

Eaton, Kit article titled Ultrasound Scans of Your Baby Now Available Via Smartphone, (Feb. 8, 2011) retrieved Sep. 14, 2021 from hllps:// NWW.fastcompany.com/1725155/ultrasound-scans-your-baby-now-available-smartphone (4 pages).

Ebay "Omnicoffeelid Premium Omnieye Coffee Lid Camera—16gb MicroSD" retrieved Sep. 14, 2021, https://www.ebay.corn/ p!23005320855?_ trkpanns=aid%3D333200%26algo%3DCOMP. MBE%26a0%3D 1%26asc% 3D20170706093515%26meid . . . (2 pages).

Einarsdottir et al. "Retinal Oximetry Imaging in Alzheimer's Disease" retrieved Sep. 15, 2021 from hllps://pubmed.ncbi.nlm.nih. Jov/26444785/ (2 pages).

Fdit Mini USB Washing Machine Ultrasound Turbine Portable for Travel Household Cloth Cleaning retrieved Sep. 14, J021 from https://www.amazon.com/Fdit-Ultrasound-Portable-Household-Cleaning/dp/B07Q8GN6W8/, 7 pages.

Filho et al. article titled "Gamma Probe-Assisted Brain Tumor Microsurgical Resection", Osvaldo et al, (2002) 6 pages.

Fok et al. article titled "Toxocara canis infection in the paratenic host", {Jan. 31, 1998), Veterinary Parasitology, vol. 74, Issues J-4 retrieved Feb. 7, 2020 from hllps://www.sciencedirecl.com/science/ article/abs/pii/S0304401797000861 (2 pages).

Gartenberg, Chaim article titled "Building your own smart mirror is surprisingly easy Take that, Snow White," The Verge, Aug. 17, 2017, 7:05 AM PDT (8 pages).

Greenwood, Veronique article titled What Does Cancer Smell Like, (Nov. 19, 2013) retrieved Sep. 15, 2021 from https://www.nytimes. com/2013/11/24/ magazine/what-does-cancer-smell-like.html (1 page).

(56)　　　　　　References Cited

OTHER PUBLICATIONS

Hamblen article titled "Draganfly to deploy drones to detect cough-
ing, signs of infection" {Mar. 26, 2020) retrieved Sep. 15, 2021
from https:/ NWW.fierceelectronics.com/electronics/draganfly-to-
deploy-drones-to-detect-coughing-signs-infection, 4 pages.
YouTube "New wonder diagnosis handheld medical scanner 800
times more sensitive than full measure scanners" {Dec. 19, 2017)
retrieved Sep. 15, 2021 from https://www.youtube.com/watch?v=
TdyK0ko6igU (3 pages).
YouTube "Researchers Use WiFi To See Through Walls," (Dec. 22,
2015) retrieved Sep. 14, 2021 from https:/lwww.youtube.com/watch?
v=fGZzNZnYIHo (3 pages).
YouTube How to Make Piezoelectric Crystal Speaker, (Sep. 8,
2012) retrieved Sep. 15, 2021 from hllps://www.youtube.com (4
pages).
YouTube How to Move Things with Sound/Acoustic Propulsion
(Mar. 15, 2014) retrieved Sep. 15, 2021 from hllps://www.youtube.
com/watch (5 pages).

* cited by examiner

| Category | Environment | Sensor type | Physiological response |
|---|---|---|---|
| Temperature | Ambient | Resistive temperature device (RTD) or thermistor | Body temperature |
| Audio | Ambient | Microphone(s) | Vocal sounds |
| Electrical | Electrostatic | Static Field Strength | Skin conductivity Electrical signals |
| Pressure | Air Ambient | Pressure sensor | Heart rate |
| Humidity | Ambient | Humidity Sensor | Body Sweat |
| Vibration | Ambient | Piezo Microphone(s) | Anatomical information Loose tooth |
| Motion | Device being held | Accelerometer Gyroscope Camera(s) | Tremors Moving/swaying to music |
| Optical | Ambient Light Intensity or Imaging (visible or IR) | Photo Resistor Camera Reitnal Oximeter | Blood oxygen |
| Optical | Ambient Light Color (visible or IR) | Photometric Sensor | Temperature map Facial expressions Crying Laughter Tremors |

FIG. 16C

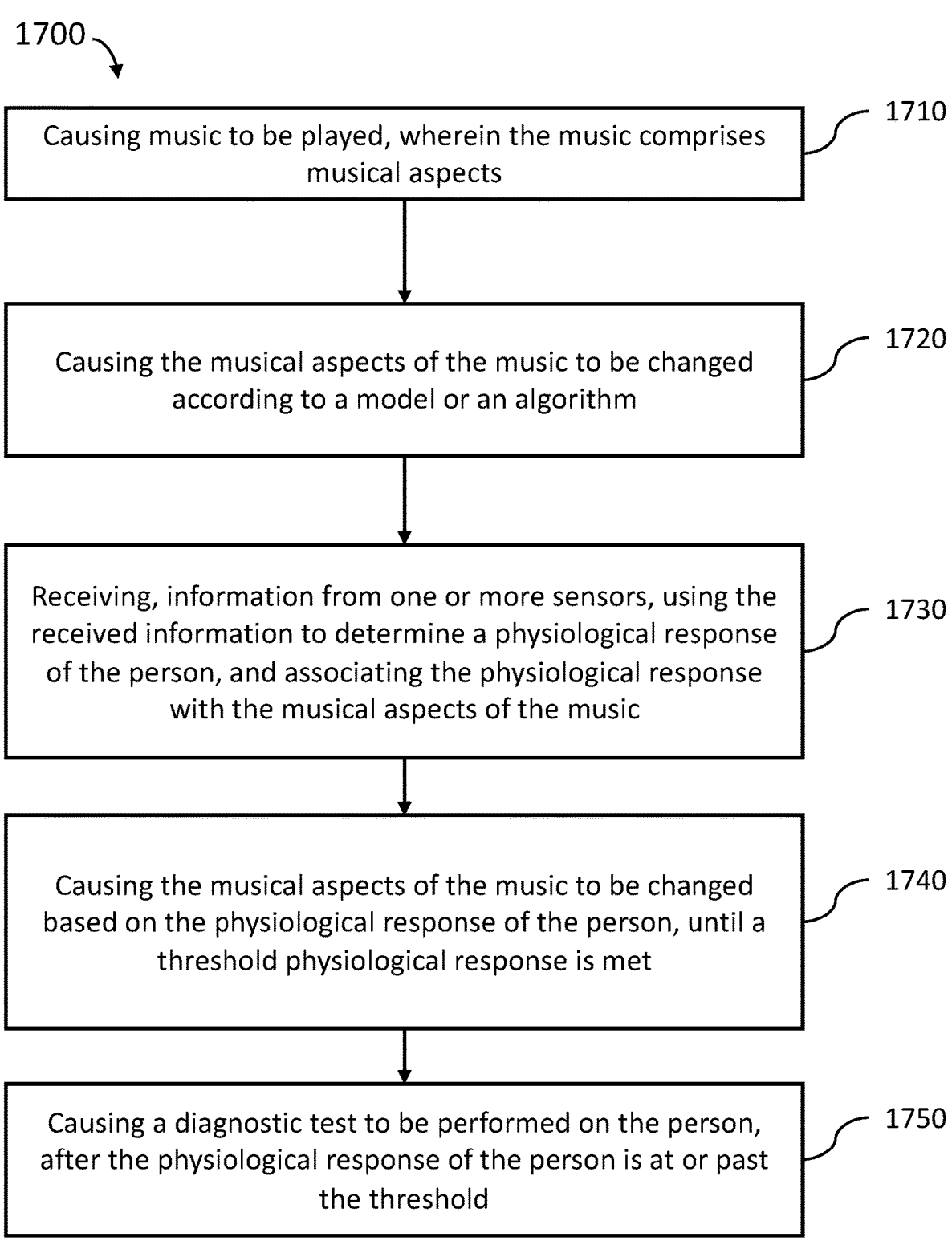

1700

1710 — Causing music to be played, wherein the music comprises musical aspects

1720 — Causing the musical aspects of the music to be changed according to a model or an algorithm 1730 — Receiving, information from one or more sensors, using the received information to determine a physiological response of the person, and associating the physiological response with the musical aspects of the music 1740 — Causing the musical aspects of the music to be changed based on the physiological response of the person, until a threshold physiological response is met 1750 — Causing a diagnostic test to be performed on the person, after the physiological response of the person is at or past the threshold

FIG. 17

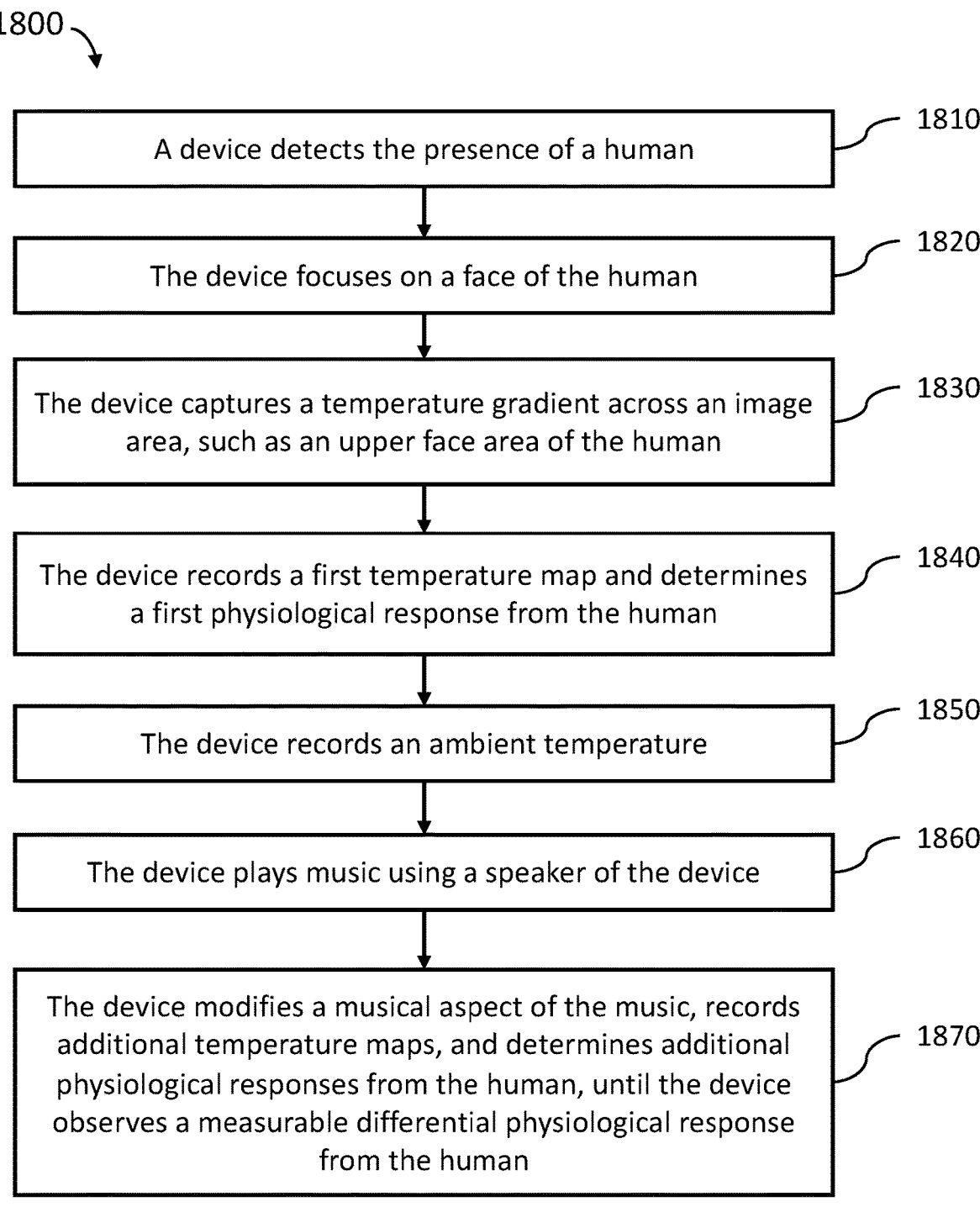

1800

A device detects the presence of a human — 1810

The device focuses on a face of the human — 1820

The device captures a temperature gradient across an image area, such as an upper face area of the human — 1830

The device records a first temperature map and determines a first physiological response from the human — 1840

The device records an ambient temperature — 1850

The device plays music using a speaker of the device — 1860

The device modifies a musical aspect of the music, records additional temperature maps, and determines additional physiological responses from the human, until the device observes a measurable differential physiological response from the human — 1870

FIG. 18

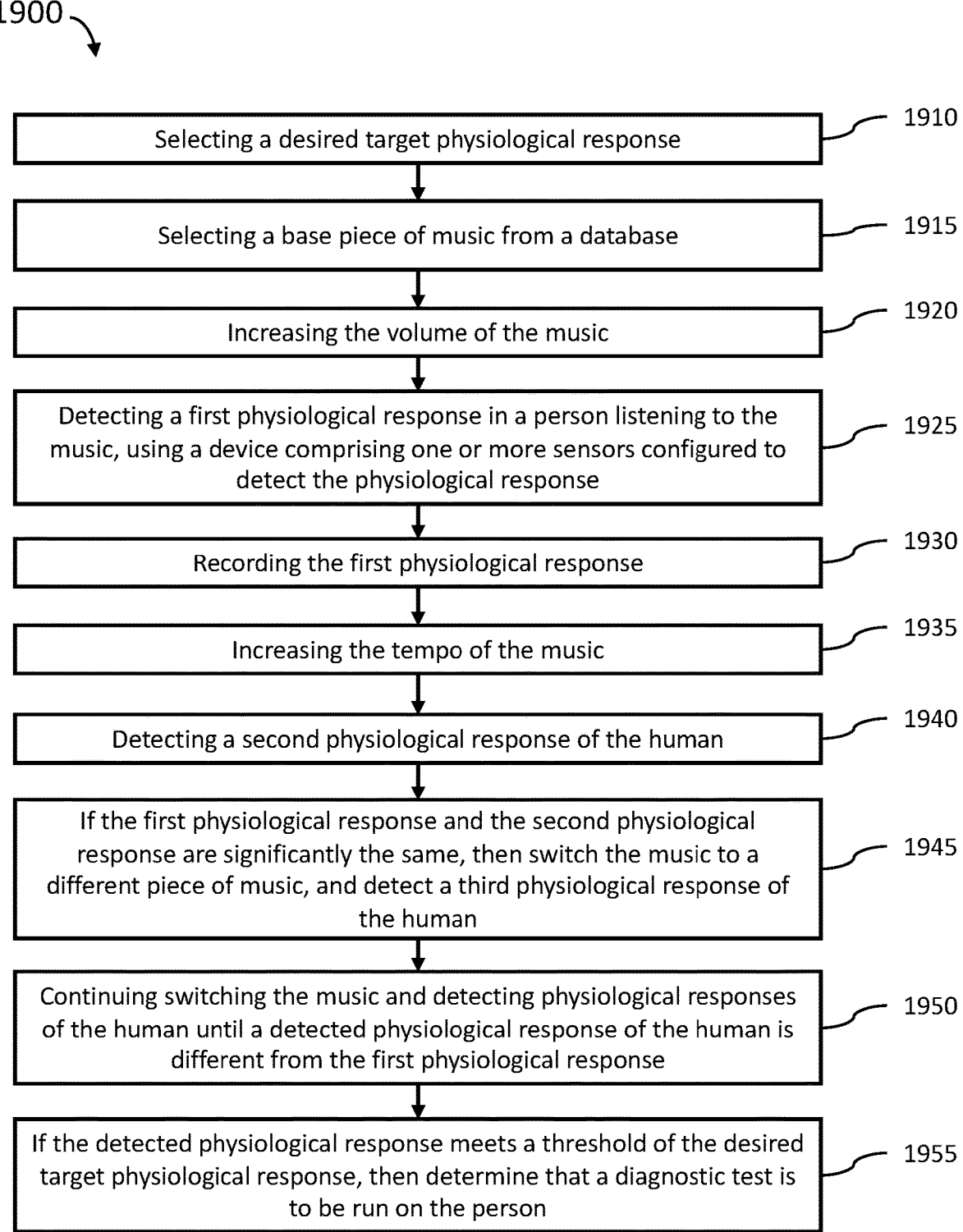

1900

Selecting a desired target physiological response — 1910

Selecting a base piece of music from a database — 1915

Increasing the volume of the music — 1920

Detecting a first physiological response in a person listening to the music, using a device comprising one or more sensors configured to detect the physiological response — 1925

Recording the first physiological response — 1930

Increasing the tempo of the music — 1935

Detecting a second physiological response of the human — 1940

If the first physiological response and the second physiological response are significantly the same, then switch the music to a different piece of music, and detect a third physiological response of the human — 1945

Continuing switching the music and detecting physiological responses of the human until a detected physiological response of the human is different from the first physiological response — 1950

If the detected physiological response meets a threshold of the desired target physiological response, then determine that a diagnostic test is to be run on the person — 1955

FIG. 19

SYSTEM FOR DETERMINATION AND CHANGE OF PHYSIOLOGICAL RESPONSE AND EMOTIONAL STATE

CROSS-REFERENCE TO RELATED APPLICATIONS

This application is a continuation-in-part of U.S. application Ser. No. 16/836,704, which was filed on Mar. 31, 2020, which claims the priority benefit of U.S. Provisional Application No. 62/827,193, which was filed on Apr. 1, 2019; and U.S. Provisional Application No. 62/827,195, which was filed on Apr. 1, 2019, the contents of each of which are hereby incorporated by reference in their entireties.

TECHNICAL FIELD

The field of this disclosure relates generally to portable medical assessment devices and, in particular, to a portable assessment device that can be used for medical diagnosis and optionally also as an actuator (dual use for the active sensors) to treat certain conditions.

BACKGROUND

In industry, machine vision provides imaging-based automatic inspection and analysis in automatic inspection, process control, robot guidance, and other applications. While systems vary, machine vision can incorporate software and hardware products, integrated systems, actions, methods and expertise.

In one machine vision configuration, one or more cameras acquire an image. The image is then processed. A CPU, a GPU, a FPGA or a combination of these can perform the processing. Deep learning training and inference impose higher processing performance requirements. Multiple stages of processing are generally used in a sequence that ends up as a desired result. A typical sequence might start with tools such as filters which modify the image, followed by extraction of objects, then extraction of data from those objects. The data can be communicated and/or compared against target values to create and communicate "pass/fail" results.

Some machine vision image processing methods include: stitching, filtering, thresholding, pixel counting, segmentation, edge detection, color analysis, blob detection and extraction, neural net/deep learning/machine learning, pattern recognition, comparison against target values, as well as others.

While machine vision has been implemented in industry, there is an unmet need in the life sciences, for example, for detecting, processing, learning from, and displaying data about aspects of animals and human beings. This includes medical and psychological diagnosis, as well as understanding human reaction to music and other stimuli.

SUMMARY

In one embodiment, a portable detection system that detects for physiological conditions in an animal body comprises: multiple radiation emitters for emitting multiple forms of radiation toward an animal body; multiple sensors for obtaining, in response to the multiple forms of radiation, body data representative of an area of the animal body; and a communication nexus that operatively connects the emitters and sensors to a processing tool for processing the body data to identify the presence of one or more components or conditions of the animal body, wherein the processing tool comprises a trainable artificial intelligence system (AI system).

In some additional, alternative, or selectively cumulative embodiments, a method for identifying a physiological condition in an animal body comprises: employing emitting multiple forms of radiation toward an animal body; obtaining, in response to the multiple forms of radiation, body data representative of an area of the animal body; providing the body data to a processing tool to identify the presence of one or more components or conditions of the animal body, wherein the processing tool comprises a trainable AI system; and providing information concerning the component or condition.

In some additional, alternative, or selectively cumulative embodiments, a physiological detection system comprises: a scanner for monitoring a body of an animal, the scanner producing difference images of a component or condition of the body between an initial state and a post-stimulus state; processing software and/or hardware for processing the difference images to determine whether the component or condition of the body has changed to an altered state in which a difference is identified between the initial state and the post-stimulus state in response to a stimulus, the processing software and/or hardware including a trainable artificial intelligence (AI) system to learn the difference between the initial state and the altered state; and an adjustable stimulus source that is optionally directable toward the body or toward a component or condition of the body to create the post-stimulus state.

In some additional, alternative, or selectively cumulative embodiments, a detection system for detecting physiological reactions in an animal body comprises: image signal means for producing an image signal representative of an image of an area of the animal body; and processing means for processing the image signal to identify the presence of one or more components or conditions of the animal body, wherein the means for processing includes: an optional digitizing means for producing a digitized image signal whenever the image signal is not already digitized; an optional detection zone means for specifying a detection zone surrounding the one or more components or conditions of the animal body within the image and means for extracting a portion of the digitized image signal corresponding to the detection zone to produce a digitized detection zone signal; tiling means for producing a tiled detection zone pixel map from the digitized detection zone signal; a trainable artificial intelligence system (AI system) comprising input processing units, hidden processing units and output processing units wherein an output from each of the input processing units is connected to an input of each of the hidden processing units and an output from each of the hidden processing units is connected to an input of each of the output processing units and wherein the trainable AI system produces an output signal at each of the output processing units representative of one or more characteristics of one or more of the components or conditions within the portion of the detection zone; inputting means for inputting the tiled detection zone pixel map into the trainable AI system; an adjustable stimulus source that is optionally directable toward the area or the detection zone of the animal body; and an output filter for producing a presence output signal indicating that one or more characteristics of the one or more components or conditions of the animal body within the detection zone has changed by a significant amount in a predetermined manner in response to the stimulus, by performing a matched filter operation on a time series of the detection zone pixel maps, including at least one detection zone pixel map for a time period before the stimulus and at least one detection zone pixel map for a time period after the stimulus to detect whether one or more characteristics of the one or more components or conditions of the animal body has changed in response to the stimulus.

In some additional, alternative, or selectively cumulative embodiments, a method for identifying a physiological response in response to a stimulus comprises: producing an image signal representative of an image of an area of the animal body; processing the image signal to identify the presence of one or more components or conditions of the animal body, optionally producing a digitized image signal whenever the image signal is not already digitized; specifying a detection zone surrounding the one or more components or conditions of the animal body within the image and means for extracting a portion of the digitized image signal corresponding to the detection zone to produce a digitized detection zone signal; producing a tiled detection zone pixel map from the digitized detection zone signal; inputting the tiled detection zone pixel map into a trainable artificial intelligence system (AI system) comprising input processing units, hidden processing units and output processing units wherein an output from each of the input processing units is connected to an input of each of the hidden processing units and an output from each of the hidden processing units is connected to an input of each of the output processing units and wherein the trainable AI system produces an output signal at each of the output processing units representative of one or more characteristics of one or more of the components or conditions within the portion of the detection zone; providing an adjustable stimulus that is optionally directable toward the area or the detection zone of the animal body; and employing an output filter for producing a presence output signal indicating that one or more characteristics of the one or more components or conditions of the animal body within the detection zone has changed by a significant amount in a predetermined manner in response to the stimulus, by performing a matched filter operation on a time series of the detection zone pixel maps, including at least one detection zone pixel map for a time period before the stimulus and at least one detection zone pixel map for a time period after the stimulus to detect whether one or more characteristics of the one or more components or conditions of the animal body has changed in response to the stimulus.

In some additional, alternative, or selectively cumulative embodiments, a method for scanning the body of an animal to determine whether a component or condition of the body has changed between an initial state and a post-stimulus state in response to a stimulus comprises: scanning the body of the animal to collect initial images of the component or condition of the body in the initial state; providing a stimulus to the body; scanning the body of the animal to collect post-stimulus images of the component or condition of the body in the post-stimulus state; and employing a trainable AI system, which is trained to essentially correctly identify differences between multiple images of the component or difference between multiple images of the condition of the body, to determine significant differences between the initial images of the initial state and the post-stimulus state to determine whether the post-stimulus state is an altered state.

In some additional, alternative, or selectively cumulative embodiments, a system including a portable device with a detection system for detecting medical conditions or physiological reactions of a subject (such as a human) comprises a housing shaped to disguise the device as an everyday object, such as a coffee mug or musical instrument; a plurality of sensors within the device, at least one of the sensors being a camera; a wall of the device being made of a material that is opaque or reflective when viewed from the exterior but is translucent or transparent when viewed from the interior of the device looking out toward the exterior; the device being in communication with a trainable artificial intelligence system that analyses data about a subject that the sensors gather, to identify a medical condition or physiological reaction in the subject; the artificial intelligence system being adapted to transmit data relating to the medical condition or physiological reaction to the device, the device having a display screen to display data from the artificial intelligence system.

In some additional, alternative, or selectively cumulative embodiments, a system including a portable device with a detection system for detecting medical conditions or physiological reactions of a subject comprises: a housing shaped to disguise the device as an everyday object; a plurality of sensors within the housing and arranged in an array that is moveable within the housing; the system including a trainable artificial intelligence system that analyses data about a subject that the sensors gather, to identify a medical condition or physiological reaction in the subject, the artificial intelligence system configured to utilize a deep learning neural network and an image and anomaly database; the device including a display to display data from the artificial intelligence system.

In some additional, alternative, or selectively cumulative embodiments, a system including a portable device with a detection system for detecting physiological or emotional reactions of a subject comprises: a housing shaped as a musical instrument; a plurality of sensors within the housing; an audio speaker with a volume control; the system including a trainable artificial intelligence system that analyses data about a subject that the sensors gather, to identify a physiological or emotional response in the subject in reaction to sounds that the device plays; and a display affiliated with the device to display data from the artificial intelligence system.

In some additional, alternative, or selectively cumulative embodiments, an altered state is evaluated to determine existence of a change in a psychological state or emotional state.

In some additional, alternative, or selectively cumulative embodiments, the stimulus is modified to enhance or diminish the change in a psychological state or emotional state.

In some additional, alternative, or selectively cumulative embodiments, the artificial intelligence (AI) comprises one or more of a neural network, a probabilistic technique such as Bayes or Markov algorithm, a kernel method (like SVM, decision trees/random forest, Gaussians, PCA, can-cor . . . ), reinforcement learning that can have nothing to do with artificial neural networks, artificial reasoning a.k.a. "good old fashioned AI," many path-planning and intelligent control-systems methods that correspond to "classical AI" (not the same as GOFAI), alife (swarms, cellular automata . . . ), agents and chaos systems, and/or any algorithm or group of algorithms that optimize a value function (reinforcement learning and linear dynamic programming).

In some additional, alternative, or selectively cumulative embodiments, the trainable AI system is comprised of a single layer of input processing units, more than one layer of hidden processing units and a single layer of output processing units and wherein an output from each of the input processing units is connected to an input of each of the hidden processing units in a first layer of the hidden processing units, an output from each of the hidden processing units in a last layer of the hidden processing units is connected to an input of each of the output processing units, and multiple layers of the hidden processing units are interconnected such that the output from each of the hidden processing units in any one but the last of the layers of the hidden processing units is connected to the input of each of the hidden processing units in a next layer of the hidden processing units.

In some additional, alternative, or selectively cumulative embodiments, the animal body is a human body.

In some additional, alternative, or selectively cumulative embodiments, one of the one or more components or conditions of the animal body comprises an internal component.

In some additional, alternative, or selectively cumulative embodiments, one of the one or more components of the animal body comprises one or more of an internal organ or an internal system.

In some additional, alternative, or selectively cumulative embodiments, one of the one or more components of the animal body comprises one or more of a blood vessel or a nerve.

In some additional, alternative, or selectively cumulative embodiments, one of the one or more conditions of the animal body comprises one or more of heart rate, blood pressure, pupil diameter.

In some additional, alternative, or selectively cumulative embodiments, one of the one or more conditions of the animal body comprises an emotional condition.

In some additional, alternative, or selectively cumulative embodiments, one of the one or more conditions of the animal body comprises one or more of sorrow, joy, or arousal.

In some additional, alternative, or selectively cumulative embodiments, the representative body data comprises an image.

In some additional, alternative, or selectively cumulative embodiments, the representative body data comprises an infrared image.

In some additional, alternative, or selectively cumulative embodiments, the representative body data comprises a sound image.

In some additional, alternative, or selectively cumulative embodiments, the representative body data comprises an ultrasonic sound image.

In some additional, alternative, or selectively cumulative embodiments, the sensors include one or more sensors for producing a video signal representative of a video image of the one or more components or conditions of the human body.

In some additional, alternative, or selectively cumulative embodiments, the sensors include a video camera for producing an analog video signal representative of a video image.

In some additional, alternative, or selectively cumulative embodiments, the sensors comprise an infrared sensor.

In some additional, alternative, or selectively cumulative embodiments, the sensors comprise a sound sensor.

In some additional, alternative, or selectively cumulative embodiments, the sensors comprise an ultrasound sensor.

In some additional, alternative, or selectively cumulative embodiments, a stimulus is directed toward the body of the animal.

In some additional, alternative, or selectively cumulative embodiments, the stimulus is visual.

In some additional, alternative, or selectively cumulative embodiments, the stimulus is auditory.

In some additional, alternative, or selectively cumulative embodiments, in the stimulus comprises sound.

In some additional, alternative, or selectively cumulative embodiments, herein the stimulus comprises music.

In some additional, alternative, or selectively cumulative embodiments, the stimulus comprises one or more selected harmonies.

In some additional, alternative, or selectively cumulative embodiments, the stimulus comprises one or more selected chords.

In some additional, alternative, or selectively cumulative embodiments, the stimulus comprises ultrasound.

In some additional, alternative, or selectively cumulative embodiments, one or more of the radiation emitters can be applied to treat the component or the condition.

In some additional, alternative, or selectively cumulative embodiments, the component or the condition comprises Alzheimer's disease.

In some additional, alternative, or selectively cumulative embodiments, the component or the condition comprises a fibroid.

In some additional, alternative, or selectively cumulative embodiments, the radiation comprises one or more of UV light radiation, visible light radiation, infrared light radiation, microwave radiation, radio sound radiation, and ultrasonic radiation.

In some additional, alternative, or selectively cumulative embodiments, the trainable AI system is implemented in computer software as a neural network simulator running on a computer.

In some additional, alternative, or selectively cumulative embodiments, the trainable AI system is implemented in computer hardware.

In some additional, alternative, or selectively cumulative embodiments, a numerical connection weight is assigned to (i) each of the connections between each of the outputs of each of the input processing units and each of the inputs of each of the hidden processing units and (ii) each of the connections between each of the outputs of each of the hidden processing units and each of the inputs of each of the output processing units.

In some additional, alternative, or selectively cumulative embodiments, a numerical bias is assigned to each of the hidden processing units and each of the output processing units.

In some additional, alternative, or selectively cumulative embodiments, the value of each of the numerical connection weights and each of the numerical biases is determined through a closed-loop training procedure utilizing back-propagation techniques.

In some additional, alternative, or selectively cumulative embodiments, the closed-loop training procedure is the Generalized Delta Rule.

In some additional, alternative, or selectively cumulative embodiments, the stimulus causes the characteristic to respond in a desirable manner.

In some additional, alternative, or selectively cumulative embodiments, the change in the characteristic can be identified.

In some additional, alternative, or selectively cumulative embodiments, the change in the characteristic can be positively reinforced by a subsequent stimulus.

In some additional, alternative, or selectively cumulative embodiments, a subsequent stimulus can be modified to affect the change in the characteristic.

In some additional, alternative, or selectively cumulative embodiments, a subsequent stimulus can be modified to enhance the change in the characteristic.

In some additional, alternative, or selectively cumulative embodiments, the processing means includes a computer simulating the neural network.

In some additional, alternative, or selectively cumulative embodiments, a presence output or presence signal is triggered by a processing tool or a computer when an altered state is determined to exist in the component or condition.

In some additional, alternative, or selectively cumulative embodiments, the image of the area is comprised of pixels, each pixel having a value corresponding to the amount of light associated with the pixel; and wherein the computer compares the values of pixels of a most recent image of the area with the values of pixels of an earlier in time image of the area to produce a difference image comprised of pixels, each of which have a value corresponding to the difference in values between corresponding pixels of the most recent image and the earlier in time image; and wherein the AI system or neural network simulated by the computer or processing means having weights for each pixel network simulated by the computer having weights for each pixel which are multiplied by the respective pixel value of the difference image and then added together to form a sum, which if greater than a predetermined amount, results in the computer or processing means providing the presence output or presence signal.

In some additional, alternative, or selectively cumulative embodiments, the scanning system or monitoring means includes additional sensors, that together with the video camera produces the difference image of the area, the value of each of the pixels of the image having a component corresponding to the additional sensors as well as a component corresponding to the amount of light associated with the pixel.

In some additional, alternative, or selectively cumulative embodiments, additional sensors include at least a second video camera.

In some additional, alternative, or selectively cumulative embodiments, additional sensors include infrared detectors.

In some additional, alternative, or selectively cumulative embodiments, additional sensors include microwave detectors.

In some additional, alternative, or selectively cumulative embodiments, the trainable neural network uses back propagation techniques.

In some additional, alternative, or selectively cumulative embodiments, the detection system is portable.

In some additional, alternative, or selectively cumulative embodiments, the detection system is handheld.

In some additional, alternative, or selectively cumulative embodiments, the detection system is housed in a mug-shaped container.

In some additional, alternative, or selectively cumulative embodiments, where the scans are directed at an object instead of a body.

Some additional, alternative, or selectively cumulative embodiment, of the present invention relate to a system that includes a portable device that has a detection system for detecting medical conditions or physiological reactions of a human. The device has a housing shaped to disguise the device as an everyday object, such as a coffee mug or musical instrument. A plurality of sensors is located within the device, with at least one of the sensors being a camera. A wall of the device is made of a material that is opaque or reflective when viewed from the exterior, but the wall is translucent or transparent when viewed from the interior of the device looking out toward the exterior. In this way, light from outside the device can be detected by the sensors on the interior of the device, while the subject does not see the sensors on the interior of the device.

The device is in communication with a trainable artificial intelligence system that analyses data about a subject that the sensors gather. The system may identify a medical condition or physiological reaction in the subject. After processing data from the sensors, the artificial intelligence system is adapted to transmit data relating to the medical condition or physiological reaction to the device, the device having a display screen to display data from the artificial intelligence system.

Various optional features may be incorporated, either alone or in combination with other optional features, into the system. At least one sensor within the device may mounted on a gimbal to stabilize the sensor. The gimbal may rotate about one, two, or three axes, as desired. The device may include a variety of configuration, such as a first camera mounted on a gimbal, and a second camera mounted on a different, rotatable mounting.

In some additional, alternative, or selectively cumulative embodiments, the device has multiple separate housings, such as two halves. As just one example, a first half may be mounted on a table top, while the second half may be mounted on a bottom side of the table top. The first and second halves are typically in communication with one another. In one embodiment, the device is shaped as a coffee cup. The cup may have a wall that is reflective when viewed from the exterior and at least partially transparent viewed from the interior of the cup.

In some additional, alternative, or selectively cumulative embodiments, the device includes an array of cameras and/or sensors arranged in a spiral configuration within the device. As an option, a laser or other light source may be located on top of the array. In another embodiment, the device may include active sensors employed in sender/receiver pairs. In one configuration, the sensors may be mounted on a pole that a drive motor rotates. The drive motor may be operated from a control panel on the device, or alternatively remotely as from a cell phone, laptop, or other external device.

In some additional, alternative, or selectively cumulative embodiments, sensors are provided in a detachable unit that is attached onto the cup. Consequently, a portion of the cup may be available to hold a beverage for drinking and/or another purpose.

In some additional, alternative, or selectively cumulative embodiments, the device may be equipped with sensors to determine the orientation, location, velocity, acceleration, and/or other aspects of the device. In one embodiment, the device includes a gyro and an accelerometer to determine one or more orientation parameters of the cup.

In some additional, alternative, or selectively cumulative embodiments, the device may be shaped as a musical instrument. The instrument may be sound-emitting, as through a speaker that is either part of the device or is external to the device, including a BlueTooth-connected speaker, headphones, earbuds or other device that emits sound from an electronic signal. In one embodiment, the sensors gather data that may be processed to sense a physiological and/or emotional response of the subject to emitted sounds.

In some additional, alternative, or selectively cumulative embodiments, a trainable artificial intelligence system includes a deep learning neural network, an image and anomaly database, and a customer medical and image history record. Alternatively, the deep learning system may access one or more other databases or sources of information as it seeks to identify potential medical conditions and/or physiological or emotional responses of a subject.

In some additional, alternative, or selectively cumulative embodiments, the medical condition or the physiological reaction is associated with an internal organ, an internal system, a blood vessel, or a nerve, heart rate, blood pressure, pupil diameter, an emotional condition, a facial expression, tearing up, swaying, or change in position.

Some additional, alternative, or selectively cumulative embodiments of the present invention relate to a system including a portable device with a detection system for detecting medical conditions or physiological reactions of a human. The device may include a housing shaped to disguise the device as an everyday object. A plurality of sensors resides within the housing and at least some of the sensors are arranged in an array that is moveable within the housing. The system may include a trainable artificial intelligence system that analyses data about a subject that the sensors gather, to identify a medical condition or physiological reaction in the subject, the artificial intelligence system including a deep learning neural network and an image and anomaly database, and/or other databases or information useful in analyzing data from the sensors. The device may include a display to display data from the artificial intelligence system. In one embodiment, the device is shaped as a coffee mug and the screen is circular in configuration and resides in the top opening of the device.

Devices according to this embodiment may include optional features as described above. Further, the device may include other optional features, either alone or in combination with one another. One embodiment includes a device that has a motor on the interior of the device to selectively move the sensors within the housing. In another embodiment, the device includes active sensors employed in sender/receiver pairs, the sensors mounted on a pole that a drive motor rotates. The device may optionally include at least one sensor within the interior of the device is moveable by remote command.

In some additional, alternative, or selectively cumulative embodiments, the system includes multiple portable devices each having sensors on the interior thereof. The multiple devices are in communication with one another and, for example, may transmit information such as the location of the device, data from sensors, movement characteristics of the device, and other information.

In some additional, alternative, or selectively cumulative embodiments, a system according to the present invention may include a portable device with a detection system for detecting physiological and/or emotional reactions of a human. The device may have a housing shaped as a musical instrument, which may be molded, 3D printed, or constructed by other means. A plurality of sensors resides within the housing. The system also includes at least one audio speaker that has a volume control. The system includes a trainable artificial intelligence system that analyses data about a subject that the sensors gather, to identify a physiological or emotional response in the subject in reaction to sounds that the device plays. The device includes a display affiliated with the device to display data from the artificial intelligence system.

In some additional, alternative, or selectively cumulative embodiments, the sounds are a series of at least one of music, binaural beats, or a series of tones, among other possible series of sounds. In one embodiment, the sensors detect at least one of: heart rate, blood pressure, pupil diameter, facial expression, tearing up, swaying to music, change in seating position. The artificial intelligence system is adapted to identify psychological or emotional states in the subject in response to musical stimuli.

In some additional, alternative, or selectively cumulative embodiments, at least one sensor within the device is mounted on a gimbal to stabilize the sensor.

In some additional, alternative, or selectively cumulative embodiments, the device includes a first camera mounted on a gimbal and a second camera mounted so as to be rotatable.

In some additional, alternative, or selectively cumulative embodiments, the device comprises two halves, including a first half adapted to be mounted on a top side of a table top and a second half adapted to be mounted on a bottom side of the table top, the first and second halves being in communication with one another.

In some additional, alternative, or selectively cumulative embodiments, the device is shaped as a cup, having a cup wall that is reflective when viewed from the exterior and at least partially transparent when viewed from the interior of the cup to the exterior.

In some additional, alternative, or selectively cumulative embodiments, the device includes an array of cameras and/or sensors arranged in a spiral configuration within the device.

In some additional, alternative, or selectively cumulative embodiments, the laser is located on top of the array.

In some additional, alternative, or selectively cumulative embodiments, the device includes active sensors employed in sender/receiver pairs, the sensors mounted on a pole that a drive motor rotates.

In some additional, alternative, or selectively cumulative embodiments, the sensors are provided in a detachable unit that is attached onto the device, a portion of the device adapted to hold a beverage, wherein the unit includes a rechargeable battery.

In some additional, alternative, or selectively cumulative embodiments, the device includes a gyro and an accelerometer to determine one or more orientation parameters of the device.

In some additional, alternative, or selectively cumulative embodiments, the device is shaped as a musical instrument, is operable to emit sounds, and is operable to sense a physiological and/or emotional response of the subject to sounds emitted by the device.

In some additional, alternative, or selectively cumulative embodiments, the trainable artificial intelligence system utilizes a deep learning neural network, an image and anomaly database, and a medical and image history record of the subject.

Selectively cumulative embodiments are embodiments that include any combination of multiple embodiments that are not mutually exclusive.

The foregoing and other objects, features, and advantages of the invention will become more apparent from the following detailed description, which proceeds with reference to the accompanying figures.

In some embodiments, the techniques described herein relate to a system including: a housing including a gripping area and an exterior wall portion separating an interior of the housing from an exterior of the housing, wherein the exterior wall portion includes a material that is opaque or reflective when viewed from the exterior of the housing but is translucent or transparent when viewed from the interior of the housing; a receptacle coupled to the housing, or at least partially defined by the housing; a sensor array, including a camera and an accelerometer, wherein the camera is located in the interior of the housing facing toward the exterior wall portion; and a communication nexus in communication with the sensor array including a processor coupled to memory; wherein the processor is configured to detect a tremor in a person using information from the camera and the accelerometer when the person holds the housing by the gripping area.

BRIEF DESCRIPTION OF THE DRAWINGS

FIG. 16C shows a table that includes categories of measurements that can be made using the systems and methods described herein, in accordance with some embodiments.

FIG. 17 is a flowchart of an example method for a computer-implemented method for performing a diagnostic test on a person, in accordance with some embodiments.

FIG. 18 is a flowchart of an example method for determining and changing a physiological response of a person, in accordance with some embodiments.

FIG. 19 is a flowchart of an example method for determining and changing a physiological response of a person, in accordance with some embodiments.

DETAILED DESCRIPTION OF EMBODIMENTS

Example non-limiting embodiments are described below with reference to the accompanying drawings.

Figure 1:
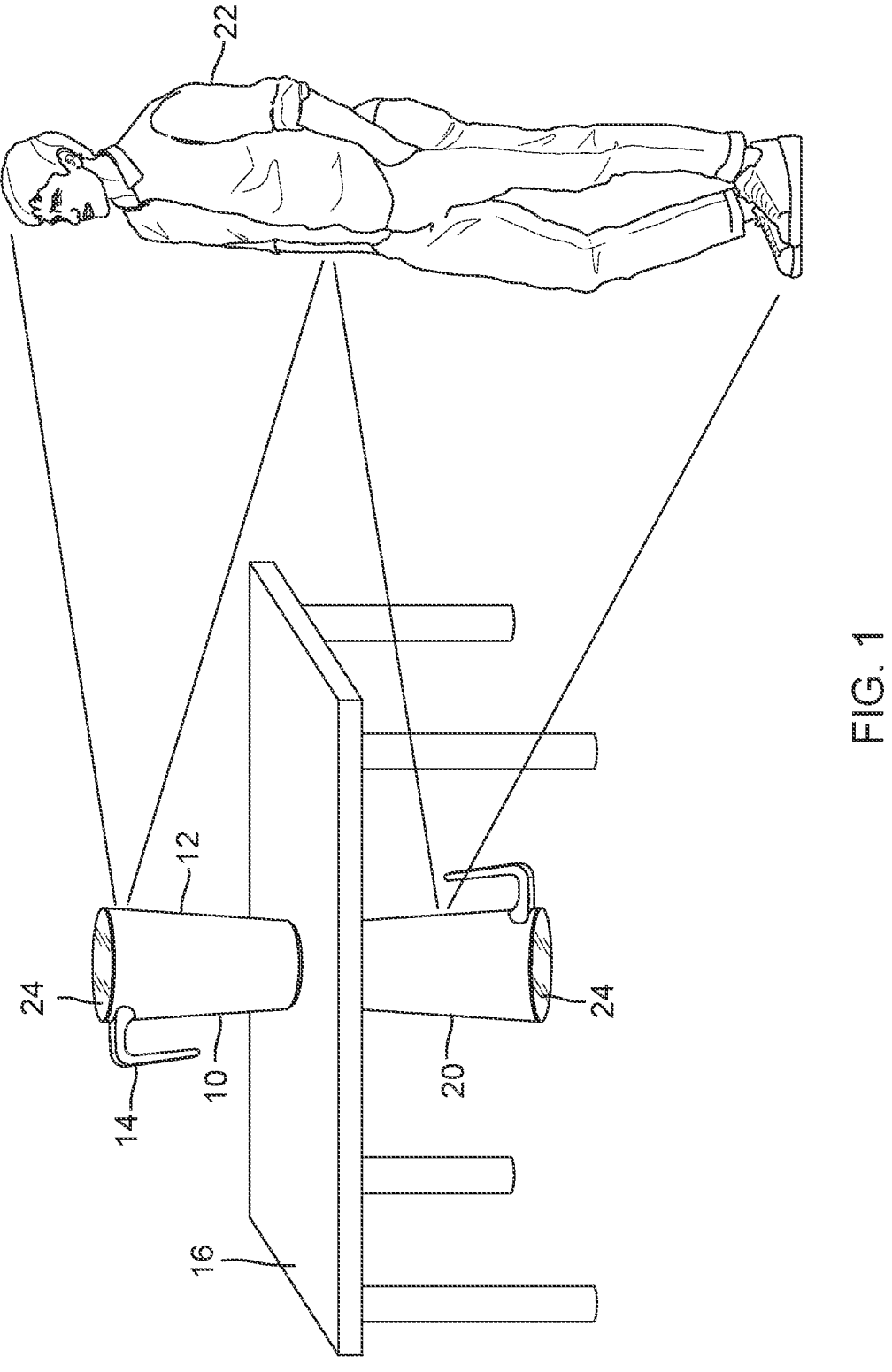
FIG. 1 illustrates an example of a portable assessment device (such as shaped like one or more mugs) used as a scanner to assess medical or threat conditions of a user.

Turning now to one non-limiting specific implementation of the invention, FIG. 1 illustrates a device 10 that may have the form and look disguises the device so that it is not readily apparent that it is a detection system. More particular, the device may have a shape appearance that looks different from a tricorder or other medical scanning device. In some embodiments, the device 10 may have the appearance of an everyday object.

An everyday object may be a household object such as an appliance, piece of equipment, drinkware, furniture, artwork, or toy, etc. Examples of an appliance include, but are not limited to, a microwave, a coffee maker, and a drink dispenser. Examples of a piece of equipment include, but are not limited to, a phone, a printer, a laptop computer, a monitor, or a speaker, etc. Examples of drinkware include, but are not limited to, a cup, a mug, a glass, or a coffee cup, etc. Examples, of furniture include, but are not limited to, a chair, a sofa, a table, a desk, or a cabinet, etc. Examples of artwork include, but are not limited to, a wall picture or a statute, etc. Examples, of toys include, but are not limited to, a robot or a stuffed animal, etc. The device 10 may act as a single device 10 or may interact with multiple devices in the same room or different room that have the same appearance or functions or have different appearances or functions. A primary device 10 may be portable. In particular, a primary device 10 may be handheld.

The interior of the device 10 may include sensors, mirrors, electronics, speakers, beepers and the like. The sensors may include one or more of scanning sensors or self-relational sensors. Scanning sensors may include, but are not limited to, image sensors (like a camera), auditory sensors (like a microphone), ultrasonic sensors, infrared sensors, etc. In some embodiments that include two or more sensors of the same category, the sensors may be identical or have different makes or ranges of operation. Image sensors may, for example, have different optical arrangements such as different focal arrangements and fields of view. Self-relational sensors may include, but are not limited to, accelerometers, gyroscopes, and GPS. The sensors may be packaged so that they are modular, so that they can be interchangeably connected to the device 10. One will appreciate that certain sensors may perform better in particular locations or orientations. In such circumstances, particular categories of sensors may be shaped differently to accommodate particular positioning.

The device may also include one or more stimuli emitters. The stimuli emitters may include radiation emitters including, but not limited to, sound, light, or temperature emitters. Sound emitters may include, but are not limited to, auditory sound, ultrasound, low frequency sound, and high-frequency sound emitters. Light emitters may include, but not limited to, UV emitters, visible light emitters, and IR emitters. The light emitters may be lasers or LEDs. The emitters may be packaged so that they are modular, so that they can be interchangeably connected to the device 10. These various sensors and emitters and their controllers are commercially available in miniature sizes and may all be readily packaged into a device 10 as large as a cup, for example.

The walls 12 of the coffee mug may be made from a transparent material such as glass or a clear polymer, so that a camera may see through the walls 12 and/or a laser beam may pass through the walls 12. Alternatively, the exterior of the walls 12 may include a reflective film that reflects some exterior light but allows considerable light to pass through the walls 12 so as to reach a camera on the interior of the cup, and/or to permit a laser beam to pass through.

The device 10 may have an optional handle 14. The handle 14 may serve as an antenna, may have USB and/or other ports on it, or may serve other purposes, including simply as a handle 14. The bottom of the device 10 may optionally include a magnetized material, such that the device may be mounted to a surface, such as a metallic table surface 16. The bottom may alternatively include another means for securing the device 10, such as one or more suction cups, adhesive, or other securing approaches known in the art. In some embodiments, the bottom of the device 10 may have USB and/or other ports on it, or may be connected to a power supply.

The device 10 may include a communication nexus that includes one or more communication nodes to operatively connect the emitters and sensors, independently or collectively, to a processing tool that may employ a trainable AI system as described herein. Moreover, the processing tool is presented herein by way of example to a trainable AI system; however, one will appreciate that a more generic processing tool may be substituted for the AI system mentioned anywhere within this description.

The communication nexus may include communication nodes that connect each emitter independently to individual or separate controllers and/or to the processing tool. Similarly, the communication nexus may include nodes that connect each sensor independently to individual or separate controllers and/or to the processing tool. The communication nexus may alternatively or additionally include a communication node that collectively connects multiple emitters and/or sensors to the controllers and/or to the processing tool. Moreover, communication nexus may include one or more communication nodes that connect the emitters to the sensors, emitters to each other, and/or sensors to each other. The connections may convey data or instructions in a single direction or in both directions.

The communication nexus may utilize or connect to a local network via Wi-Fi, Bluetooth, Ethernet cable, or other method for communicating with a network. The device 10 may have one or more ports, such as for USB, flash drive, cables, and/or other accessories. A presently preferred power source is one or more lithium-ion batteries, preferably located on the interior of the device 10 in a manner a user may access the batteries for replacement. Lithium-ion batteries may be sized to fit into small, irregular spaces. They can also be swapped out and fast charged as needed. The batteries may be rechargeable, such as by a DC power adapter, a USB power source, wirelessly on a recharging pad similar to how many mobile phones are now charged, or other battery charging methods known in the art. It is noted that the wireless recharging pad may have a look and shape of a drink coaster.

In one embodiment, the device 10 includes multiple housings, such as two halves. One half may rest atop the surface, while the other half 20 may rest below the surface. The device 10 is positioned such that a user 22 sitting or standing adjacent to the surface (e.g. a user sitting on a dining room chair) can be scanned by the device 10 with minimal disruption. The lid on one or both halves may include a display screen 24, on which a user 22 or operator may view the body scan.

In another embodiment, the multiple housings may include housings positioned at one more additional locations in a room. These locations may be selected to optimize the possibility that the subject or patient will at some point in time be positioned between the separate housings. In one example, every chair in the room may contain a device 10 or part of a device 10. As noted earlier, these separate housings may have different forms. For example, one housing may look like a cup and another housing may look like a water dispenser. Also, as noted earlier, the devices 10 or parts of devices 10 may have different sets of sensors or stimulus emitters.

Figure 2:
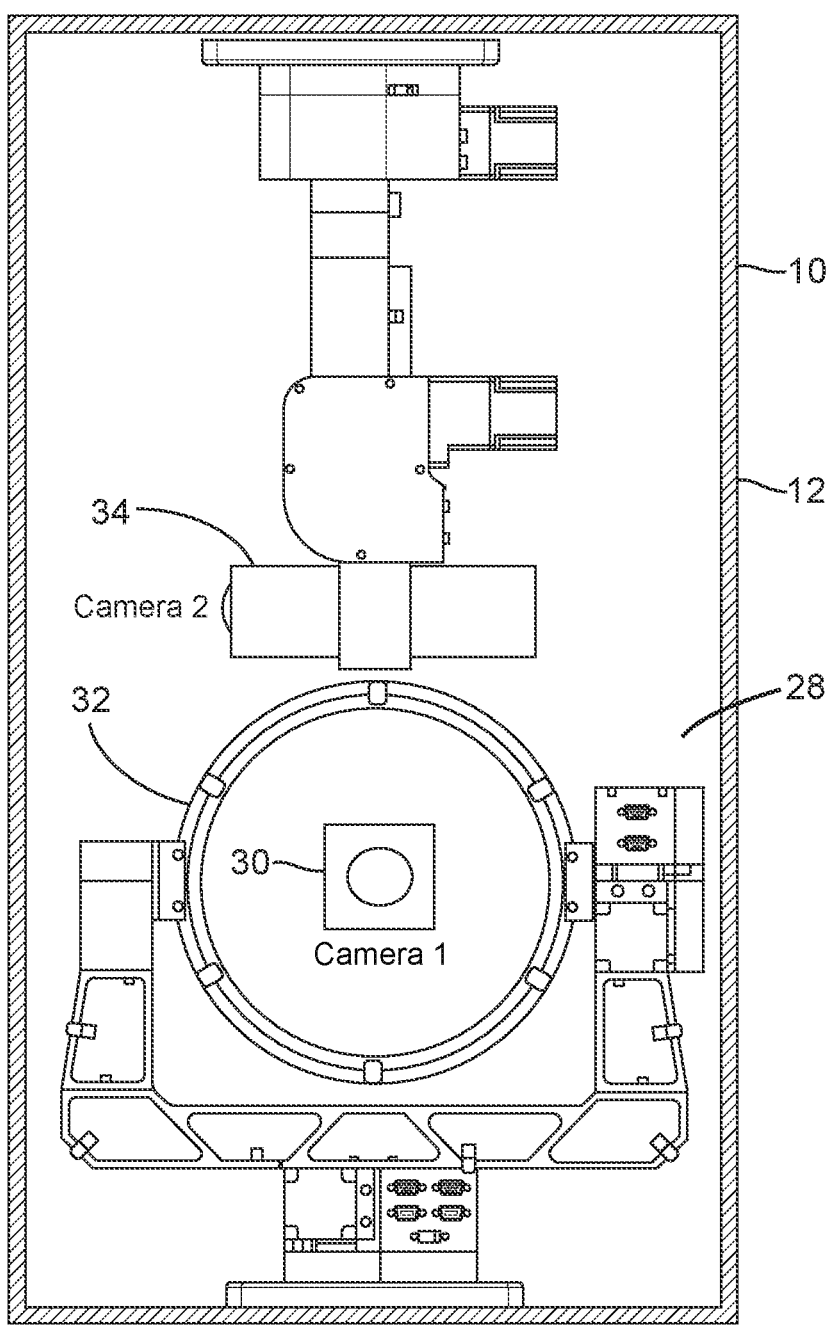
FIG. 2 illustrates the mechanism inside the mugs of FIG. 1.

FIGS. 2 and 3 illustrate the interior 28 of the device 10 of FIG. 1. FIG. 2 illustrates an embodiment in which a camera 30 is mounted on at least one gimbal 32 that is rotatable about a single axis. One or more other cameras such as camera 34 may be provided within the device, either on a gimbal or on another type of mount.

The gimbal may be mechanical or motorized, with the embodiments of FIGS. 2 and 3 being motorized. In a gimbal system in which the gimbal is rotatable about a single axis, a single gimbal motor is provided. In an alternative embodiment, a gimbal that is rotatable about two axes is provided.

A three-axis gimbal is a feature of a further alternative embodiment. Powered by three brushless motors, motorized gimbals have the ability to keep the camera level on all axes as the camera operator moves the camera. An inertial measurement unit (IMU) responds to movement and utilizes its three separate motors to stabilize the camera. With the guidance of algorithms, the stabilizer is able to notice the difference between deliberate movement such as pans and tracking shots from unwanted shake. This allows the camera to seem as if it is floating through the air. Optionally, the center ring may be vertically fixed.

Figures 3A, 3B, 3C:
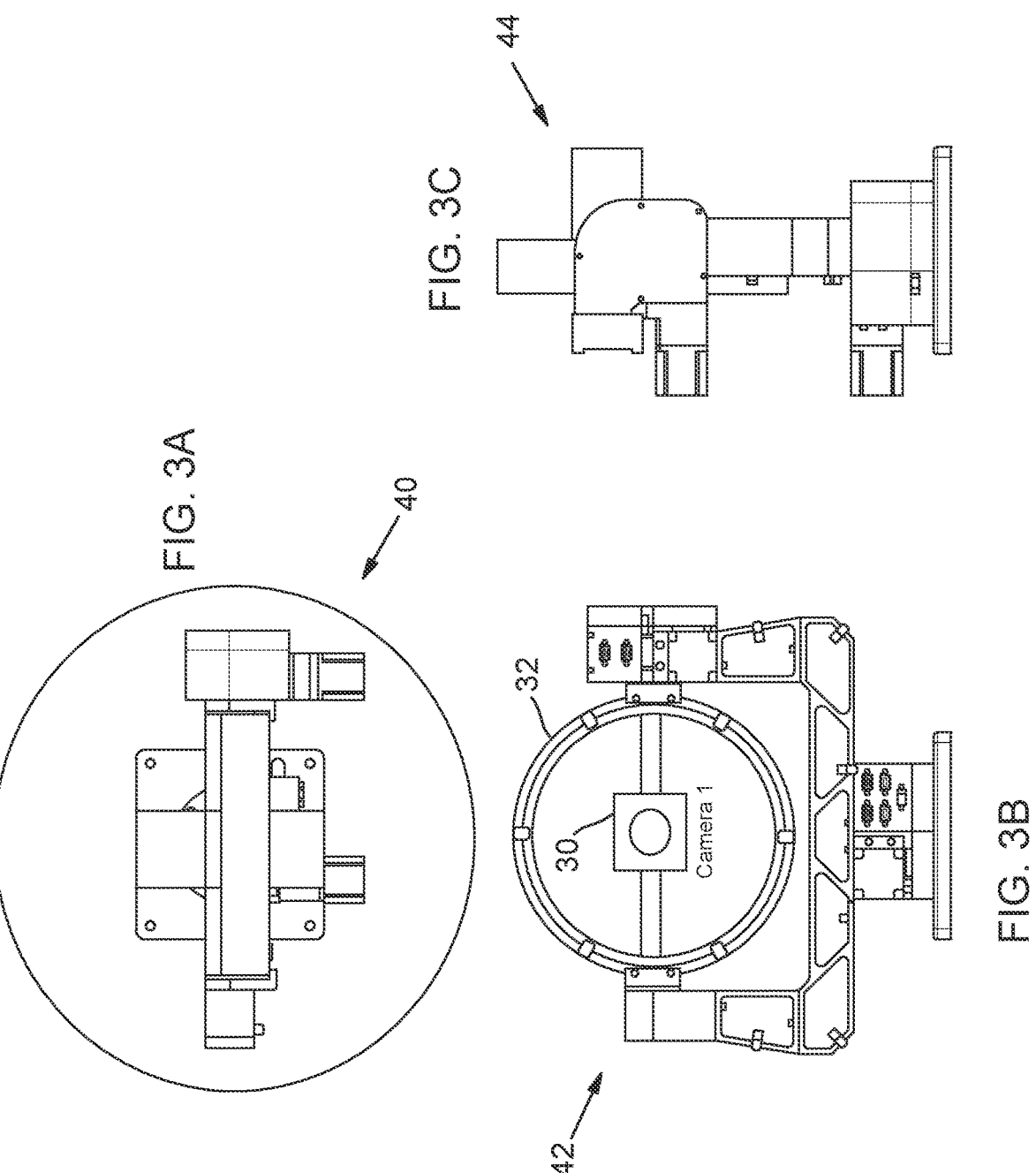
FIGS. 3A-3C further illustrate the mechanism inside the mugs of FIG. 1.

FIGS. 3A-3C (collectively FIG. 3) illustrates top 40, front 42, and side 44 views of a gimbal mounting system for a camera.

As previously noted, sensors located inside of the mug will "see" right through the mug material. The portion(s) through which the sensors see is mirrored on the exterior, such that a user 22 will see a reflection from outside the mug. But the film is translucent, and sensors inside the mug may view and/or sense objects that are outside the mug.

At this point, further understanding of aspects of the invention will be facilitated with consideration to concepts of noise, adaptability, error states, adverse user experience, control factors, and algorithms.

A variety of sources can cause noise. As examples, noise can be created by heat, vibrations, electromagnetic fields, movement, force, vibrations, shock, and other sources. One or more of these may be caused by interaction with other devices according to the present invention located nearby. Noise may be caused through direct contact of the units, connection, and/or proximity. Embodiments of the present invention may include filter circuitry or other means to sense and cancel out such noise.

Various embodiments of the present invention may be durable and adaptable to changing conditions. For example, a unit may be subject to factors such as: different lubricants, high pressure or other forms of cleaning, irregular service intervals, incorrect pressure or flow settings, movement such as being transported by trailer or the like where stability and temperature are not constant, aftermarket parts are used, and different users who use the device in different ways.

Normal degradation of components or materials can lead to decreased performance or even a partial or full loss of system function. As examples, the following may occur in a particular embodiment: corrosion, fatigue, wear, oil degradation, seal ageing, and/or other factors. Alternatively, embodiments of the present invention may be subject to adverse environmental conditions. Such conditions may include water, snow, debris, mud, road salt, dust, stone impact, humidity, ambient temperature (e.g. cold and hot temperatures).

To mitigate effects from the foregoing conditions, it is preferable to employ durable materials, extensive testing, and algorithms that can detect degradation as it occurs so that measures to prevent further degradation and/or system performance may be taken. The measurement may include sensors to detect such factors, and/or algorithms to process information from the sensor and determine corrective measures and/or make design improvements to optimize performance of the system.

A device according to the present invention may be subject to failure modes that hinder the work and/or function of a device or component. Performance loss may be an effect. Non-limiting examples of error states may be generated by: corrosion, fatigue, difficult service, contamination of fluid, friction, temperature, and/or other conditions adverse to the functioning of the device or component.

A system may work well yet have undesirable effects from an engineering and/or user experience. In the case of a user 22, an undesirable effect may be a result of undesirable feel, audible sense, smell, visual, taste—anything undesirable that may be detected by the physical senses. A user 22 may not like the look of a device 10, for example. Or the device 10 may emit sounds that the user 22 dislikes. It may generate a scent during operation that is undesirable to the user 22. In rare circumstances, the user 22 may experience an undesirable taste in the mouth.

Other adverse user experience factors may include time it takes for a device 10 to complete a procedure, distracting movement of a device 10 and/or its components, shape that does not fit well into the environment in which it operates, and numerous intangible factors that might be best understood by spending time in the shoes of the user 10.

An engineering and/or design team have variables within their control to optimize the function of a system according to the present invention. Non-limiting examples of such variables include: material, dimensions, coating thicknesses, surface finish, sensor type, actuator speed, and many other engineering and/or design variables.

One embodiment of the present invention includes an algorithm that compares such variables to references in a library. The library may be onboard the device 10, partially onboard and partially remote, or fully remote. The algorithm may compare what it finds in the library with variables the engineering and/or design team has selected. The algorithm may make suggestions as to more optimal variable selection, from a system performance standpoint and/or from a user experience standpoint. Reference to the library may help conform a design parameter to best practices, proven design features, user preferences among specific demographics, and other information that may be useful to engineers and designers.

Algorithms selected for use in conjunction with the present invention will perform numerous steps. For example, in one embodiment, an algorithm: a) populates a modular unit based on the unit's intended function and/or outputs; b) identifies inputs; c) identifies noise inputs; d) identifies error states; e) identifies unintended inputs; and f) scans and operates a device 10. The foregoing steps may be performed in a different order than the foregoing, in a specific situation.

The algorithm preferably includes countermeasures for encountered noise. This may include filtering, use of active controls, and/or facilitating user intervention. For example, in one embodiment, a user 22 may be provided with the opportunity to select from a variety of modes, such as: a) ignore the noise; b) control or eliminate the noise; c) compensate for effects of the noise; and/or d) minimize the effects. In other embodiments, no input from the user 22 is necessary or desired, and the type and level of control is implemented independent from the user 22.

Returning to the embodiments of FIGS. 1-6, as output the device 10 may transmit data, photos, information about error states and/or undesired side effects, and/or other collected information. An external processing system processes the information, as will be described below. Information concerning the growth of the tumor may be transmitted back to the mug device 10, for display on the lid screen, and/or for reporting in other ways, such as via audio. The device 10 may be equipped with an interactive voice system analogous to Amazon's Alexa, in which the system provides an oral report on command and can answer pre-selected questions.

Figure 7:
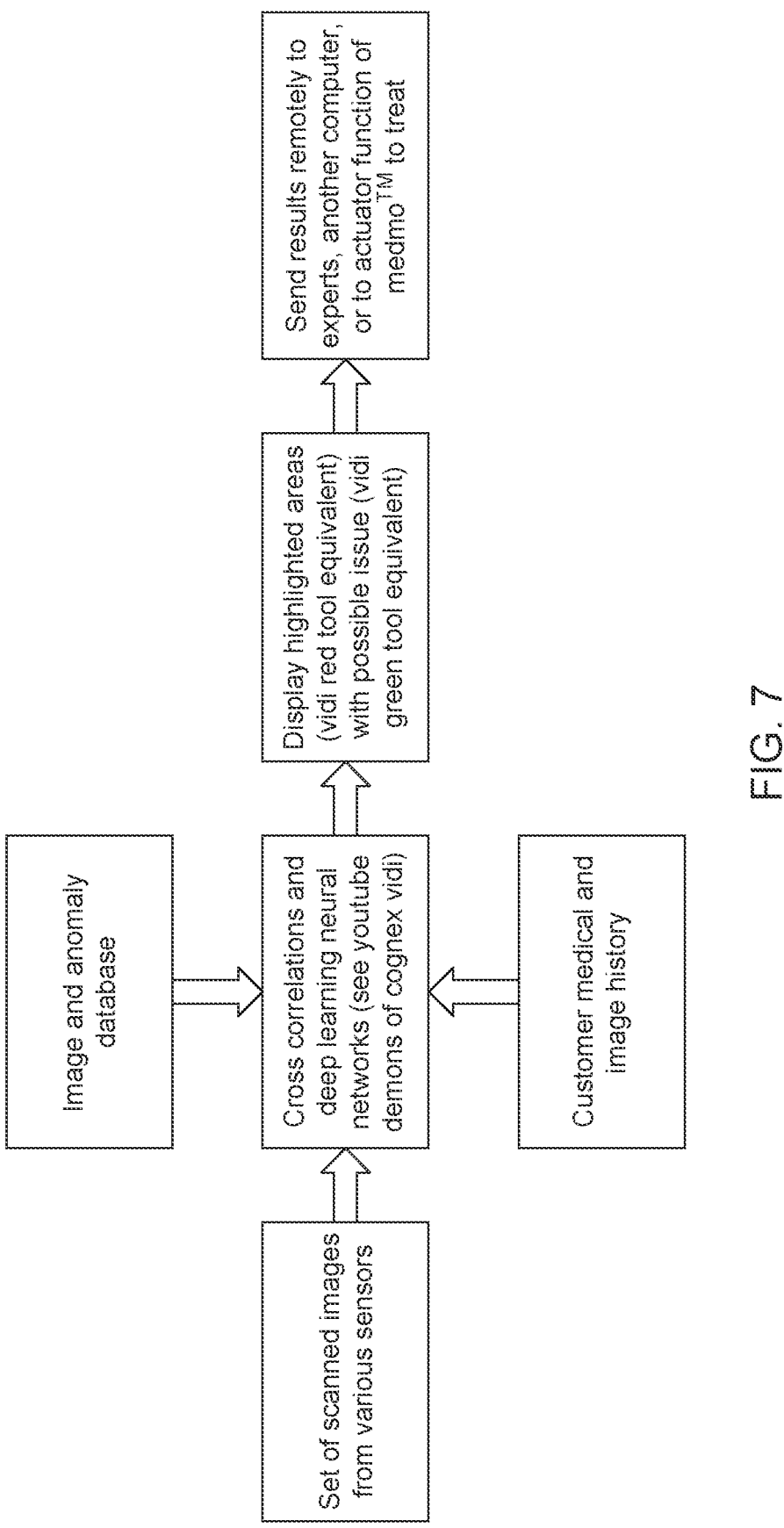
FIG. 7 is a process diagram showing analytical steps that may be associated with assessment of the condition of the user.

FIG. 7 illustrates a robustness algorithm. The algorithm is to compare data to a library and display final highlighted results on a screen. The display may overlay onto a subject scan.

In a room of multiple people, for example, data about just one person may be desired. Consequently, the unit is adapted to isolate data (e.g. photos) taken of one person the user selects on the touch-screen lid and/or remotely such as from an app on a computer and/or mobile phone.

Figure 4A:
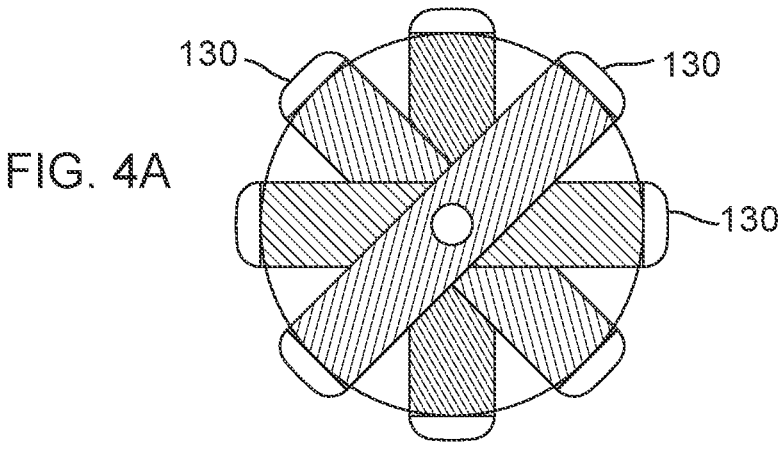
FIGS. 4A and 4B illustrate an array of sensors inside the mug.
Figure 4B:
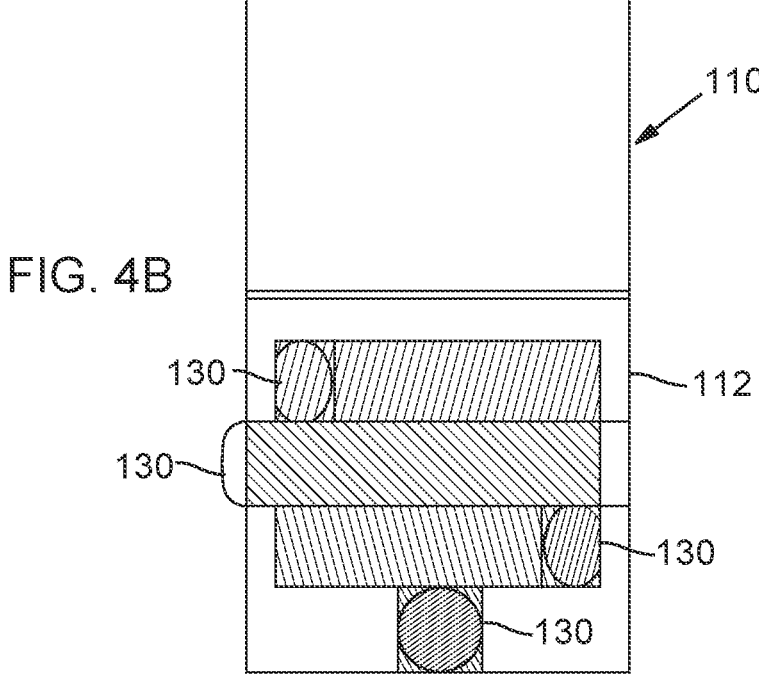

Referring to FIGS. 4A and 4B (collectively FIG. 4), another embodiment incorporates a "spiral" camera concept. Inside the mug, there are 8 miniature cameras and/or sensors, generally represented as cameras or sensors 130. The lenses are snap inserted/press fit after the camera package is dropped into the mug 110. A laser pulse may be made through the same lens. Alternatively, a scanning laser may be located on top of camera array. The cameras and/or sensors are adapted to "see" through the wall 112 of the cup.

In a further embodiment, a fluid seal may be provided on top to simulate having coffee in the mug. The user 22 may have to "drink" it to view the interactive screen, which may be a touch screen or have scaled button controls.

Figures 5A, 5B:
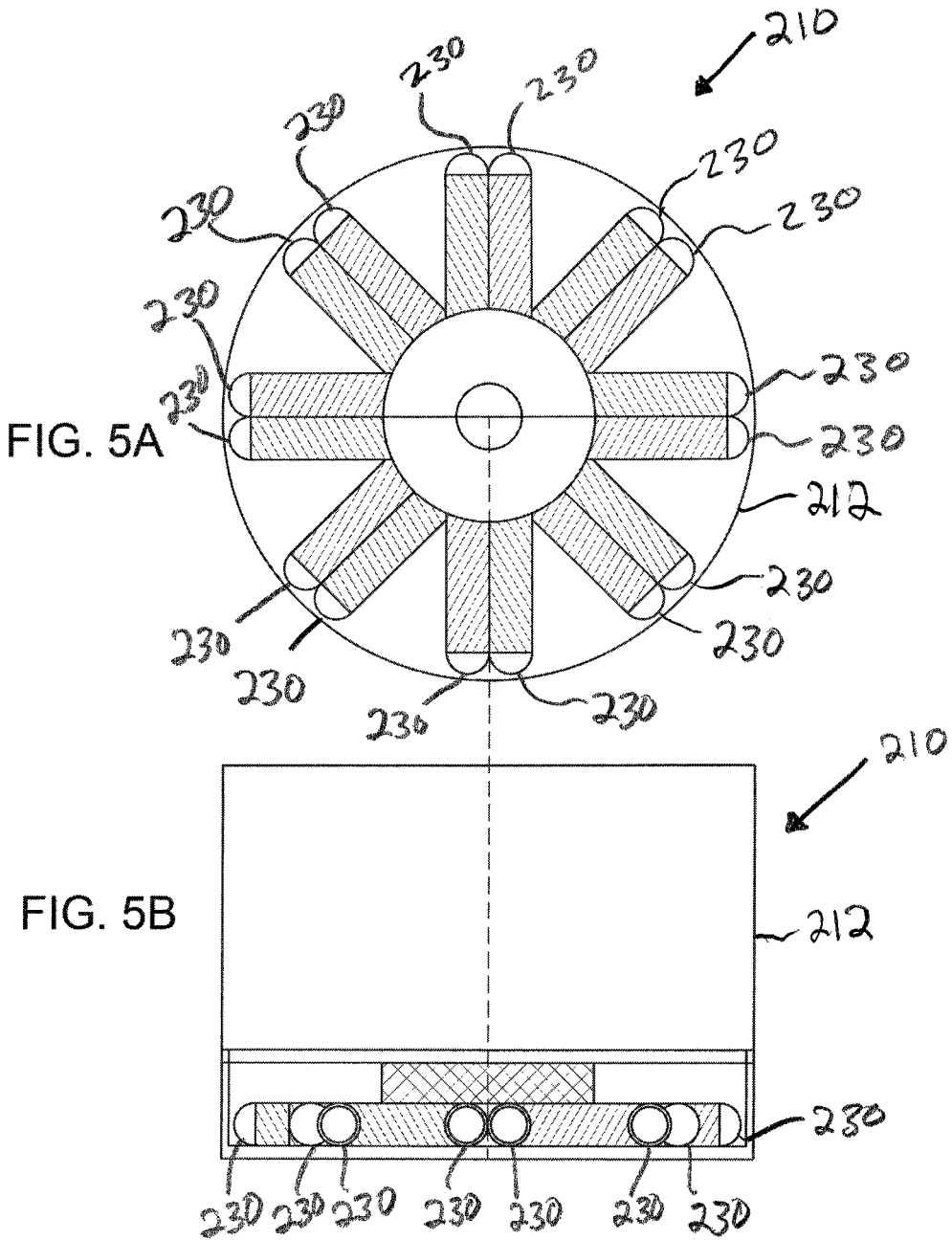
FIGS. 5A and 5B illustrate an alternative array of sensors.

In another embodiment of the portable device 210 illustrated in FIGS. 5A and 5B (collectively FIG. 5), active sensors 230 are employed in sender/receiver pairs. The sensors 230 may be in one plane, and they are rotated and/or they track (such as through a circumferential portion of the wall 212) a moving human, animal, or object's internal organ, structure, or component. The device 10 includes a vertical central "pole" that rotates. The drive motor is at one end, with electronics.

Another variant would be two intertwining spirals (not unlike DNA), where one set is sender-receiver active sensors 230, and the other is passive sensors 230. Rotation can be only as needed, or alternating, to keep track of changes from the last scan—taking turns. The spirals allow for perspective/3D and hologram effect/fill-in for blocked view/mathematical compensation for reflections.

In another embodiment, the device 210 has two sets of active sensors 230, which may be continuously spinning, sometimes spinning, or no movement at all. The sensors 230 may be in a sequential phased array. Each pair would be turned on in sequence, the first turned on right after the last. A three-axis accelerometer and gyro may sense movement of the mug, which is an alternative to the gimbal mechanism previously discussed.

As a further option, the top of the interior mechanisms and electronics may be further down the cup. The mug can then hold a liquid. This does not have to always be surreptitious. It might even hold a liquid medicine or relaxant for the patient being scanned. The device 10 can be scanning the patient while they take the mug, lift to their lips, hold and chat, and even hand it back.

Figures 6A, 6B:
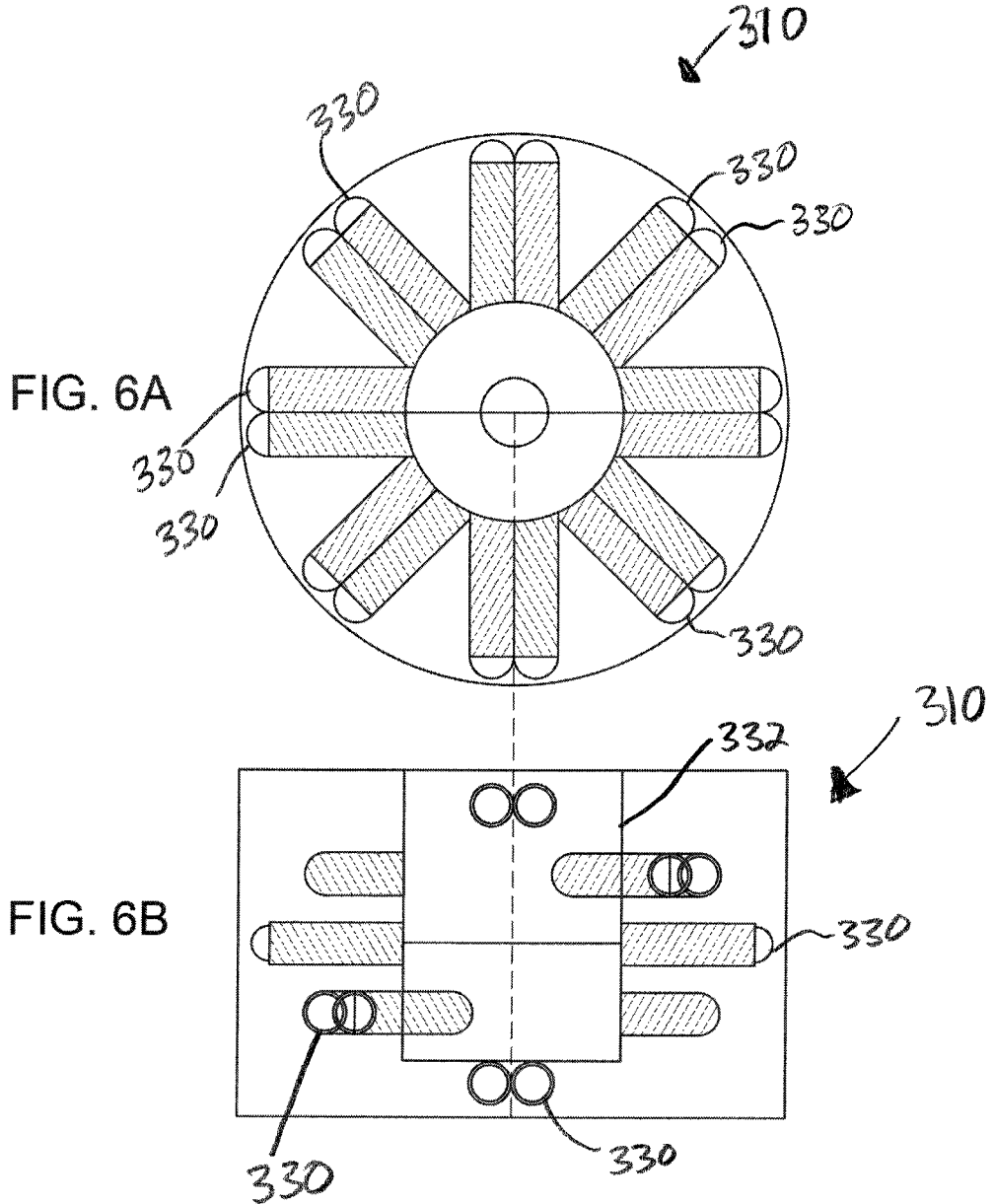
FIGS. 6A and 6B illustrates another alternative array of sensors.

FIGS. 6A and 6B (collectively FIG. 6) illustrate another embodiment of the portable device 310 in which the sensors 330 are provided in a unit 332 that is separate from and attachable to the cup. One will appreciate that these sensors 330 may alternatively or additionally be employed within the device 10. The unit may be snapped or twisted onto the cup, such that the cup may be used to hold liquid. The unit is self-contained with battery and electronics, and the battery may be wirelessly charged with standard cell phone wireless charging, or other charging means.

Considering further aspects of select embodiments of the present invention, the mug will know its location, relative to its initial scan, with the same components inside of a cell phone that convey change in orientation and location. Sec, e.g., https://www.gsmarena.com/glossary.php3?term= sensors.

Smartphones today come with a wealth of sensors 330 to facilitate a better user experience, provide apps with enhanced information about the world around the phone and provide robust and increased battery life. One is a proximity sensor, which detects when an object is near to the phone. Most commonly used to sense when a phone is held up to the user's car to turn off the display. This saves both battery life and prevents accidental screen touches.

Other types of sensors 330 are accelerometers and gyroscopes. Accelerometers in mobile phones are used to detect the orientation of the phone. The gyroscope, or gyro for short, adds an additional dimension to the information supplied by the accelerometer by tracking rotation or twist. An accelerometer measures linear acceleration of movement, while a gyro on the other hand measures the angular rotational velocity. Both sensors 330 measure rate of change; they just measure the rate of change for different things.

In practice, an accelerometer will measure the directional movement of a device 10 but will not be able to resolve its lateral orientation or tilt during that movement accurately unless a gyro is there to fill in that info. With an accelerometer you can either get a really "noisy" info output that is responsive, or you can get a "clean" output that's sluggish. When a 3-axis accelerometer is combined with a 3-axis gyro, an output may be both clean and responsive.

Accelerometers are also used to provide 'steps' information for a vendor's 'health' application.

Another mobile phone sensor 330 is a digital compass. The digital compass that's usually based on a sensor 330 called the magnetometer and provides mobile phones with a simple orientation in relation to the Earth's magnetic field. As a result, your phone always knows which way is north so it can auto rotate your digital maps depending on your physical orientation.

Another common mobile phone sensor 330 is a barometer. The barometer assists the GPS chip inside the device 10 to get a faster lock by instantly delivering altitude data. Additionally, the barometer can be utilized to provide 'floors climbed' information to a phone's 'health' app. With the advent of more accurate indoor navigation, the barometer can assist in determine what floor a user 22 is on within an airport for example.

Biometric sensors 330 provide levels of enhanced security by capturing and validating human related metrics. Including fingerprint recognition, IRIS (eye) scanning and full facial recognition. Biometric sensors 330 provide a more secure but more convenient way to unlock phones and pay for purchases. Additionally, biometric sensors 330 can be used to collect a user's heart rate and SpO2 (the estimate of arterial oxygen saturation) for use within a vendor's 'health' application.

Some sensors 330 may relate to augmented & virtual reality. The highly accurate sensors 330 detailed above, when combined with the powerful CPUs and GPUs of modern smart phones, allow very realist and responsive virtual reality applications to be created. When the sensors 330 are combined with a smartphone camera they facilitate augmented reality applications.

Figure 8:
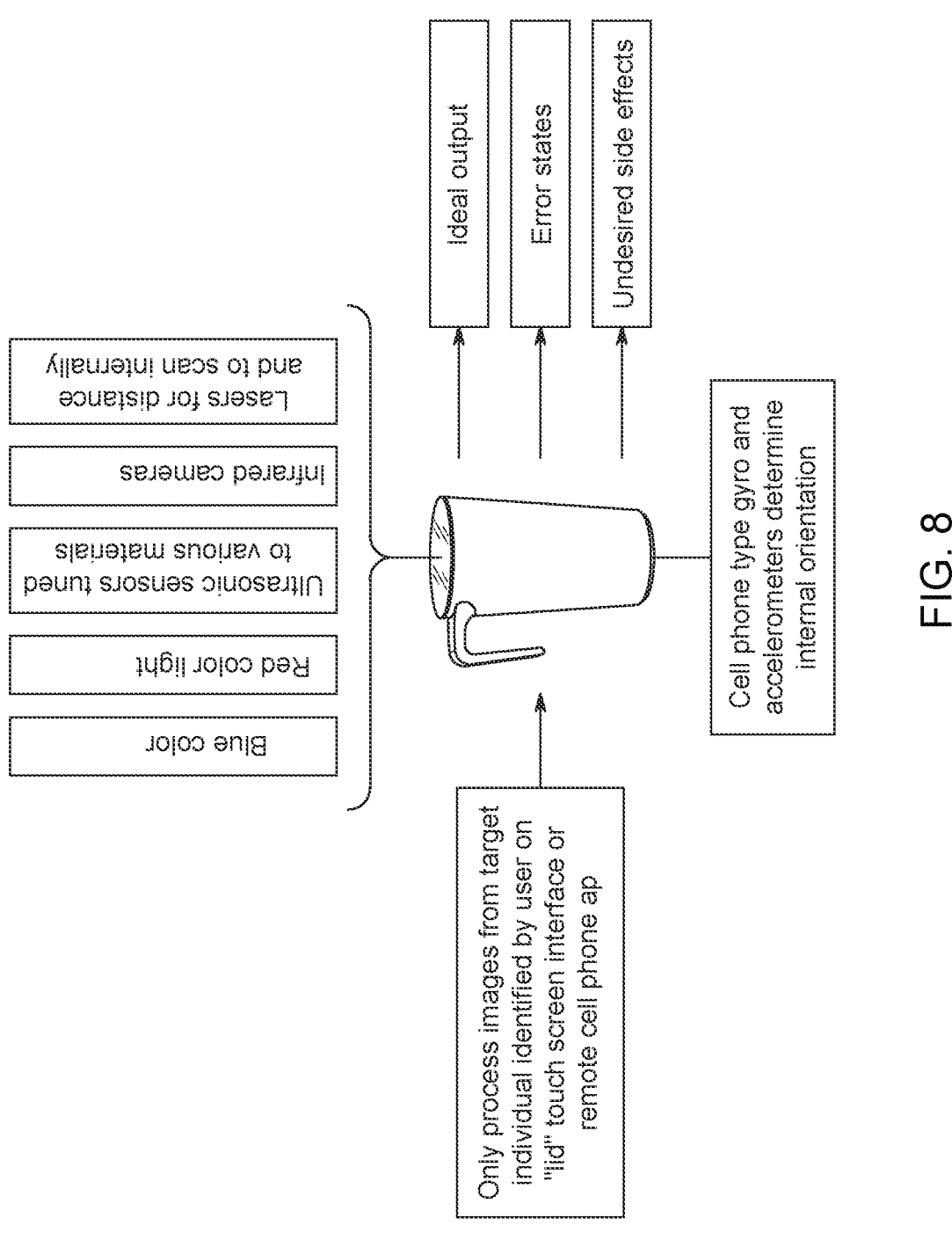
FIG. 8 shows examples of sensor inputs and outputs associated with a portable assessment device.

Turning to FIG. 8, one embodiment of a mug device 410 has various characteristics. The device 410 may include a variety of devices, such as various colors of lights, lasers, ultrasonic sensors, infrared and/or other types of cameras, various emitters, and the like as desired for particular applications. The device 410 may include gyros, accelerometers, and other sensors 330 as described above. These various sensors and emitters and their controllers are commercially available in miniature sizes and may all be packaged into the device 410. The user 22 may control various aspects of the operation of the device 410 from a touch screen, such as a circular touchscreen at the "mouth" of a cup device 410, or from a cell phone or other remote device that is in communication with the cup device 410. The device 410 may output a variety of outputs, as discussed. The device 410 may also output what is estimated to be ideal output, error states, and undesired side effects from a particular application.

The embodiment of FIG. 8 is configured to gather data about a patient, then transmit the data to an external processing system to predict future growth of a tumor. Graphical and/or other data may then be displayed on a screen, such as on the lid of the mug. The mug may be adapted to provide lighting of any desired type, such as blue light, red light, or other desired illumination, including types of illumination not visible to the human eye, if desired. A variety of sensors are housed within the mug: one or more ultrasonic sensors, an infrared camera, and/or lenses for distancing and to scan internally, devices for determining the internal orientation such as gyro(s) and accelerometers, among other possible sensors.

Considering now an algorithm for scanning and processing, a scanning device generates a set of scanned images from various sensors, such as from the foregoing coffee cup and/or other embodiments. A system then performs cross-correlations and implements deep learning neural networks, drawing from one or more libraries/databases of images and anomalies and/or customer medical and image history. Signals are then sent to the display, to display areas of the body with possible issues. The highlighted areas may be color-coded, such as with red or blue. Results may also be sent to experts located remotely to another computer, or to an actuator function to perform treatment on the user 22.

As background, neural networks are computer programs that are designed to mimic how a human brain operates. They have become the method for how computers learn to perform certain tasks, say recognizing a specific face across different photographs or identifying what a dog is or isn't from a reference set of dog pictures. For further background on neural networks, see "How a Neural Network Helps Manufacturing Inspection," Cognex Corporation, available at https://www.cognex.com/blogs/deep-learning/what-is-a-neural-network.

Concerning the steps of cross correlation, deep learning neural networks, and displaying highlighted areas of possible interest, a tool may detect defects on complex body parts and surfaces. One step is to locate the object (e.g. a part of the body) of interest. Often the object has complex features. The background may be noisy, poorly lit, low contrast, and may flex or change shape. Consequently, the tool must locate objects despite variations in perspective, orientation, luminance, glare and color by learning from samples provided by the user 22. The system may be trained to find a variety of components that may have a different appearance or vary in size, in order to create an extensive component library. The tool may check multiple feature locations and component types simultaneously, while adjusting to various body layouts.

Alternatively, a sample set of good images and bad images with labeled defects may be used. The system should tolerate normal variations, while detecting true anomalies. For situations where it is difficult to collect images of defects, or if failure modes are unknown, the tool may learn the normal condition by, for example, scanning healthy bodies. After enough samples, it can identify images that stray from this normal appearance.

The tool may also segment areas of an image. The tool can learn to identify areas of abnormality and/or interest. The tool can highlight those areas and, for example, shade them a predetermined color on a display. A commercially available system that performs similar functions is available as the Cognex VisionPro ViDi Red system, available from Cognex Corporation of Natick, Massachusetts. https://www.cognex.com/products/machine-vision/vision-software/visionpro-vidi Referring to FIG. 7, several steps in one method according to one embodiment of the present invention are illustrated. The sensors gather a set of scanned images. A system such as, for example, as the Vidi system of Cognex Corporation performs cross-correlations, uses deep learning via neural networks or the like, and/or data analysis statistical techniques, drawing on customer data such as medical and image history, a database of images and anomalies, and/or other databases or sources of information. After this step, areas of a sensed image are highlighted, and areas with a possible issue (e.g. identification of potential medical issue) are displayed. In one embodiment, data is transmitted from a processing center back to the device and/or another display such that the user, a medical professional, or others may view the data and make recommendations, prescriptions, treatments, as appropriate.

Systems according to the present invention may also utilize a classifier that can be used to distinguish between different types of objects, identify defect types, and inspect images. Learning from a collection of labeled images, the tool may identify and sort products into classes based on their common characteristics such as color, texture, materials, packaging, and defect type. The tool tolerates natural deviation within the same class and reliably distinguishes acceptable variation from different classes. A commercially available system that performs similar functions is available as the Cognex VisionPro ViDi Green system, also available from Cognex.

As noted, devices according to the present invention often have the capability to multitask. For example, each type of diagnostic is better at identifying/differentiating different kinds of tissue. We also have a pretty good understanding of the degree of confidence we have for each item identified as a candidate for a specific category. How to calculate confidence levels. See https://sciencing.com/calculate-confidence-levels-2844.html. Using GPS as an example, accuracy can be compromised by reflections, partial blockage, lower degrees of correlation with examples in a database, and being too close to the transition between two candidate categories.

Multiple sensors, using compatible software, can get crucial alternate views to estimate 3D dimensions. These can be as simple as one above and below a table, but can also be mounted on a belt, left and right sides of the user's or patient's body (esp. if used for monitoring a condition that could change suddenly). This is more than just a FitBit, for example. But the FitBit has made such monitoring not only accepted, but to be expected.

As a supplement to the foregoing, to understand how every joint changes your orientation, see for example https://www.bhphotovideo.com/c/product/1492980-REG.

It is best that each sensor 130 or 330 have its own ability to collect its own data, then pass that data in an appropriately sampled fashion to the controller board for signal conditioning, drop out interpolations, sensor fusion, false alarm rejection, and cross correlation with library images/features, followed by orientation to a global reference for path planning for any directed action (light/ultrasound/air jet, needle, laser, or blade) in 3D environment (actually 4D, with time variation, as living material moves, so often we need prognostics to predict expansion/contraction, drift/float, and/or dispersion/absorption of tissues).

Regarding the processing units and CPU, relationships can be trained with neural networks, and use correlations to reference cases, some of which might be the actual patient, to track changes and send to doctor. Depending on the features, and complexity of a given set of possible categories, a regular processor may be used for a simple cross correlation, whereas a bank of parallel processors may be needed for deep learning. In the latter case, heavy computer lifting needs to happen on a server. Send the images and//or keep features of those images, wirelessly to that server or to multiple processing facilities around the world hat maintain the best database for the suspected malady. This can readily be scaled up as data accumulates and the device becomes popular, so existing databases adapt their interfaces to share info.

The device and/or external processing system may be programmed with a variety of computer languages, such as R and the higher and lower-level languages mentioned in this wiki article. See https://en.wikipedia.org/wiki/R_(programming_language). The "mugs" can act as their own robots, calculating where they are, and where they have been, with respect to a global reference, for example, on the end of a human arm (or static on a table, rotating some sensors with a gimbal/gyro internally).

Figure 9:
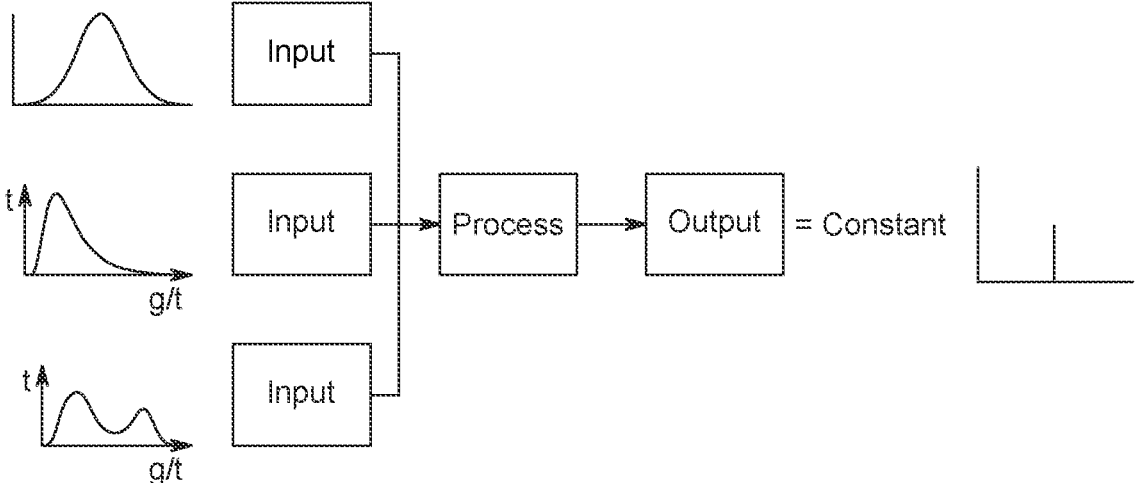
FIG. 9 shows examples of how a portable assessment device can sense and adjust to environmental conditions.
Figures 10A, 10B, 10C, 10D:
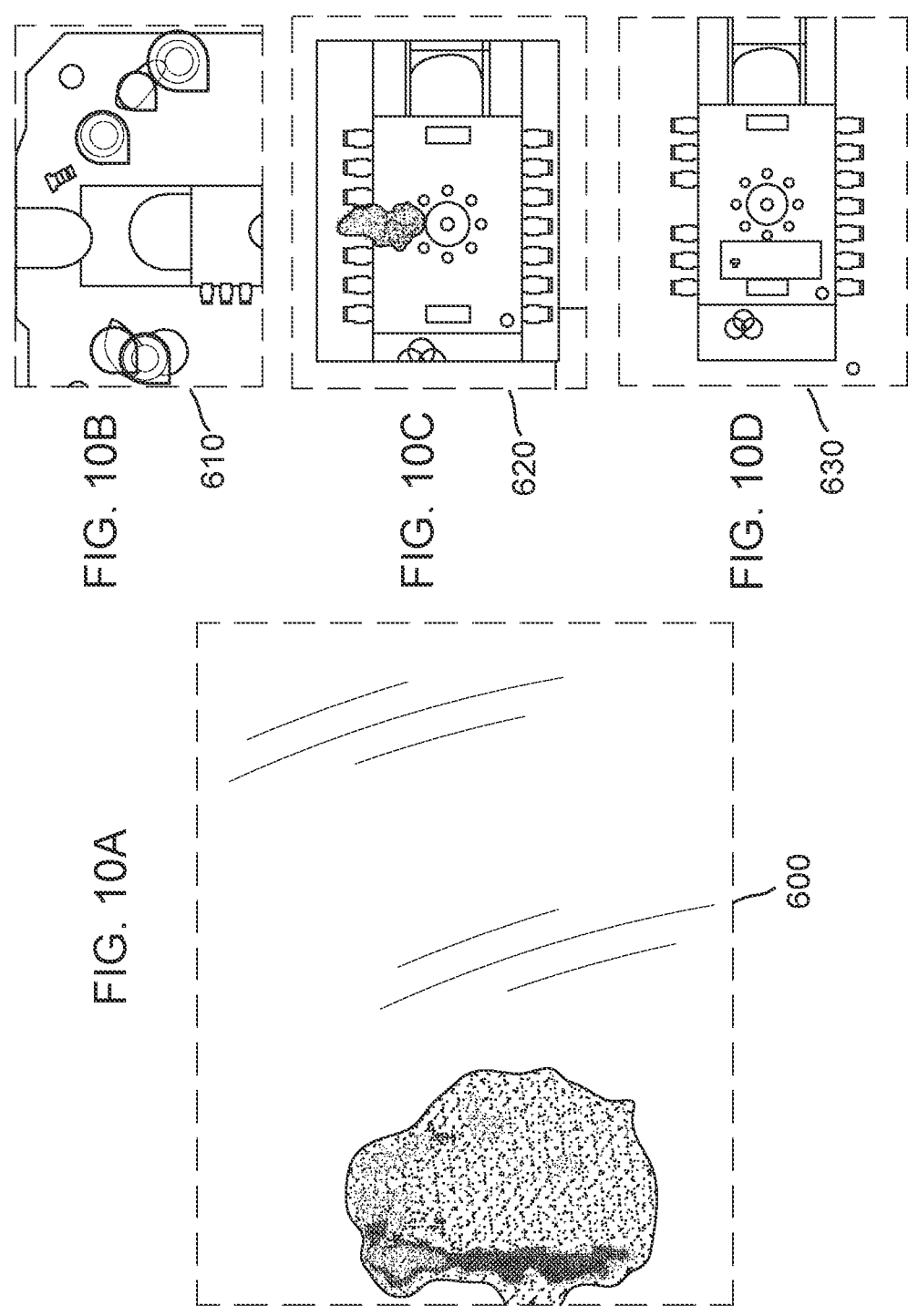
FIGS. 10A-10D illustrate a four-step process for analyzing images.
Figures 11A, 11B, 11C, 11D:
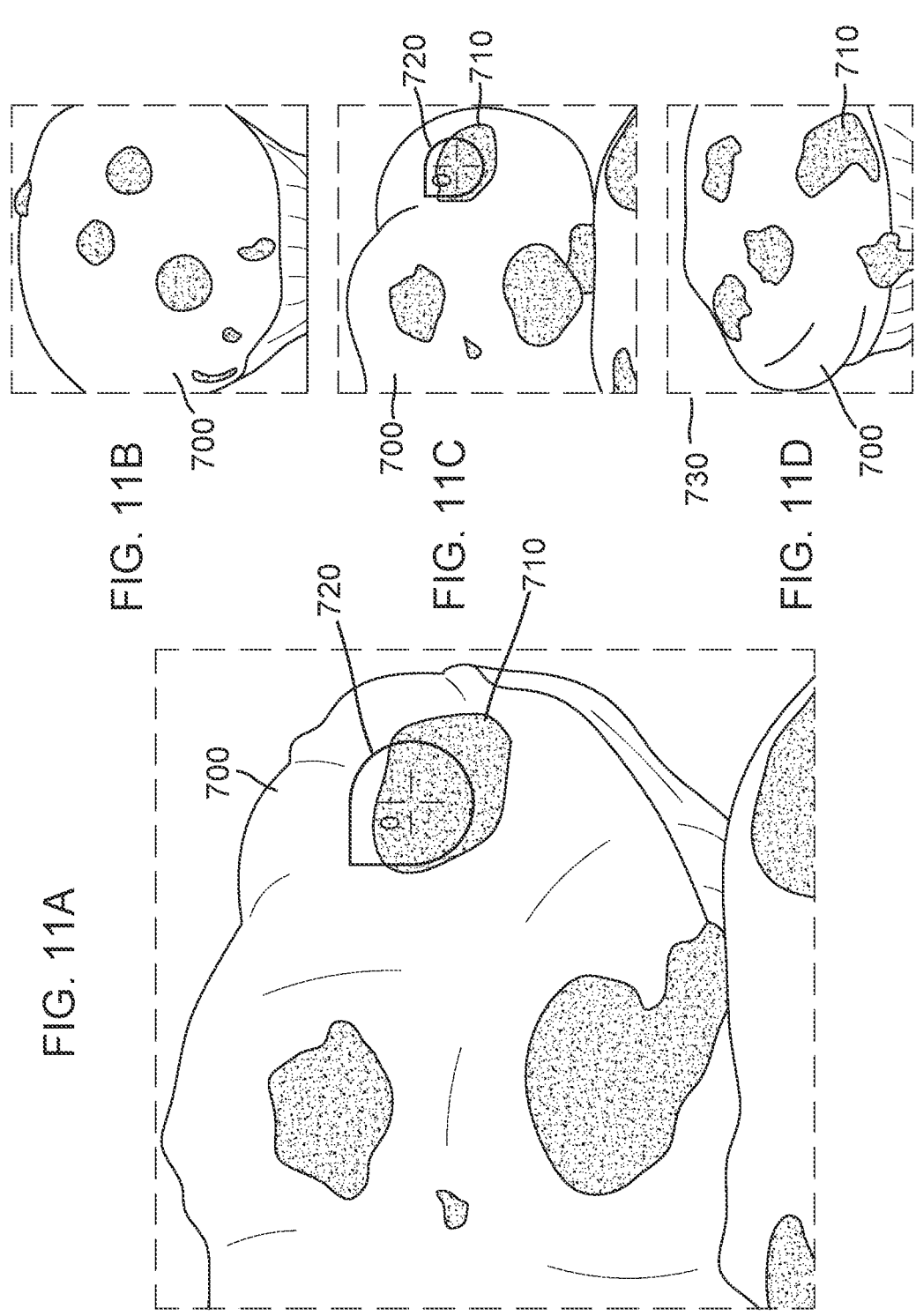
FIGS. 11A-11D illustrate a step in visually analyzing a blueberry muffin.
Figures 12A, 12B, 12C, 12D:
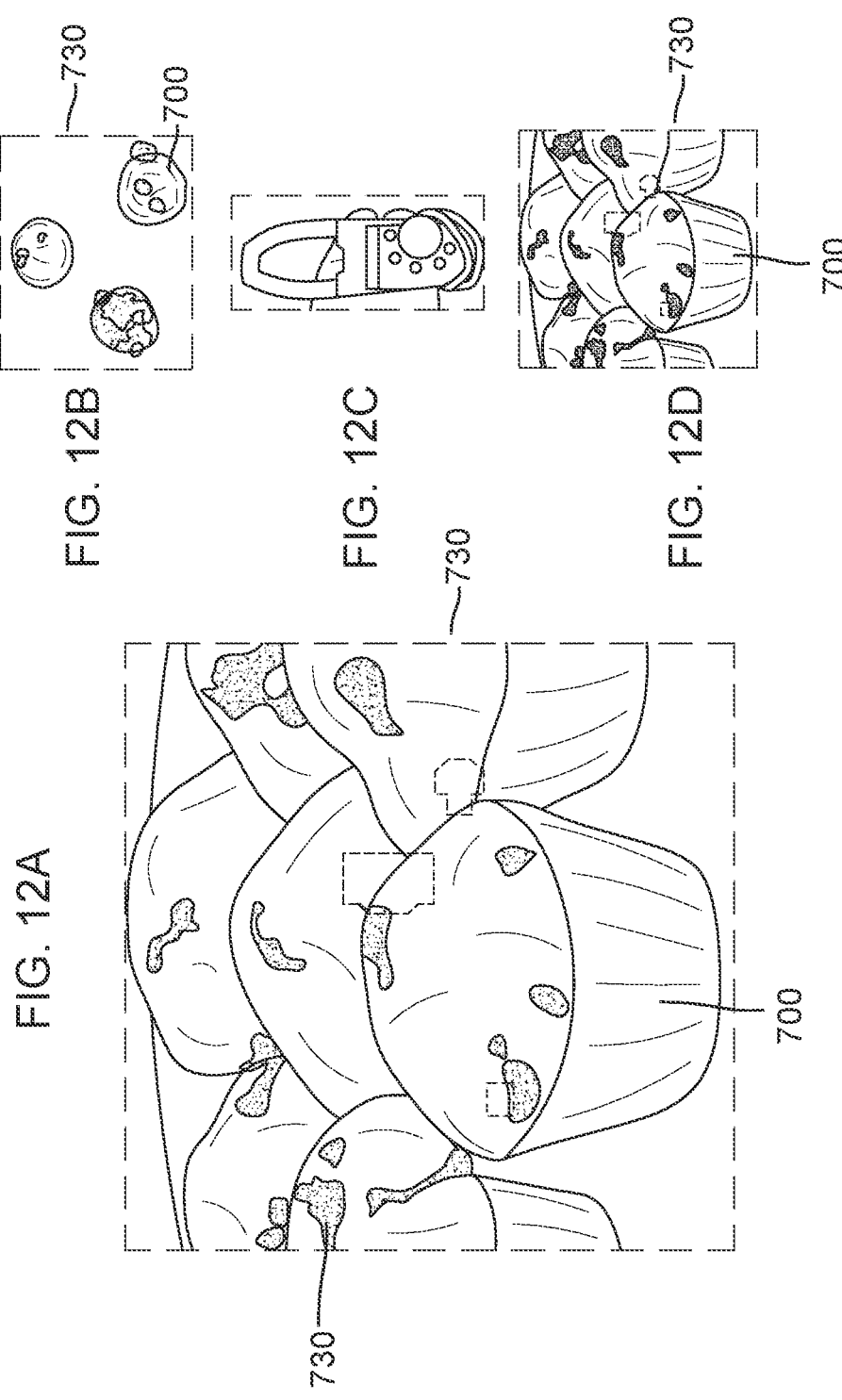
FIGS. 12A-12D illustrate another step in analyzing an image of a blueberry muffin.
Figures 13A, 13B, 13C, 13D:
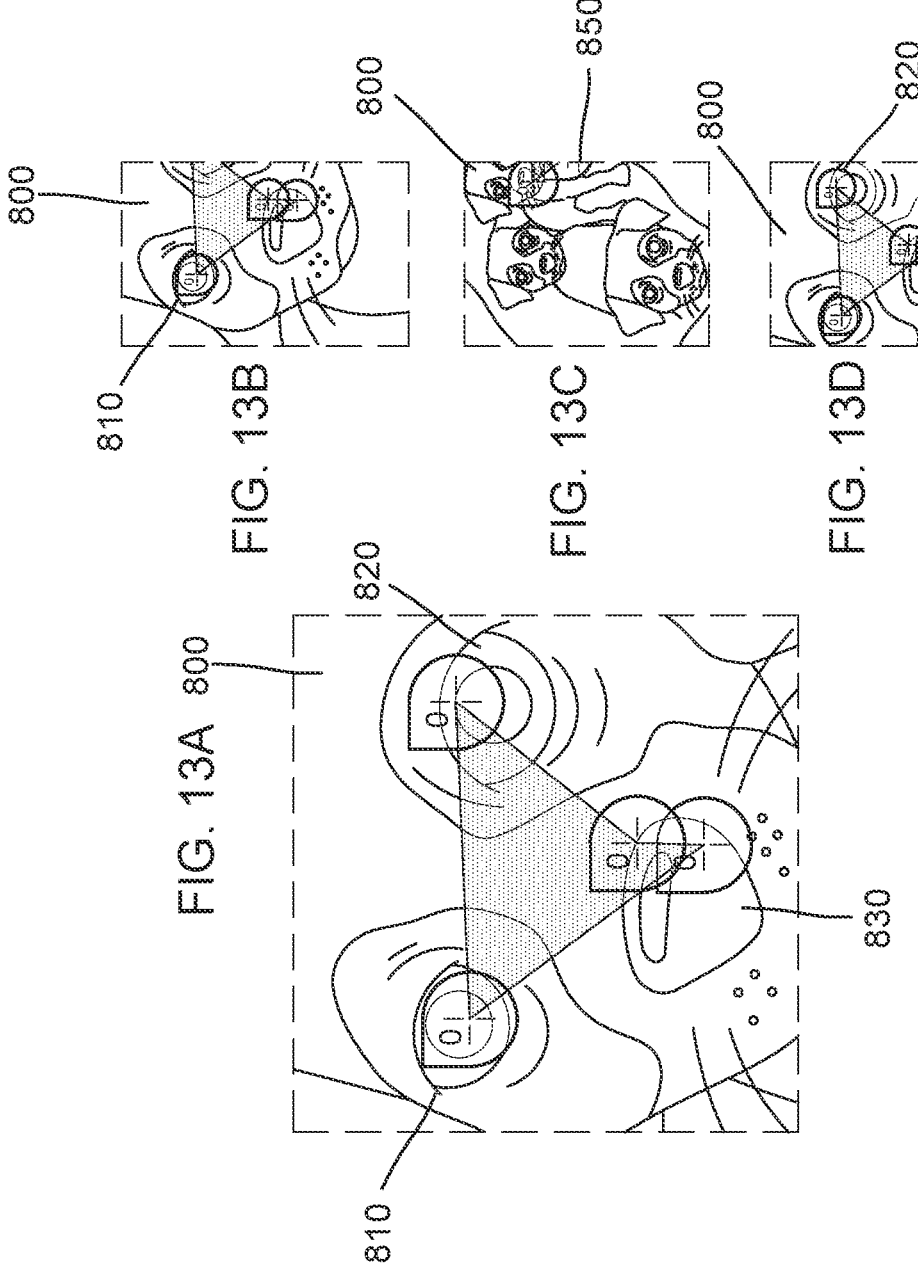
FIGS. 13A-13D illustrate a step in analyzing the face of a small dog.
Figures 14A, 14B, 14C, 14D:
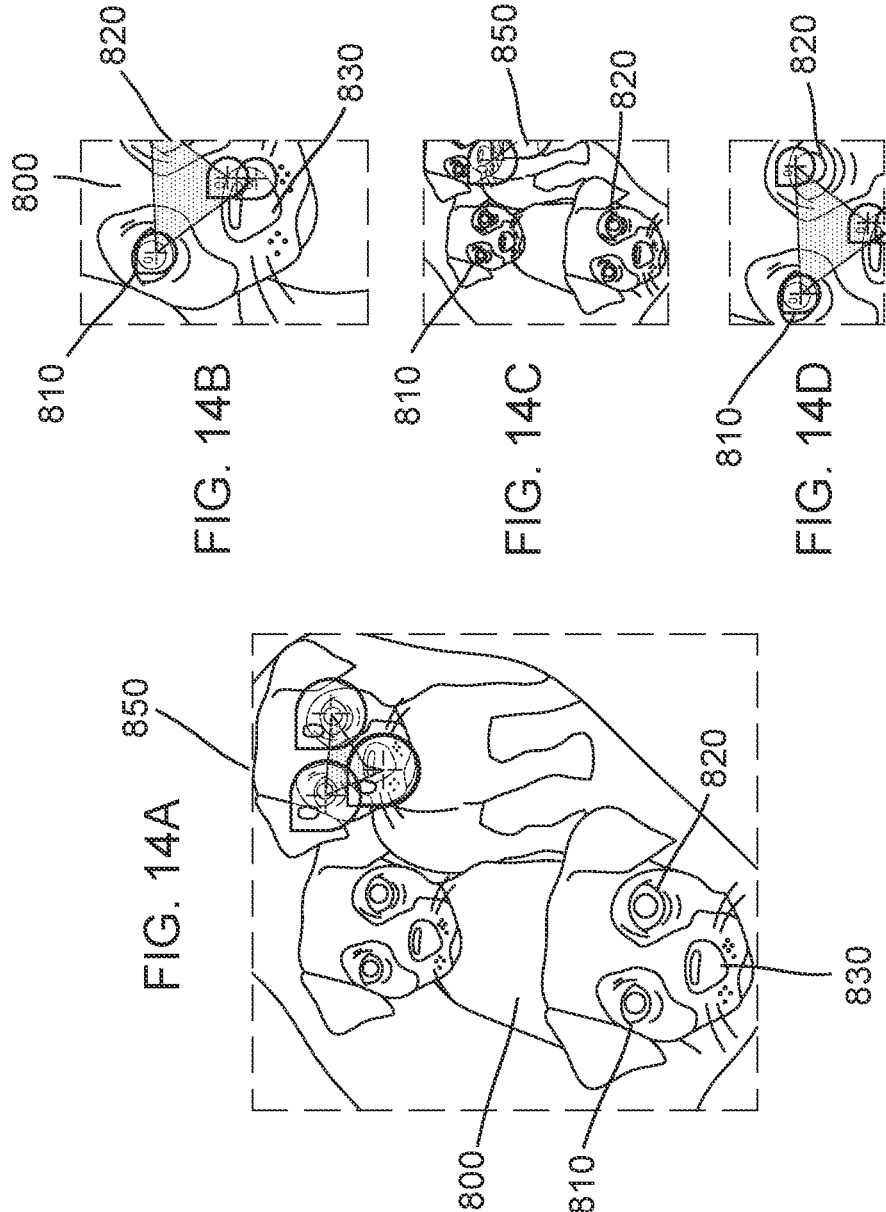
FIGS. 14A-14D illustrate an image of multiple small dogs for analysis.

FIG. 9 illustrates conceptually in steps 500 various types of input feeding into a process, which then creates an output.

FIGS. 10-14 illustrate an approach for processing images. FIGS. 10A-10D (collectively FIG. 10) illustrate steps in a deep learning system. Steps include classifying an image and/or a portion thereof 600. Individual features of interest are located 610. The located features are analyzed 620. Finally, aspects of the image are read 630. These steps are further explained on the website of Cognex Corporation at www.cognex.com, generally.

FIGS. 11-14 illustrate aspects of differentiating between similar images, such as distinguishing between blueberry muffins and small dogs. The exterior of the muffins includes portions of spherical blueberries, while the dogs have eyes. The blueberries and eyes are similar in appearance, creating a challenge for a machine vision processing system. Considering FIGS. 11A-11D (collectively FIG. 11), a blueberry muffin has a plurality of blueberries appearing on the surface of the muffin 700. In one approach as described generally in FIG. 10, locations of blueberries 710 are identified as with marker 720. The images are processed with a deep learning algorithm to identify the blueberries as blueberries, as opposed to some other object. This approach can be extended to focus on blueberries on one muffin 700 among a group of muffins 730, for example as shown in FIGS. 12A-12D.

FIGS. 13A-13D (collectively FIG. 13) and FIGS. 14A-14D (collectively FIG. 14) illustrate potential complexity of machine vision, in which eyes 810 and 820 and nose 830 of a dog 800 are to be distinguished from a blueberry muffin. As can be seen, the eyes and nose of the dog appear somewhat similar to blueberries on the surface of a blueberry muffin. And, in a group of dogs 850 (FIG. 14), features of the group may appear similar to a set of blueberry muffins. This problem of distinguishing features from among similarly appearing but different objects has been solved by the inventor using the aforementioned Cognex VisionPro ViDi Red and Green tools, in conjunction with properly populated databases.

Concerning the display screen, in the cup embodiment the read-out screen typically covers many kinds of inputs. The "top" of the mug (where you'd see the "drink") may have icons that grey out if not being used. For those functions currently in use, there are numbers displaying in real time for critical functions. The menu/settings icon can allow you to scroll through a potentially infinitely long list of items to choose from for display and/or calculations to support the numbers, plots, and images being displayed. You can also project an image on to a wall for showing the patient and/or allowing for more solution. An example may be found at: https://www.amazon.com/Magnasonic-Rechargeable-Hi-Resolution-Presentations-PP60/dp/B016N98GG6

In one embodiment, the screen is round and sits inside of the mug "top." As examples of screens, see https://www.e-bay.com/itm/193153771375 and https://www.ebay.com/i/264191240944.

In one embodiment, the user chooses options around a ring, then scroll choices. The screen can be used not unlike a compass to help orient for better data "fill in" for higher resolution, if desired. The mug may haptically vibrate to help the user tilt with better accuracy. https://www.ebay.com/i/264191240944

Concerning protection from the surrounding environment, one embodiment protects the interior components from heat, desiccation, wear and tear and cleaning. Through the use of seals and/or other means, the unit may be made waterproof. This is optional for some office and home environments in which water is not typically a hazard. But for many uses, waterproofing is desirable. In an emergency, for example, there may be bodily fluids and/or in an unclean environment. The entire unit also needs to be able to absorb/compensate for drops, for instance. The device needs to at least be able to withstand what a human subject can withstand, even if under uncomfortable conditions of extreme temperature, humidity, vibration, acceleration, deceleration, etc One approach to cleaning the device is ultrasonic cleaning. All connectors will be encased in the appropriate enclosures to allow this, with just the pins and circumference exposed for interaction with cabling. http://www.budind.com/blog/2014/02/the-mysteries-of-ip-rated-enclosures-ex-plained/

The mug should disassemble in a manner not unlike a Mag flashlight when changing the batteries. Swappable parts should be clearly marked for proper orientation and insertion with a lot of poke yoke (idiot proofing).

The primary intent of this device is to remain portable, but with numerous alterative configurations, able to communicate with and share data with other mugs. Many sensors and actuators can have multiple levels of durability and resolution. Usually, instrument grade versions are not as durable.

Regarding portability, some embodiments of the present invention may be used in various environments, beyond monitoring animals and/or humans. For example, the device may have multiple modes. One mode may be for studying an individual, another mode may be for diagnosing an issue with a machine or vehicle, another mode may be for sensing and processing natural phenomenon such as diagnosing the health of a tree. Many variations are possible. In each case, a portable unit in which are housed one or more sensors, gathers data, has the data processed externally and/or internally as previously described, and results displayed. In some environments, connecting with a network is impractical. Consequently, the device may include onboard memory sufficient to store collected data and/or a removable data card, USB flash drive, or other data storage unit, for later processing.

The device may be adapted to be a medical device for delivering medication. A variety of medications may be delivered to a patient. Jet injection is a preferred mode, via the bottom and/or handle of the "mug," depending upon where you need to inject. An alternative is to use a needle, although a needle may be more complicated to use than jet injection in this context. As an alternative to injecting medication, the device may be adapted to insert piezo electric meshes. Mesh can be inserted with a catheter needle.

In one medical device embodiment, an anti-blood clotting medicine can be administered from a device that can also defibrillate and produce ultrasound. Defibrillators known in the art are small already enough to be implantable: https://en.wikipedia.org/wiki/Implantable_cardioverter-defibrilla-tor. Known jet injectors are small enough: https://en.wiki-pedia.org/wiki/Jet_injector. See, also, https://www.healthline.com/health/type-2-diabetes/insulin-jet-injectors#use and, for jet injectors for anti-coagulation: https://www.qegateshead.nhs.uk/sites/default/files/users/user53/gynaconcology/IL426%20Subcutancous%20Self%20injection%20for%20anti-coagulation%20treatment.pdf The device may include accessories, such as for applying energy, ultrasound, injecting or applying medication, and the like. For example, the cup-shaped device may have detach-able elements, such as a wand for targeting an area for Transcutaneous Electrical Nerve Stimulation (TENS), defi-brillation, or a way to focus a light beam on a certain area of the body or into the cyc. Similarly, the device may communicate with and/or control external devices, such medical devices, 3D printers, musical instruments, sound, lighting, temperature-control devices, game gloves, body suits, and other types of external devices appropriate for a particular application. Methods of communication with external devices are known in the art.

Further, in another embodiment, a hand-held device reso-nates certain substructures of the body. It is often unneces-sary to heat the entire body. See, for example, descriptions of magnetic resonance imaging (MRI), such as at https://en.wikipedia.org/wiki/Physics_of_magnetic_resonance_im-aging and https://en.wikipedia.org/wiki/Functional_mag-netic_resonance_imaging It is noted that in resonating substructures of the body, signals are frequently corrupted by noise from various sources; hence, statistical procedures are used to extract the underlying signal. Sensor fusion, and changes in orientation of the mug(s), can help identify and directly filter out the noise. Noise is that part of the signal which you haven't taken the time to model yet.

That said, microwave ovens can cook at 2.4 GHz at high power. At lower power, we call it Wi-Fi, and Wi-Fi can differentiate objects inside of buildings, with drones outdoors using Wi-Fi. Bluetooth is usually 2.4 GHz right against our heads, but it really doesn't have enough power to penetrate the skin. In between, we could heat up certain target organs. Sec, e.g., https://wade4wireless.com/2014/02/01/rf-exposure-to-humans-and-much-more/.

In one approach, a particular organ that resonates at a particular frequency may be stimulated by resonating a seat haptically, via stimulation from the mug or in conjunction with a simple unbalanced motor. For more on whole body vibration, please see https://en.wikipedia.org/wiki/Whole_body_vibration A device according to the present invention may resonate across several frequencies to see how various structures respond, in a similar way.

The present invention may include using sound to move objects. The device may include a piezoelectric crystal speaker. For background on moving things with sound, see https://www.youtube.com/watch?v=L5fVFA2sWt4. For background on making a piezoelectric crystal speaker, see https://www.youtube.com/watch?v=R7zjfaPKMSE.

Figure 15:
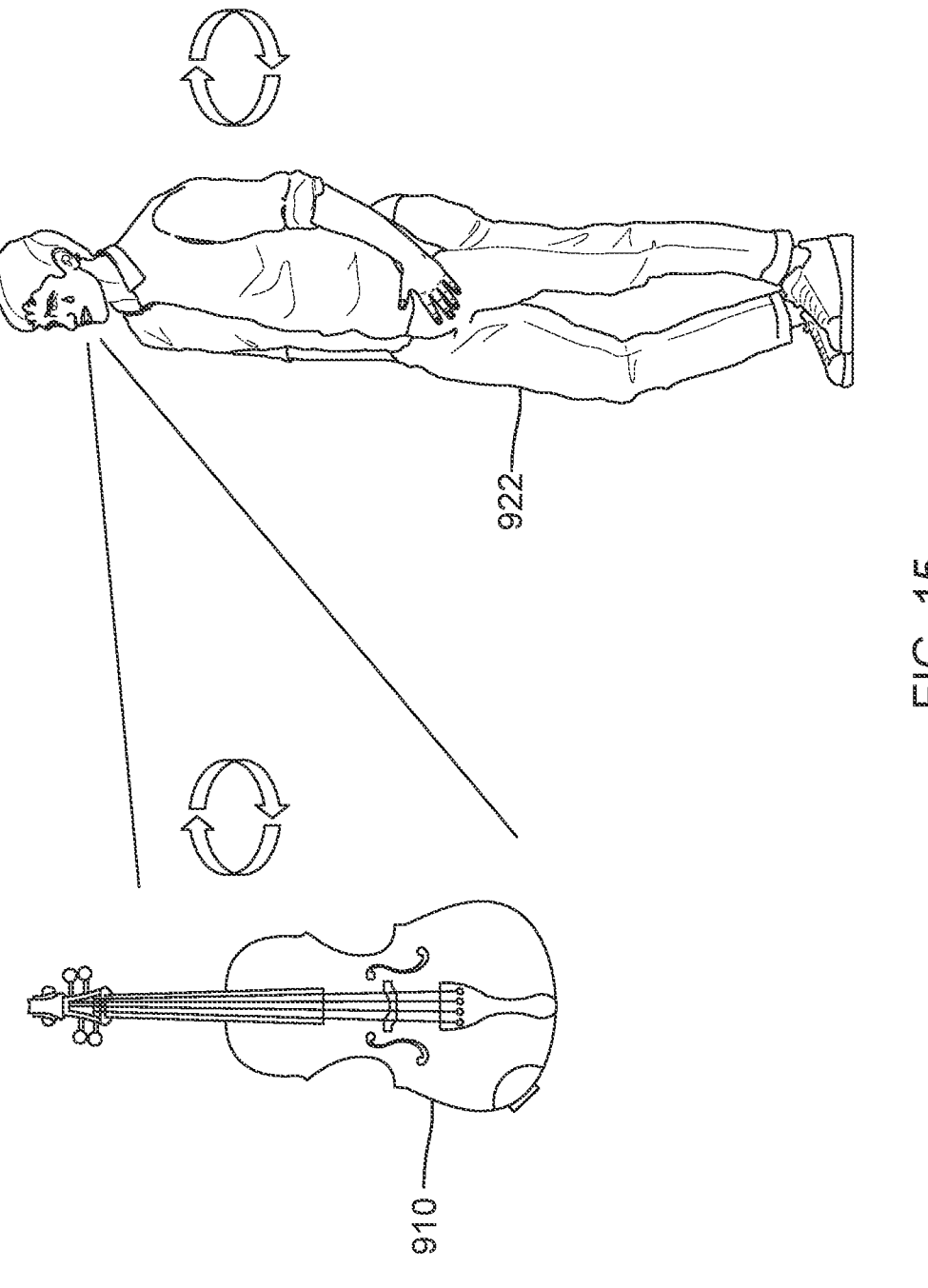
FIG. 15 illustrates a sensor device shaped as a violin, which senses aspects of a person in front of the sensor device.

Turning now to FIG. 15, a sensing device 910 is configured as a violin or other musical instrument. The device 910 is an assessment device that identifies and modifies physiological responses of a subject 922 in response to stimuli. For example, an assessment device, such as a musical modulation optimizer (herein referred to as "MMO") can identify and modify physiological responses in response to musical stimuli. The physiological response may be one or more of heart rate, blood pressure, pupil diameter, facial expression, tearing up, swaying to music, change in seating position, etc. A processing tool can determine whether physiological responses indicate psychological or emotional states in response to musical stimuli. The processing tool may employ an AI system and the processing tool may be presented herein by way of example to a trainable AI system; however, one will appreciate that a more generic processing tool may be substituted for the AI system mentioned anywhere within this description.

The device might also, or alternatively, identify and modify psychological or emotional states include sorrow, joy, arousal, confusion, etc. An AI system employs a neural network to determine whether physiological responses indicate psychological or emotional states in response to musical stimuli.

By way of overview, MMO can take feedback from:

1. Devices as generally described in previous sections: Human/animal/plant/machine measured/changes/locations/resonances between various independent sources of: overall body and/or internal organ/structure size, temperature, moisture, heart rate, respiration, chemistry, emissions, color 2. Entire organism's movements, nervous jitter/tapping, swaying, dancing frequency, sounds they make, independently—and in interaction with others (other living beings or machines, and of course its interactions with the MMO itself)

3. Other MMO-type devices

4. Other MMO-type devices

5. Other devices in communication with the MMO device MMO can actively:

1. Play music, both melody by hand from the human, and melody and/or harmony generated like a player-piano-violin and/or completely synthesized notes and/or prerecorded music/singing—continuous/sampled . . . .

2. Speed up and/or slow down the sounds to encourage a stronger resonant response from the Human/animal/plant/machine (entity) of interest. Methods of modulating frequency are well known. https://www.youtube.com/watch?v=V-Cj07Afzrw and https://www.youtube.com/watch?v=ZgMaBBwcl_4.

Considering the MMO concept broadly, music can have a profound effect on a human, even triggering intense emotional responses. There are many documented instances of music—sometimes in conjunction with video or other media—inducing crying in viewers. For example, a scene in a television show might have music composed to trigger an emotional response, in conjunction with a visual theme that also tends to elicit feelings in the viewer. An example is a scene in which a baby lies near a dying mother as music plays. Sec, e.g., https://youtu.be/6M9SaBbut8A Even a video of a horse dancing to music in a freestyle competition can elicit an emotional response in a viewer. Sec, e.g., https://youtu.be/zKQgTiqhPbw Turning again to FIG. 15, a violin 910 is provided having a variety of sensors, microphones, actuators, and/or other devices including lighting devices and/or lasers. Optionally, an initial prototype may be created using 3D printing and tested. If the device fails, the design may be altered, and a new prototype printed. Once tests on a prototype are successful, a wooden version may be created.

In one embodiment, sensors in the violin have a push button that adds a concert accompaniment from an onboard music synthesizer-type device, which triggers various natural frequencies. The system continues this until images show the customer starting to respond favorably. Examples of favorable response can be facial expression, tearing up, swaying to music, crying, changing seating position, or other physiological responses. Recurrent and radial basis function neural networks interpolate the ideal natural frequency to trigger desired reactions in the customer.

Conversely, if desired, the system can cycle through a pattern of frequencies until it detects a negative reaction in the user, such as frowning, pursing the face in anger, nervousness, shifting about in a seat, pacing, or the like.

The device can be operable to manipulate, such as enhance or diminish, a natural response to the musical stimuli, as music can be readily manipulated to resonate with a person's natural frequencies, such as for crying, joy, or pleasure. As an alternative to music, the device may play binaural beat patterns and observe user response to a particular binaural beat. This is consistent with the intent of binaural beat compositions, intending to elicit sleepiness, relaxation, concentration, energy, or other states, as desired. However, not everyone responds to music, sounds, binaural beats, and the like in the same way. Consequently, the present system may monitor the listener for face reactions, body language, and other factors to indicate if the music and/or other stimulation is triggering the desired effect.

William Pielemeier used seat vibration to determine human resonant modes, so he could design a seat that didn't excite those modes. See "A high-resolution time-frequency representation for musical instrument signals," *The Journal of the Acoustical Society of America* 99, 2382 (1996). This article is herein incorporated by reference. The article may be found at https://asa.scitation.org/doi/10.1121/1.415426. See also U.S. Pat. No. 5,618,995, which is herein incorporated by reference.

One embodiment of the present invention is a system and method for exciting those modes in the human eardrum and other organs. In one embodiment, a device such as a violin or mandolin can be adapted to be self-tuning. The device can serve as a demonstration tool to show that animals, such as people, can be precisely manipulated as electrochemical saltwater radios.

In one embodiment, the device may be shaped as a string instrument such as a violin and is made with 3D printing. One example of 3D printing a violin is disclosed at https:// contest.techbriefs.com/2016/entries/consumer-products/ 6678 and https://www.3d-varius.com. Sensors and electronics, such as those previously described, may be located within the violin.

In another embodiment, the scanning technology can be used to analyze the sounds and structure of a Stradivarius violin. The feedback can be used to make iterative 3D printed structures that sequentially are better at reproducing the sound. Additionally, an intelligent bow can be designed to achieve different sounds at different angles.

In another embodiment, a game glove or body suit can be provided to provide stimulus and feedback.

The invention encompasses not only a multi-sensor, but also multi-actuator: light, ultrasound, heat, and sound/music can all be manipulated to excite a resonance in the patient that can be used for diagnostics. The patient can also tell the examiner if the resonance results in emotional changes, pain, or pleasure.

Numerous variations on the foregoing concepts fall within the scope of the invention. In one embodiment, the device may direct various colors of light, ultrasound, and other active sensing devices toward the targeted patient, then measure the reflected signals.

The device may also passively sense parameters, such as temperature, and smells, and movement, both before the active sensors are engaged, and compares to how the patient's body reacts to the active sensors themselves.

In some embodiments, the device can communicate with other "modular" (swappable sensors) devices to broaden the data that can be compared to the database for one or more matches to known conditions. These other devices can have different sensors, or be duplicates, and can compare data while scanning the same patient, or another, who might be acting as a control, or a potential fellow victim of a malady.

The device may adaptively vary its active sensors to achieve a resonant mode in a given organ. This can aid in diagnosis and can also be used to mitigate pain by relieving tension and/or triggering the body's release of endorphins or other chemicals/hormones. The resonant mode of an organ is observed by the sensors (active or passive) tracking a change in the organ. This resonance can be motion based, chemistry based, odor based, or sound based, just to name a few possibilities.

In some embodiments, the devices described herein can detect and change one or more physiological responses and one or more emotional states of a test subject or person, and in some cases can be referred to as "physiological response and emotional state (PRES)" devices.

In one embodiment of the present approach, multiple organs can be observed and modulated at the same time. As one example, oximetry measurement of oxygen in the retina of the patient's eye may be measured and compared to behavior of an active sensor stimulated potential bleeding fibroid elsewhere in the body. The PRES device may also be employed to detect oxygen saturation in the retinal blood vessels to assess diabetic retinopathy, glaucoma, or a retinal vascular occlusion.

One embodiment of the present invention may be wired to, or wirelessly interact with, prosthetic devices to stimulate the patient externally, such as with a Fitbit wristband, an instrumented glove, or instrumented body suit. These prosthetic devices can also directly measure temperature, blood pressure, pulse, sweat chemistry, and odors directly.

Further, an ultrasonic sensor can display the interfaces between objects of differing density when touching the exterior of that object.

Considering other aspects of specific embodiments of the invention, one aspect of this disclosure relates to a portable scanning device useful for detecting medical conditions and/or personal threats such as surveillance devices or injury causing devices such as bombs. Moreover, the PRES device may be employed to detect physical objects on a person or animal and/or may be employed to diagnose mechanical systems using the stimulus emitters and the sensors. The trainable AI system may employ object recognition technology such as available in some checkout scanning systems; however, the PRES device may utilize more than optical data.

An aspect of this disclosure relates to a means to detect potentially life-threatening conditions that are normally detected via x-ray, but are often found in the abdomen, which tends to excessively absorb x-ray radiation. One specific application, that could fit into one of these modular units, is to detect and locate bleeding fibroids. They can be pulmonary (say, left chest), uterine (lower abdomen), or other places in the body of a human or animal (or possibly even a plant). There have been many cases of women in their 50's and 60's suddenly bleeding heavily internally. There are several ways to detect them without having to overdo x-rays as discussed herein and shown in FIG. 10. The PRES device may also locate a mass and differentiate it from normal tissue. For example, the PRES device utilizing the trainable AI system may differentiate an ovarian cyst from a normal follicle that is about to release an egg.

Another aspect of this disclosure relates to its modularity for handheld use, critical to remote geographical locations, scanning humans trapped in tight spaces, or for scanning unknown to the subject being scanned. One type of handheld packaging for the PRES device could employ a handheld tricorder medical device such as disclosed at http://www.t-ricorderproject.org/about.html (the text, the design and/or capabilities of which are herein incorporated by reference). There are seven patent applications that list one or more of Basil Harris, George Harris, Edward Helper, and Constantine Harris as an inventor in connection with a device referred to as DXTER™. These patent applications are incorporated herein by reference. One or more of the functionalities of the DXTER™ device as disclosed in these incorporated patents can be included in the portable assessment device.

In some embodiments, an example of a PRES device (e.g., mug or bowl) to detect tremors may be held or directly interacted with by the person. In some embodiments, an MMO may adjust someone's emotional state without them coming into direct contact with the MMO. In those cases, the MMO can be hidden, remote, integrated into a room stereo system, etc., but the MMO can still detect a physiological response for the feedback loop (e.g., have line of sight for a camera, be coupled to a separate device with a camera, receive feedback from sensors, etc.).

However, this disclosure also proposes a mug (or mug-shaped) type design because it is non-threatening to the subject, easy to hold by the user, and functionally suited to internal sensor and mirror rotation.

In some embodiments, one can vary the scanning via https://velodynelidar.com/newsroom/how-to-change-laser-angle-and-fov-vlp-16/ (the text, the design and/or capabilities of which are herein incorporated by reference). Moreover, U.S. Pat. Nos. 8,767,190; 9,983,297; 10,018,762; 10,048,374; and 10,197,669 are herein incorporated by reference. One or more of the functionalities of the scanning systems disclosed in these incorporated patents can be included in the portable assessment device.

The devices 10, 110, 410 herein (regardless of whether they are mug shaped, tricorder shaped, instrument shaped, or other shaped) may generically referred to as a PRES device. In general, a PRES device may passively collect data that it observes, may actively scan a patient without substantially changing the patient, directly stimulate with a laser or ultrasound to try to get a response, and gain enough information to potentially treat the patient right then and there, and potentially treat the patient. Moreover, a musical modulation optimizer MMO (herein referred to as an "MMO" or "MMO device"), which is a variation of a PRES device, may "entertain" the patient with music/other sound effects (and possibly fragrance) in order to calm the patient down for better data collection, change the states of a patient (emotional and/or organ vibration/resonance) to generate more data, gain enough information to potentially treat the patient right then and there, and potentially treat the patient. As later described in greater detail, a MMO device may have the ability to play music (or other sounds, signals or any type), then observe a change in the subject (human, animal, plant, machine), then modify its output in response. This process may be provided as a single application or as or a feedback loop until a certain response is achieved. The MMO device may for example initially observe restlessness and pain in an individual, but may end up observing calm and tranquility in the individual. The MMO device may resonate a target organ to make it easier to diagnose an issue, may observe a change of state (more stressed, lees stressed) in and of itself, and may provide the data points for additional analysis.

In some additional, alternative, or selectively cumulative embodiments, this Australian researcher's work can be incorporated into this device. If the magnetic resonance can be focused, there can be less of an impact on the subject. The PRES device may be operable to be hooked up temporarily to a larger device that would provide the means to accumulate enough energy to be effective. "We have a unique opportunity to utilize a new minimally invasive therapy for symptomatic uterine fibroids called Magnetic Resonance guided Focused Ultrasound (MRgFUS) for fibroid-related research." https://www.thewomens.org.au/research/research-centres/womens-gynaecology-research-centre/research-themes/wgrc-abnormal-bleeding-uterine-fibroids (the text, the design and/or capabilities of which are herein incorporated by reference). For example, the technology employed in the ExAblate 2000 (InSightec Ltd., Haifa, Israel) combines magnetic resonance imaging (MRI) with high-intensity focused ultrasound to destroy tumors non-invasively. U.S. Pat. Nos. 9,623,266, 9,814,909, 9,852,727, 9,934,570, and 9,981,148 are herein incorporated by reference. This Magnetic Resonance guided Focused Ultrasound (MRgFUS) technology can be adapted to be employed in and/or with the portable assessment device.

This Ted talk describes the colored regular light that can be used by the PRES device to locate tumors. https://www.ted.com/talks/mary_lou_jepsen_how_we_can_use_light_to_see_deep_inside_our_bodies_and_brains/transcript?language=en (the presentation, the design and/or capabilities presented therein are herein incorporated by reference).

Another application involves a blue laser aimed into an eyeball to detect heavy internal bleeding. The machine Mark J Rosen (Pulmonary Medicine, Mount Sinai Doctors Faculty Practice, 36 West 60th Street, New York, NY 10023) is evaluating currently costs $500K, but if you turn the power down on this Keyence parts inspection laser, with its own control board, so you don't hurt the eye, and you have the same functionality in a small package, and quite affordably. https://www.keyence.com/products/measure/index.jsp (the text, the design and/or capabilities of which are herein incorporated by reference).

The "Retinal oximeter" was first developed in 2002 by Chris Gregory. https://www.newscientist.com/article/dn2363-look-in-the-eye-reveals-internal-bleeding (the text, the design and/or capabilities of which are herein incorporated by reference). http://eyewiki.aao.org/Retinal_Oximetry (the text, the design and/or capabilities of which are herein incorporated by reference). In conjunction with this disclosure, the hardware of this technology can be used to scan older women at high risk for bleeding fibroids.

Older women are not the only patients that will benefit. Coal miners are dying from black lung, from the quartz dust in the coal mines. They often suffer from https://pulmonary-fibrosisnews.com/2017/05/25/twelve-facts-about-pulmonary-fibrosis-prognosis-and-life-expectancy/2/ (the text of which is herein incorporated by reference).

Brain and other tumors are excellent to scan frequently for changes after a surgery might not have eliminated all cells. These tumors can regrow and cause issues as early as 6 months to as late as a decade later. https://www.nbc4i.com/news/u-s-world/an-8-year-old-boy-celebrates-after-beating-stage-4-brain-cancer/1632910704 (the text of which is herein incorporated by reference).

These scanning devices can also be used as tools to ameliorate disease. For example, a PRES ultrasound scanner can be used to treat Alzheimer's disease. Sec https://www.wvnews.com/statejournal/news/historic-breakthrough-wvu-rockefeller-neuroscience-team-first-to-use-ultrasound/article_b9951ba2-19ba-54ba-8e1c-0096fb4824bc.html Ultrasound technology can be packaged into handheld devices. For commercially available handheld ultrasound devices, see https://www.bing.com/shop?q=handheld+ultrasound+devices&FORM=SHOPPA&originIGUID=E018626F2D6B4C4B98E5335F6F8F51BA The PRES device can be also packaged to include defibrillator technology. For commercially available handheld defibrillator technology, see https://www.amazon.com/HeartStart-861284-Philips-Home-Defibrillator/dp/B00064CED6 The PRES device can also be packaged to include "TENS" technology. For commercially available handheld "tens" technology see https://www.bing.com/shop?q=handheld+tens+unit&qs=n&form=SHOPSB&sp=-1&pq=handheld+tens+unit&sc=0-18&sk=&cvid=5E57EA01AEB34F4EAF0E946E67363840

If someone is getting cold from poor circulation, you could actually warm them up via localized resonance activity. If you cause someone to resonate, their body temperature will almost always go up. Infrared sensors can actually warm you up if you continue to use them a long time. Of course, you want to monitor so they don't get too hot. Also, human body movement can also recharge a PRES device worn on the person.

These scanning devices can also be used to scan and resonate inanimate objects and mechanisms, similarly to the way they can scan living things. For example, the scanning devices can utilize Flir™-like technology to identify hazards, such as gas leaks, or even occluded objects, such as pipes or wiring behind walls in the context of remodeling projects. See for example, "No, really. You can see through using walls drones and Wi-Fi" https://www.theregister-.co.uk/2017/06/20/drones_and_Wi-Fi_see_thru_walls/ and U.S. Pat. Nos. 5,345,304 and 8,659,664, which are incorporated herein by reference.

These different scanning technologies (emitters and sensors) can be packaged together in arrangements that optimize their performance. They can share power supply, master controller, communications nexus, and external connections to external devices, power cords, Ethernet, etc. They can also be constructed as modular add-ons that are adapted to connect in a specific manner so as to functionally integrate with any needed internal systems.

The PRES scanners should be carefully calibrated to avoid wave interference that could cause extreme amplitude issues in eardrums, organs, music, heat, hormones, etc. See https://en.wikipedia.org/wiki/Wave_interference. The AI system can be utilized to assist with identification of off-calibration and correction thereof.

Considering other potential aspects of a PRES device, the be paired off with an ultrasound probe like this: https://www.fastcompany.com/1725155/ultrasound-scans-your-baby-now-available-smartphone. PRES devices can combine this with Wi-Fi to scan for objects inside of the human body that vary in density, from foreign objects (swallowed object/bullets) to possibly cancerous/fibroid growths of different density if the Wi-Fi is tuned properly and in conjunction with/trained by ultrasound. https://www.youtube.com/watch?v=fGZzNZnYIHo. In some instances, Wi-Fi can be used to see through walls. PRES devices can use a 40 Hz oscillator to stimulate peoples' brains to stop/reverse Alzheimer's. https://www.mayoclinic.org/diseases-conditions/alzheimers-disease/expert-answers/music-and-alzheimers/faq-20058173 and https://gammalighttherapy.com/collections/40 hz-light-devices/products/gamma-40-hz-light-therapy-kit One goal of select embodiments of the PRES devices is to use cheaper, more robust, readily available, easy to replace, simple variations of current medical technology to achieve the same results. https://store.synthrotek.com/555_Timer_Oscillator_Kit In some embodiments, PRES devices can vary the colors used to diagnose, based on brain resonance, what parts of the brain are responding to varying degrees to the 40 Hz. PRES devices can also oscillate other actuators (not just light) to vibrate at 40 Hz (or other frequencies, as harmonics) to resonate other organs/muscles/nerves/skin/bones to stimulate healing (we do this with ultrasound and STEMS now). PRES devices can vary at other frequencies.

PRES devices may have modular plug and play attachments that will automatically recognize each other and activate sensor fusion (using neural networks) software to co-locate and co-target the same tissues/tumor/cut/tendon pull and work in synchrony (same time as resonance, or alternating their effects—one to aid secretion, the other to resonate to better absorb the hormone just secreted).

These devices (paired up in one handheld, or two working in synchrony) can not only play music to help Alzheimer's patients (or any other mental condition with brain function issues/damage) not only find an alternate path to information (music is stored in multiple parts of your brain, and accessing one memory can stimulate other memories near it)—but PRES devices can pinpoint where the activity is, and resonate it to trigger even more response. It can also direct hormones/drugs to act in that location by vibrating at a frequency that triggers the hormone/medication to activate/combine at that spot.

Some embodiments of a PRES device can help Down's Syndrome patients better transfer short term to log term memory (their major issue—and why we try to push as much info into them when they are very young near 3 years old, when it's still easiest to help them retain information). PRES devices can help locate where to inject stem cells, and then stimulate stem cells to stay where they are and start dividing in a specific spot (brain, damaged parts of the body, including thinning walls of an artery).

Some embodiments of a PRES device can be used to slow internal bleeding at the scene of an accident—inject the clotting drug directly into the area (chest) and then stimulate it to act. This can be a blood clot and it can also be the unfolding and wrapping of a piezo electric mesh that was just injected into the body. This mesh can not only be metal to bend with electrical zapping optionally from the large power source/battery that comes with the defibrillator, it can also be applied around a tiny clot cloth that was injected via catheter needle that swells up once inside the body (blood itself!) https://www.ebay.com/i/163764749516.

Some embodiments of PRES devices can be used to look at arterial damage progression just before and just after CPR/defibrillator application, and then move to mitigate holes that broke open from shocking near the clot that caused the heart attack stroke to begin with. https://www.osha.gov/Publications/3185.html Considering further background, concepts utilized in driving neural network patents and later lane departure warning patents by Dean Pomerleau can be adapted for use with the portable assessment device: images fed into a neural network; hidden units are mini images that can be reused elsewhere to cross correlate mini features to determine if feature is a lane, another vehicle, etc.; original neural network's output was a steering vector; mixture of experts chose what actual steering command to actually deploy; and from the outputs of competing neural networks tuned to various driving surfaces. U.S. Pat. Nos. 5,448,484, 5,091, 780 are herein incorporated by reference.

Analyzing images for details is also disclosed in http://www.tricorderproject.org/papers/jansen_fiacconi_gibson_2010_neonate_saccades.pdf, which is herein incorporated by reference.

One will appreciate that many forms of artificial intelligence (AI) can be used instead of, or in addition to a neural network (which is for convenience in this disclosure is considered to be a specific form of AI). These might include probabilistic techniques such as Bayes or Markov algorithms, kernel methods (like SVM, decision trees/random forest, Gaussians, PCA . . . ), reinforcement learning that can have nothing to do with artificial neural networks, artificial reasoning a.k.a. "good old fashioned AI," many path-planning and intelligent control-systems methods that correspond to "classical AI" (not the same as GOFAI), Alife (swarms, cellular automata . . . ), agents and chaos systems, and/or any algorithm or group of algorithms that optimize a value function (reinforcement learning and linear dynamic programming).

The PRES device may include a communication nexus between the sensors and the AI processing tools. Some or all of these AI processing tools may be positioned within the PRES device itself, such as in an "onboard" computer, and/or in communication with a master controller. One will appreciate that the communication nexus may also use or rely on a wired or wireless connection to nearby or offsite AI processing tools.

Selectively cumulative embodiments are embodiments that include any combination of multiple embodiments that are not mutually exclusive.

Additional aspects and advantages will be apparent from the following detailed description of example embodiments, which proceeds with reference to the accompanying drawings.

Some embodiments do not use CAT SCAN x-rays or MRI MAGNETIC imaging, as these are both risky for some individuals even once, and for all individuals, multiple times. Medical personnel can then determine if these machines are necessary after examining diagnostic results from the device and system.

The techniques described herein relate to systems and methods for the detection of one or more physiological responses in a person. The systems and methods described herein include those for detecting physiological responses such as tremors (e.g., in people with dementia or Parkinson's disease), temperature (e.g., using an IR camera, a thermometer, or a thermocouple), and/or grip attributes (e.g., grip intensity, a grip consistency, or grip balance).

In some embodiments, the physiological response detection systems described herein include a device with one or more sensors and a communication nexus, and optionally other systems (e.g., cloud-based systems, mobile devices, tablets, and/or computers) in communication with the device. For example, the device can be a cup, mug, or bowl, with a receptacle for holding a consumable (e.g., food, drink, and/or medication), and include a gripping area for the device to be held by a person. The device can include sensors, such as accelerometers, cameras, and/or gyroscopes, that can be used to detect physiological responses, such as tremors, in a person while they are holding the device using the gripping area. Optionally, the gripping area can also include sensors, for example, load cells or pressure sensors to detect grip attributes, and/or a thermocouple or thermometer to detect a temperature of the person. The sensors in the gripping area can also include a heart rate monitor, in some cases. The consumables receptacle can also include one or more sensors, for example, camera(s), thermometer(s), liquid level sensors, and/or load cell(s) that can be used to determine the presence of a consumable in the consumable receptacle.

In some embodiments, the sensors of the systems described herein can provide information or data to a processor, which can save the data to memory coupled to the processor. The processor can translate the information or data into a physiological response for a test subject or person using an AI model or algorithm. The processor can determine an emotional state or operational state of a test subject or person from one or more physiological responses using an additional AI model or algorithm.

In some embodiments, one or more stimuli (e.g., ambient sounds, ambient temperature, or the temperature of a gripping area of a device) are used to change one or more physiological responses and one or more emotional states of a test subject or person. An initial measurement of a physiological response of a person at an initial environmental condition can be made and the processor can determine an initial emotional state of a test subject or person from the initial physiological response. One or more stimuli can be changed or can change the environmental condition, and the physiological response of the person can be measured again to determine how the physiological response of the test subject or person changes in response to the one or more changed stimuli. The processor can also determine if a change in a physiological response indicates a change in an emotional state of the test subject or person. In some cases, the processor can use an AI model or algorithm to determine how to change the one or more stimuli in order to change a physiological response and/or an emotional state of the test subject or person. In some cases, a target physiological response is determined, and the processor can use an AI model or algorithm to determine how to change the one or more stimuli in order to change a physiological response of the test subject or person into the target physiological response. In some cases, a target emotional state is determined, and the processor can use an AI model or algorithm to determine how to change the one or more stimuli in order to change an emotional state of the test subject or person into the target emotional state.

Some examples of sensors that can be included in the systems and methods described herein include one or more temperature sensors, resistive temperature devices (RTDs) or thermistors, microphones, electrical measurements (e.g., electrical resistance, electric field strength, etc.), ambient air pressure, ambient humidity, piezoelectric microphone (to detect vibrations), photoresistor, camera, and a retinal oximeter.

Some examples of physiological responses that can be detected using the systems and methods described herein include body temperature, sounds generated by a person, electrical signals generated by a person, electrical signals generated by a device used by the person (e.g., a pacemaker), heart rate, blood pressure, pupil diameter, blood oxygen level, body sweat, anatomical information (e.g., from cameras or vibration sensors), the presence of one or more loose teeth, facial expression, eye expression, crying, tearing up, laughter, swaying to music, or a change in seating position in a person in proximity to the device, using the device, or holding the device. In some cases, the processor that may employ a model developed by an artificial intelligence (AI) system (e.g., a trainable AI system), or the processor can use other types of algorithms to determine a physiological response of a person using data from one or more sensors.

Some examples emotional states or operational states that can be detected using the systems and methods described herein include happiness, sadness, joy, sexual arousal or orgasm, pleasure, sleepiness, meditation, daydreaming, anger, displeasure, annoyance, pain, calmness, relaxedness, attentiveness, distractedness, etc. In some cases, the processor that may employ a model developed by an artificial intelligence (AI) system (e.g., a trainable AI system), or the processor can use other types of algorithms to determine an emotional state or operational state of a person using data from one or more sensors. In some cases, the information from the one or more sensors is translated into a physiological response and the emotional state or operational state is determined from the physiological response.

Some examples of stimuli that can be used to change the emotional states or operational states of a person using the systems and methods described herein include ambient temperature, ambient humidity, ambient sound (e.g., music, tones, binaural tones, beats, rhythms, etc.), the temperature of a gripping area of a device, images on a display (that is part of the system, or that is controlled by the system), haptic vibrations, ambient lighting, or an olfactory stimulus.

For example, an AI model can interpret data from one or more sensors of the systems described herein to determine if one or more of the emotional states are present or may be present, or to determine the likelihood that an emotional state is present. The processor can use a model, for example that is developed by an AI system that employs a neural network to translate data from one or more sensors into one or more physiological responses, and then determine whether the physiological response(s) indicate that an emotional state is present. The AI model may be trained on selected emotional states related to or based on one or more types of sensor feedback. For example, an AI model can be trained to determine the presence of laughter, which could indicate a happy or joyous emotional state. In this example, an audio sensor or microphone detects a signal, the processor translates the audio signal and detects the presence of a physiological response that is laughter. The processor then determines that the person laughing has a happy emotional state. In another example, an AI model can be trained to determine the presence of laughter crying, and also the presence of laughter. In this case, a camera detects images of a person's face, and the processor translates the images and detects the presence of a physiological response that is crying. The processor can also use information from the audio sensor or microphone to detects the presence of a second physiological response that is laughter. The AI model in this case can be trained to determine that the presence of crying in conjunction with laughter indicates that the person has a happy emotional state, while the presence of crying without laughter indicates that the person has a sad emotional state.

In some embodiments, the physiological response detection systems described herein additionally include a speaker that can be used to play music, and a processor that can control the speaker. As an alternative to music, the device may play binaural beat patterns and observe user physiological response to a particular binaural beat. For example, an assessment device, such as a musical modulation optimizer (as described herein) can identify and modify physiological responses in response to musical or binaural beat stimuli. For example, the physiological response may be one or more of heart rate, blood pressure, pupil diameter, facial expression, tearing up, swaying to music, change in seating position, etc. A processor of the device or in a second device in communication with the device can determine whether physiological responses indicate psychological or emotional states in response to musical or binaural beat stimuli. In some cases, the processor may employ a model developed by an artificial intelligence (AI) system (e.g., a trainable AI system), or other types of algorithms. The device might also, or alternatively, identify and modify psychological or emotional states including sorrow, joy, arousal, or confusion. A model can be used by the device, for example that is developed by an AI system that employs a neural network to determine whether physiological responses indicate psychological or emotional states in response to musical stimuli. The AI model may be trained on selected emotional states related to or based on one or more musical selections or binaural beat stimuli.

In some embodiments, the processor can be coupled to the one or more sensors and use one or more inputs from the sensors to determine one or more of the physiological responses of the person. The processor can cause the music to be adapted (i.e., change some musical aspect of the music, such as the volume, tempo, pitch, key, instrumentation, song, lyrics, etc.) to alter the physiological response of the person. As an alternative to music, the processor of the device may cause a speaker of the device to play one or more binaural beat patterns, receive one or more inputs indicating a physiological response of the person (i.e., detect the physiological response), and adapt the binaural beat patterns based on the detected physiological response. For example, the processor could initially receive a measured physiological response of a person (e.g., using one or more sensors) that indicates that the person is nervous or agitated or upset. Then the processor could cause a speaker to play music with different musical aspects or a binaural beat with different parameters and receive a second measured physiological response of the person. The musical aspects of the music or the parameters or the binaural beat patterns being played can be changed until the physiological response of the person exceeds a threshold, or a desired physiological response is achieved, that indicates that the person is in a particular emotional state (e.g., is sufficiently calm). Once the person is determined to be calm, the processor can also trigger one or more actions to occur, for example, a diagnostic test (e.g., a blood pressure measurement) can be performed. The processor can use models, such as those developed using recurrent neural networks and deep learning, and/or algorithms to determine a physiological response of a person from information detected by one or more of the sensors. The processor can also use models, such as those developed using recurrent neural networks and deep learning, and/or algorithms to determine what music to play and which musical aspects of the music to change to achieve a desired physiological response.

In some cases, an emotional state (or an operational state) of a person (or animal) can be determined from the physiological response and/or from information detected from the one or more sensors of the physiological response detection systems and methods described herein. The emotional state or operational state can be monitored, and the music can be adapted (or musical aspects of the music can be changed) with the goal of changing the emotional state or operational state of the person (or animal). The processor can use one or more models, such as those developed using recurrent neural networks and deep learning, and/or algorithms to determine what music to play (or which musical aspects of the music to change) based on the determined emotional state or operational state of the person (or animal).

In some cases, a diagnostic test (e.g., a blood pressure measurement), can be performed while a person (or animal, or patient) is in a first emotional state or operational state, and then it can be performed while the person is in a second emotional or operational state. The emotional or operational state can be determined using the physiological response detection systems and methods described herein. For example, a blood pressure measurement can be taken soon after a patient arrives at a care facility, and the physiological response detection systems described herein can be used to play adaptive music and monitor the emotional state (or an operational state) of a person (or animal) until it is within a range that triggers taking a second blood pressure measurement.

For example, a processor of the systems and methods described herein can determine an emotional state of a person and compare it with a reference emotional state, in order to determine what physiological response to expect from a person. If the determined emotional state is close to a reference emotional state (e.g., within a threshold), then the processor can determine that an expected physiological response at the determined emotional state should be approximately the same as those of a reference physiological response the reference emotional state. If the determined emotional state is different from the reference emotional state, then in some cases the processor can adjust an expected physiological response (e.g., based on historical data for a person) at the determined emotional state compared to the reference physiological response of the reference emotional state. For example, the physiological response can be blood pressure measurements. If the determined emotional state is different from the reference emotional state, then in some cases the processor can determine that the expected systolic and diastolic blood pressure measurement at the determined emotional state is to be adjusted (e.g., should be 10 lower on top and 5 lower on the bottom to an 85% degree of confidence) compared to those of the reference emotional state. In some cases, the determined emotional state cannot be too different from the reference physiological response of the reference emotional state for such adjustments to be determined.

The systems and methods described herein can be advantageous, to improve the accuracy of diagnostic tests. For example, a blood pressure or pulse rate measurement can vary greatly depending on the emotional state or operational state of a person. For example, a person coming out of a stressful situation (e.g., a meeting with their boss) could have a blood pressure as high as 240/80, while a resting blood pressure for the same person could be 90/60. The systems and methods described herein can be used to monitor the physiological response of a person, determine an emotional state or operational state of the person based on the monitored physiological response, and cause music to be played to change the emotional state or operational state of the person in order to obtain improved accuracy for diagnostics tests such as blood pressure or pulse rate measurements.

In some embodiments, the device of the systems and methods described herein can include one or more IR cameras mounted on a gimbal (as described herein) such that the camera can rotate and zoom in on a person's head, face, or forehead to measure their temperature. If the person has tremors (e.g., from Parkinson's disease or dementia), then the captured images (or video) can be smoothed to aid the analysis. The gimbal base can be auto-tracking, in some cases, to track the movement of the person's head, face, or forehead relative to the device. The device can also include other sensors which may be in separate locations within or on the device (e.g., a pressure sensor or thermometer in a gripping area, or a sensor to detect the presence of a consumable in a consumable receptacle), or the additional sensors (e.g., an accelerometer, gyroscope, pressure sensor) can be co-located with the IR camera. In some cases, an IR camera can measure blood vessel dilation inside of the person's eye to determine a physiological response and that physiological response can be used to determine an emotional state or operational state of a person.

In some cases, the systems and methods described herein can trigger an action, an alarm, or an alert, once a physiological response, or emotional state or operational state of a person is reached or determined. For example, the systems and methods described herein can detect a physiological response or emotional state or operational state of a person, and trigger an alert, for example an electronic alert (e.g., sending a text or email), or playing an audible alert using a speaker. The alert could be sent to a doctor, a caregiver, and/or the person. For example, an alert could be sent that a dose of medication is needed based on the physiological response or emotional state or operational state of the person. The physiological response could be, for example, a number, frequency, or severity of tremors exceeding a threshold, and the medication can be magnesium, in one example. In another example, the systems and methods described herein can detect a physiological response or emotional state or operational state of a person, and trigger an action, such as dispensing medication into the consumable receptacle, playing different music, or changing a musical aspect of the music. In another example, the systems and methods described herein can detect a physiological response or emotional state or operational state of a person, and trigger an alarm, such as an audible alarm.

In some cases, the systems and methods described herein use models, such as recurrent neural networks and deep learning, and/or algorithms to do prognostics, for example, to determine an emotional state or operational state from a physiological response.

Figure 16A:
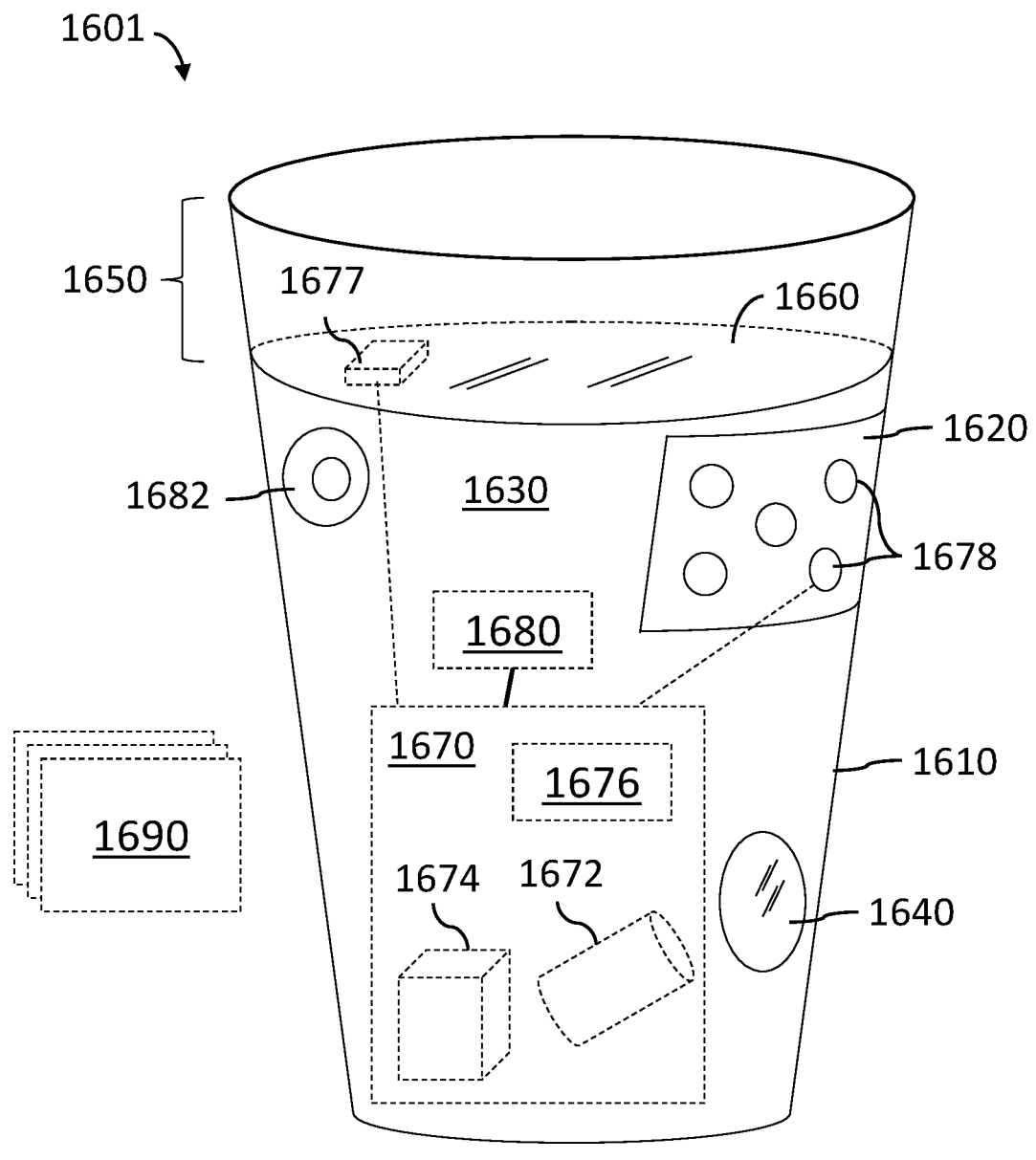
FIGS. 16A and 16B show schematics of examples of systems for detecting a tremor in a person, in accordance with some embodiments.
Figure 16B:
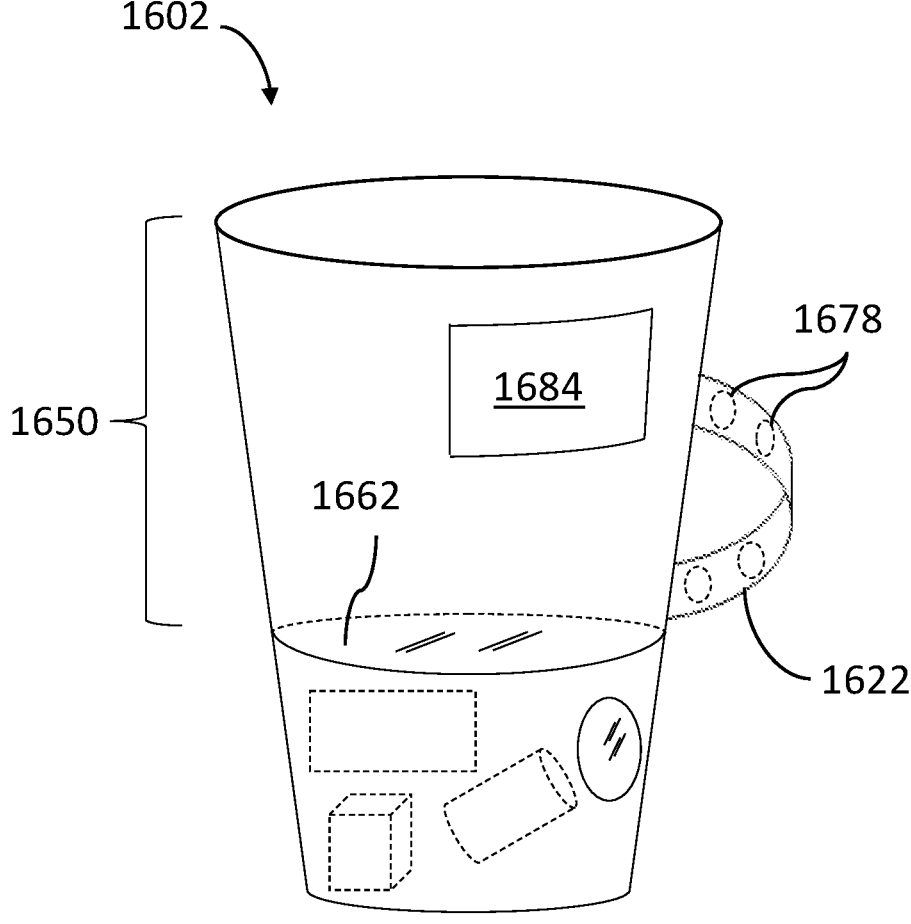

FIGS. 16A and 16B show schematics of example systems for detecting a physiological response, such as a tremor or heart rate, and an emotional or operational state, such as joy or distractedness, in a test subject or a person, in accordance with some embodiments.

FIG. 16C is a table that includes categories of measurements that can be made using the systems and methods described herein (e.g., those in FIGS. 16A and 16B), the environment in which such measurements can be made, examples of types of sensors that can be used for the measurements, and the physiological response of the test subject or person being measured. For example, in the temperature category, a temperature of the ambient environment is measured using one or more sensors, which can be a resistive temperature device (RTD) or thermistor, and the body temperature of the test subject is the physiological response that is measured. In the audio category, ambient sounds are measured from the environment using microphones to detect sounds produced by the person (e.g., vocal sounds, wheezing, voice commands to control the device). There are many measurements possible in the electrical category, for example, static electrical field strength, or electrical resistance can be measured to provide information about various physiological responses, such as skin conductivity. In the pressure category, ambient air pressure can be measured using a pressure sensor in the vicinity of a person to determine their heart rate. In the humidity category, humidity sensors can be used to detect an amount of body sweat of a person. In the vibration category, piezoelectric microphones can be used to determine anatomical information about a person (e.g., their joints due to vibrations caused while walking). In the motion category, an accelerometer, gyroscope and/or camera(s) of a device being held can be used to measure a level of tremors in a person, or if they are moving or swaying to music.

There are two optical categories shown in the table in FIG. 16C, one for detecting ambient light intensity or images, and one for ambient light color (e.g., by taking a spectrum), both of which can detect light with wavelengths in the visible or IR ranges. In the category for light intensity, a photoresistor or photodetector can detect blood oxygen level of a person. In the category for light imaging, a visible and/or IR camera can detect images of a person, and determine their temperature, tremors, facial expressions, if they are crying, if they are laughing, if they are swaying to music, etc.

The physiological responses determined in the categories in the table in FIG. 16C can be used to determine an emotional state or operational state of a person using the systems and methods described herein.

FIG. 16A shows a schematic of an example of a system 1601 for detecting a physiological response, such as a tremor, in a person, in accordance with some embodiments. The system 1601 includes a device with a housing 1610 comprising a gripping area 1620 and an exterior wall portion 1630 separating an interior of the housing from an exterior of the housing. In some embodiments, the exterior wall portion 1630 includes a material 1640 that is opaque or reflective when viewed from the exterior of the housing but is translucent or transparent when viewed from the interior of the housing. In some cases, the gripping area 1620 includes one or more textured pads that slightly protrude from or are substantially flush with the housing. The gripping area 1620 can be located anywhere on the housing 1610 (e.g., handle, an exterior of the housing, a rim of a mug or bowl, etc.), and can be larger or smaller than the gripping area 1620 shown in FIG. 16A. For example, gripping area 1620 can wrap around the entire device 1601 in some embodiments. The housing 1610 can be made entirely of material 1640, or some portions of housing 1610 can be made from material 1640 and some portions from a different material (e.g., that is opaque, or translucent, or that is not transparent from either direction). One or more portions of housing 1610, for example a gripping area 1620, may be made of or comprise a piezoelectric adaptive mesh to sense contact areas, as described in U.S. Pat. No. 11,818,956, filed Apr. 1, 2020 and issued Nov. 14, 2023, the contents of which is herein incorporated by reference in its entirety.

System 1601 of FIG. 16A also includes a receptacle 1650 for a consumable, for example, food, or drink, or medication. The receptacle 1650 can be formed by the housing 1610, formed partially by the housing 1610, be partially defined by the housing 1610, be defined by the housing 1610, or be coupled to the housing 1610, in different embodiments. For example, a bottom 1660 of the receptacle can separate the receptacle 1650 from the interior of the housing 1610. A sensor array 1670 is also included, which can include any of the sensors described herein, for example a camera 1672 and an accelerometer 1674. The sensor array 1670 can also include other sensors 1676, such as one or more additional cameras, an ambient temperature sensor, or a gyroscopic sensor. Sensor array 1670 can also include one or more sensors 1677 to detect consumables in the receptacle 1650, and sensors 1678 to detect temperature and/or grip attributes (e.g., grip intensity, a grip consistency, or grip balance). A communication nexus 1680 including a processor coupled to memory is in communication with the sensor array 1670. The communication nexus 1680 can also be in communication with other systems 1690, such as one or more cloud-based systems, mobile devices, tablets, and/or computers.

In the example in FIG. 16A, a camera 1672 is located in the interior of the housing 1610 facing toward the exterior wall portion 1630. In some cases, the camera is arranged such that the camera 1672 has a field of view though material 1640. In some cases, bottom 1660 is opaque or reflective when viewed from the side facing receptacle 1650, but is translucent or transparent when viewed from the interior of the housing, and camera 1672 can be arranged to have a field of view through the bottom 1660. In some such cases, material 1640 may be omitted. In some cases, the system 1601 can have more than one camera, where a first camera can be arranged such that it has a field of view though material 1640 and/or through bottom 1660, and a second camera can be arranged such that it has a field of view though material 1640 and/or through bottom 1660.

In some cases, the processor can determine a level or amount of tremors in a person using information from the camera 1672 and the accelerometer 1674 when the person holds the housing 1610 by the gripping area 1620. The level or amount of tremors can be qualitative or quantitative. For example, level or amount of tremors can include small, medium and large amount of tremors, levels one through ten of tremors, the number of tremors per unit of time, the severity of tremors, etc. Information from the sensors can be used to determine the level or amount of tremors, for example, using an amplitude of acceleration from the accelerometer, or using an amount or frequency of shaking using images from one or more cameras.

FIG. 16B shows a schematic of an example of a system 1602 for detecting a physiological response, such as a tremor, in a person, in accordance with some embodiments. The system 1602 includes a device with the same or similar components as system 1601 in FIG. 16A, although some elements and labels have been omitted for clarity. System 1602 has a gripping area 1622 in the shape of a handle that extends from the housing 1610, and sensors 1678 to detect grip attributes. Gripping area 1622 may have a shape other than the shape shown in FIG. 16B. For example, gripping area 1622 can be a handle attached to the housing 1610 at only one point rather than two, or can be located closer to the to or the bottom of the housing 1610. System 1602 also has bottom 1662 that is positioned closer to the bottom of the device than bottom 1660, which causes system 1602 to have a deeper receptacle 1650 that encompasses a larger fraction of the device. In some cases, bottom 1660 and/or 1662 can be non-planar, such as have a shape that is concave, parabolic, bowl-shaped, have segregated compartments to allow for different consumables to be separated, or other non-planar shape.

In some cases, the sensor 1678 coupled to the gripping area 1620 of the housing 1610 can measure a temperature or a grip attribute of the person using the device. The processor of communication nexus 1680 can receive information from sensor 1678, and then the processor of communication nexus 1680 can determine a physiological response based on information from the sensor. Additionally, the processor of communication nexus 1680 can determine an emotional state or operational state based on the physiological response, and optionally trigger an action based on the emotional state or operational state. Emotional states or operational states determined using processor of communication nexus 1680 include happiness, sadness, joy, sexual arousal or orgasm, pleasure, sleepiness, meditation, daydreaming, anger, displeasure, annoyance, pain, calmness, relaxedness, attentiveness, distractedness, etc. For example, sensor 1678 can be a load cell or pressure sensor which can determine the intensity of a grip, or the consistency of an intensity of a grip. In another example, sensor 1678 or sensor 1676 (not located in the gripping area 1620) can be a level sensor and information from the level sensor can be used by the processor to determine an amount of balance of a grip. For example, if the level sensor detects large changes in levelness of the device over a period of time indicative of balancing motions (as opposed to shorter time scale motions that may be indicative of a tremor), then the processor can determine an amount of balance of a grip based on that information.

In some examples, gripping area 1620 or 1622 can include one or more heating elements. The processor can control the heating elements based on a determined physiological response and/or emotional state or operational state. For example, the processor can direct the heating elements of gripping area 1620 or 1622 to heat up in response to a sensor detecting that the person is cold (e.g., has a measured temperature below a predetermined threshold, or compared to a saved historical temperature of a person). In another example, the processor can direct the heating elements of gripping area 1620 or 1622 to heat up in response to a sensor detecting that the person is having significant tremors (e.g., at a level above a predetermined threshold, or compared to a saved historical temperature of a person). In some cases, a temperature of the gripping area 1620 or 1622 can be used as a stimulus, and can be changed in order to change an emotional state or operational state of a person.

In some cases, the sensor 1677 coupled to the receptacle 1650 can measure the presence and/or a quantity of a consumable in the receptacle 1650. For example, the sensor 1677 can include one or more of camera(s), thermometer(s), liquid level sensor(s), and/or load cell(s). Signals or information from the sensor 1677 can be used by the processor of the communication nexus 1680 to determine the presence and/or a quantity of a consumable in the consumable receptacle. For example, images from the camera(s) can be analyzed by the processor to determine if a consumable is present in the receptacle 1650. In another example, the presence of a cold consumable (e.g., ice cream, or a cold liquid) could be detected using a temperature sensor. In another example, a load cell (or scale) can be used to detect the mass of a consumable in the receptacle 1650. In another example, a liquid level sensor can include a series of conductive electrodes along the height of receptacle 1650 coupled to the processor, which can determine a liquid level from signals from the electrodes. The processor can trigger an action based on the presence or quantity of a consumable in the receptacle. For example, if sensor 1677 detects that a consumable is finished, it can send an alert to a caregiver.

In some cases, the sensor array 1670 sends sensor signals to the processor of the communication nexus 1680, which uses the information from the sensor array 1670 to determine an amount or level of a tremor in a person holding the housing 1610 of the device by the gripping area 1620. For example, the processor can determine a level or amount of tremors in a person using information from the camera 1672 and the accelerometer 1674 when the person holds the housing 1610 by the gripping area 1620 by performing image analysis of images taken from the camera over time, and using data about the movement of the device from the accelerometer. In some cases, the processor can determine a level or amount of tremors in a person using only information from the camera 1672, or only information from the accelerometer 1674. However, in some cases, the accuracy of determination of the amount or level of tremors in a person is improved using both information from the camera 1672 and information from the accelerometer 1674.

In some cases, the communication nexus 1680 is further in communication with other systems 1690, such as one or more cloud-based systems, mobile devices, tablets, and/or computers. For example, a network processor in the cloud that is coupled to memory in the cloud can be used to run or develop models and/or algorithms to analyze data from the sensors of sensor array 1670. In another example, a history of a person's physiological data or other information can be stored in a memory of a computer or mobile device and the processor of communication nexus 1680 can communicate (e.g., wirelessly) with the computer or mobile device to use the historical data to determine a threshold for a physiological response, emotional state, or operational state. The threshold can then be used to determine whether an action should be taken in response to a determined physiological response, emotional state, or operational state.

In some cases, the communication nexus 1680 is further in communication with other systems 1690 that include other sensors, and information from the other sensors can be used by the processor 1690 to determine the physiological responses and emotional states or operational states of a test subject. The other sensors can include any of the sensors described herein, such as one or more temperature sensors, resistive temperature devices (RTDs) or thermistors, microphones, electrical measurements (e.g., electrical resistance, electric field strength, etc.), ambient air pressure, ambient humidity, piezoelectric microphone (to detect vibrations), photoresistor, camera, a blood pressure cuff, and a retinal oximeter. For example, the other systems 1690 could include a surveillance camera (e.g., at an assisted care facility, or a baby monitor in a home), and the processor of communication nexus 1680 can use the information from the surveillance camera to acquire images of the face of a person and determine their emotional state using facial or eye expressions of the person. In another example, the other systems 1690 can include utensils (e.g., a spoon or fork) used by the person, which can include one or more accelerometers or gyroscopes. In such examples, the processor of communication nexus 1680 can use information from the one or more accelerometers or gyroscopes of the utensils to determine a level of tremors. In some cases, processor of communication nexus 1680 can use information from the sensor array 1670 together with information from the other sensors of the other systems 1690 to determine the physiological responses and emotional states or operational states of a test subject.

In another example, the other systems 1690 in FIG. 16A can include a medical diagnostic device (e.g., a blood pressure cuff) used by the person interacting with system 1601, which can send information to the communication nexus 1680. In such cases, the processor of communication nexus 1680 can use the information from the medical diagnostic device to determine a physiological response of the person, and use the physiological response to determine an emotional state of the person. In some cases, the communication nexus 1680 can control or send commands to the medical diagnostic device (e.g., a blood pressure cuff) based on an emotional state of a person. For example, the communication nexus 1680 can control or send commands to the medical diagnostic device (e.g., a blood pressure cuff) to cause it to wait until a person is in a particular emotional state (e.g., beyond a threshold) before taking diagnostic measurement.

In some cases, the processor of the communication nexus 1680 causes a speaker 1682 of the device to play adaptive music based on a detected physiological response from a person. The processor can change the musical aspects of the music according to a model, such as those developed using recurrent neural networks and deep learning, or an algorithm. The sensor array 1670 can transmit sensor signals to the processor which can determine a measured physiological response of the person from the transmitted sensor signals. The processor can then correlate the physiological response with the musical aspects of the music, and cause the musical aspects of the music to be changed based on the physiological response of the person. Such an adaptive feedback loop can be used to change the emotional state or operational state of the person by changing the musical aspects of the music. For example, the physiological response can be a temperature of the person measured using an IR camera that focuses on and tracks the face, head, or forehead of a person. In another example, the physiological response is a temperature of the person, and the sensor array includes a temperature sensor coupled to the gripping area of the housing.

There are many different types of musical aspects that can be changed by the processor with the goal of changing a physiological response, or emotional state, or operational state of a person. A musical aspect can be the type of instrument in a piece of music, since different types of instruments (e.g., a violin compared to a cello, or a saxophone compared to a clarinet or piano) have different tones, which can evoke different types of responses or states in a person. Another musical aspect that can be changed is the number of instruments, since a single instrument, a string quartet, a jazz band, a rock band, or an entire orchestra can also evoke different types of responses or states in a person. Another musical aspect that can be changed is the key, since it is well known that the key of a piece of music can evoke different types of responses or states in a person. For example, music in a major key (e.g., Three Blind Mice) compared to music in a minor key will tend to evoke different types of responses or states in a person. The major key may evoke a happy or upbeat emotional state. The minor key may evoke a sad or distressed emotional state. For example, music in a sharp key compared to music in a flat key will tend to evoke different types of responses or states in a person. In some cases, a person can be exposed to several pieces of music, or a series of pieces of music, with different musical aspects or attributes, and the physiological response, or emotional state, or operational state of the person can be detected to determine which musical aspects and/or pieces of music evoke responses or states in the person.

System 1602 in FIG. 16B optionally includes a screen 1684, in some embodiments. System 1601 in FIG. 16A can also include a screen in some embodiments. Screen 1684 can be a touchscreen in some cases, and can be used to provide user input. For example, screen 1684 can include a graphical user interface (GUI) for a user to interact with the device, such as to turn the device on or off, set a time or date, change settings, change the volume of music or other audio being played, etc. In some cases, the processor of the communication nexus 1680 causes a screen 1684 of the device to display images based on a detected physiological response from a person. For example, a sensor in receptacle 1650 can monitor the amount of a consumable in receptacle 1650, and change the display based on the amount, such as to display message that asks the person to consume more of the consumable. In some cases, screen 1684 can be used as a stimulus, and can be changed in order to change an emotional state or operational state of a person.

In some embodiments of the systems and methods described herein (e.g., device 10 in FIG. 1, or systems 1601 and 1602 in FIGS. 16A and 16B), a camera is used to image the face of a person. A processor can translate the data from the images to determine one or more physiological responses. For example, an IR camera can detect a temperature map of a face, and the processor can translate that temperature map into a temperature of the person, or a gradient of temperature across the face. The physiological response of temperature or temperature gradient of the person's face can be further processed by the processor to determine other physiological responses, such as the presence of a fever, the presence of poor circulation, or the possibility that the person is having or is about to have a stroke. The processor can use AI models or algorithms to then determine the presence of (or possibility of) an emotional state from one or more of the physiological responses. For example, if a temperature map indicates that the person has a relatively high temperature (e.g. compared to historical data of the person, or a predetermined threshold), then the processor can determine that the person has or is likely to have the emotional state of being uncomfortable due to the ambient temperature of the environment being too warm. In another example, the camera can detect images of the person's eye(s), and the physiological response can be an eye expression determined from the image of the person's eye(s). The processor can then determine a possible emotional state from the eye expression physiological response.

In some embodiments of the systems and methods described herein, information about the person can be used by the processor when determining a physiological response from sensor data and/or when determining an emotional state or operational state from a physiological response. For example, historical data from the person can be input and saved, where the historical data can be data measured by a sensor of the system, or can be input into the system by the person or a caregiver. For example, if a person has had stroke that causes a portion of their face to be paralyzed, then the processor can take that into account when analyzing images of the person's face, for example, can exclude paralyzed regions of the face from the analysis. In another example, a processor can refine AI models using information from the person in a first session, and save the model parameters to be used in subsequent sessions.

In some embodiments, the systems and methods described herein can be used for extended periods of time, or can be left on substantially all of the time. For example, the sensors could be used to monitor one or more physiological responses or emotional states of an elderly person in an assisted living facility, or of a baby in a crib. In some cases, the processor can cause an alert (e.g., an auditory alert or an electronic alert) to be triggered if a detected physiological response exceeds a threshold.

In some embodiments of the systems and methods described herein, a temperature and/or humidity of the ambient environment can be used as a stimulus, and can be changed in order to change an emotional state or operational state of a person. For example, the other system 1690 shown in system 1601 in FIG. 16A can include a space heater for a room, an air conditioning (AC) unit, a fan, or a heating, ventilation, and air conditioning (HVAC) system controlling the ambient temperature of a building or room. A processor of communication nexus 1680 of system 1601 can communicate with these other systems to change the temperature and/or humidity of a room. The physiological response(s), emotional state(s), and/or operational state(s) of a person in the room can be monitored and changed using the temperature and/or humidity of the ambient environment, as described herein.

In some embodiments, the systems and methods described herein account for background noise, or other ambient conditions. For example, if an auditory stimulus (e.g., music) is being played to change an emotional state of a test subject, and the device detects a level of background noise that exceeds a threshold, then the volume of the auditory stimulus can be increased to overcome the background noise. In another example, the ambient temperature of the environment can be taken into account when measuring a temperature of a test subject.

FIG. 17 is a flowchart of an example method 1700 for a computer-implemented method for performing a diagnostic test on a person, in accordance with some embodiments. For example, device 10 in FIG. 1, or systems 1601 and 1602 in FIGS. 16A and 16B could be used to perform method 1700. At block 1710, a processor of the computer causes a speaker (e.g., speaker 1682 of the device shown in FIG. 16A) to play music, where the music has musical aspects. At block 1720, the processor causes the musical aspects of the music to be changed. Optionally, the musical aspects may be changed according to a model, such as those developed using recurrent neural networks and deep learning, or an algorithm. At block 1730, a measured physiological response of the person is received by the processor, and processor correlates the physiological response with the musical aspects of the music. At block 1740, the aspects of the music are changed based on the physiological response of the person, until a threshold physiological response is met or a desired physiological response is achieved. For example, the physiological response could be a temperature, and the threshold physiological response is a temperature below which the person must be in order to meet the threshold. At block 1750, a diagnostic test (e.g., blood pressure) is performed on the person, after the physiological response of the person is at or past the threshold.

FIG. 18 is a flowchart of an example method 1800 for determining and changing a physiological response of a person, in accordance with some embodiments. For example, device 10 in FIG. 1, or systems 1601 and 1602 in FIGS. 16A and 16B could be used to perform method 1800. At block 1810, a device detects the presence of a human. At block 1820, the device focuses on a face of the human. At block 1830, the device measures a temperature gradient across an image area, such as an upper face area or forehead of the human. At block 1840, the device records a first temperature or temperature map and determines a first physiological response from the human. At block 1850, the device records an ambient temperature. At block 1860, the device plays music using a speaker (e.g., speaker 1682 of the device shown in FIG. 16A) of the device. At block 1870, the device modifies a musical aspect of the music, records additional temperature maps, and determines additional physiological responses from the human, until the device observes a measurable differential physiological response from the human.

The following blocks describe an example method for determining and changing a physiological response, emotional state, or operational state of a person. For example, device 10 in FIG. 1, or systems 1601 and 1602 in FIGS. 16A and 16B could be used to perform the blocks of this method.

In a first block, a device is placed on a surface (e.g., table, arm of chair, on a shelf or end table).

In a second block that is optional, several devices can electronically communicate (e.g., via wired or wireless communication networks) to each other. Some devices can be hidden, but give alternate views and scans.

In a third block, the device detects the presence of the person (e.g., a person approaching the surface on which the device is positioned or otherwise in proximity to the device).

In a fourth block, the device, optionally, determines or confirms whether the person is to be measured. For example, the device can map a baseline profile (many sensors are possible) to differentiate this human from others who might interact/block mid-scan. For example, the device may perform a face identification to determine whether the person should be measured.

In a fifth block, the device focuses on the person's face, for example, using a camera, and can optionally alarm and/or send a message if the facial detection zone is no longer in the field of view of the camera.

In a sixth block, the camera may automatically alter a zoom (e.g., focal length) to track a facial area (e.g., head, forehead, face, etc.) from nose up to "forehead," which in some cases can be occluded by a hat or hair.

In a seventh block, the camera can switch to IR or near IR mode.

In an eighth block, the camera captures the human temperature gradient across an image area (e.g., of the facial area).

In a ninth block, the device records this temperature map, for example using a processor of the device coupled to memory and to the camera.

In a tenth block, the device records an ambient temperature, for example, using a temperature sensor of the device coupled to the processor.

In an eleventh block, the device plays tones at a base volume (and optionally also plays a video or a holographic video), or music, using a speaker of the device. In some cases, the device can play video and/or holographic video stimuli in addition to, or instead of, music. In such cases, a separate logic tree or model or algorithm can be used for video and/or holographic video stimuli. Video can be shown on a display that is part of the device, or coupled to the device, for example, on a smartphone or tablet that is in communication with the device. Holographic video can be played using a holographic display, which is a display that can use light diffraction to display a three-dimensional image. For example, the system can determine how to change a video and/or holographic video stimuli using visual, audio, vibration, and/or temperature information from sensors. In some cases, a detected physiological response to music, video, holographic video, or other stimuli can include one or more of tears, tapping, verbal noise, noticeable relaxation, swaying, shivering, or orgasming.

In a twelfth block, the device modifies the volume and/or magnitude of various stimuli (e.g., musical aspects of music, or parameters or binaural tone patterns) until observing a measurable differential response from the person, for example, the human temperature gradient captured by the camera.

In a thirteenth block, a user, a caregiver, a medical professional, or the person selects desired target physiological response, emotional state, or operational state.

In a fourteenth block, the device selects a base music from a database. In some cases, priority to any pre-known music biases can be used, for example, based on personal history, location (use GPS), or culture (e.g., as determined from a camera image). The base music can be relatively slow, mellow, and/or have a low volume.

In a fifteenth block, the device increases the volume of the music or binaural tone pattern.

In a sixteenth block, the device detects a physiological response, emotional state, or operational state of the person.

In a seventeenth block, the device records a second temperature gradient, measured using the camera or a temperature sensor, using the processor.

In an eighteenth block, the device increases a tempo of the music.

In a nineteenth block, the device detects (using one or more sensors) a physiological response (e.g., the temperature gradient), emotional state, or operational state of the person.

In a twentieth block, if a threshold time elapses (e.g., if the operation times out) without detecting a change in the physiological response, emotional state, or operational state of the person, the device may change to another musical aspect of the music or parameter of the binaural tone pattern. For example, a syncopation change could be made, for example, where a piece of music could be switched from a slow quick step beat, to a swing step. For example, a song sample can start in ¾ time like a waltz, and then be changed to 4/4 time with syncopation. Other parallel examples can be found in calypso, rock, and hip-hop music genres.

In a twenty-first block, if a threshold time elapses (e.g., if the operation times out), without detecting a change in the physiological response, emotional state, or operational state of the person, the device may vary other musical aspects, parameters of the binaural tone patterns, or other stimuli. For example, some stimuli could be turned off and others turned on, the location or proximity of sources of stimuli could be changed, or one or more sensors could be moved or adjusted to see if the sensor is at an inadequate angle or proximity.

In a twenty-second block, if a threshold time elapses (e.g., if the operation times out), without detecting a change in the physiological response, emotional state, or operational state of the person, and if the person is holding the device by a gripping area, then the device may vibrate, change the temperature, or generate sound.

In a twenty-third block, the device detects a physiological response (e.g., the temperature gradient), emotional state, or operational state of the person.

In a twenty-third block, once a change in the physiological response, emotional state, or operational state of the person is detected, then the device can look up in database if there is sufficient change (i.e., if a threshold has been met) to expect a useful set of medical variables to be measured using a diagnostic test.

In a twenty-fourth block, the device may measure the person using a diagnostic test, and optionally keep varying stimuli (e.g., musical aspects or parameters of a binaural tone pattern) until the physiological response, emotional state, or operational state of the person exceeds the threshold. Optionally, the device may measure the person using a second diagnostic test. For example, the physiological response and/or the diagnostic test can measure blood parameters, such as blood pressure, and blood oxygen, which can be measured using an oxygen sensor (e.g., at a person's skin or wrist), or using a retinal oximeter.

In a twenty-fifth block, optionally, the device can run a base profile to characterize the person's responses before, during, and/or after each session. A person's profile can change with their medical condition, emotional state, what they ate, medications taken recently, and other data about the person.

FIG. 19 is a flowchart of an example method 1900 for determining and changing a physiological response of a person, in accordance with some embodiments. Systems described herein can be used to perform method 1900, for example the device 10 in FIG. 1, or systems 1601 and 1602 in FIGS. 16A and 16B. At block 1910, a desired target physiological response, or emotional state, or operation state is selected (e.g., by a user, or a caregiver). At block 1915, a base piece of music is selected from a database. The database can include a plurality of pieces of music. Each piece of music can be associated with a physiological response, an emotional state, or operational state, for example using a model (e.g., developed using a recurrent neural network or deep learning) or algorithm. The base piece of music can have a relatively low tempo and a relatively low volume, in some cases. In some cases, the base piece of music can be selected by the person, or a user, or a caregiver. In some cases, the base piece of music can be selected based on a prior selection by the person, as determined using saved information or communicating with another system (e.g., a cloud-based system, or mobile device). At block 1920, the volume of the music is increased. At block 1925, a first physiological response is detected in a person listening to the music, using a device including one or more sensors configured to detect the physiological response. For example, an IR camera can be used to determine a temperature of the person. At block 1930, the physiological response is recorded, for example using memory coupled to a processor of the system (e.g., systems 1601 or 1602 in FIG. 16A or 16B). At block 1935, the tempo of the music is increased. At block 1940, a second physiological response of the person is detected. At block 1945, the first physiological response and the second physiological response are compared using the processor, and if they are significantly the same, then the music is switched to a different piece of music, and a third physiological response of the person is detected. The different pieces of music that are played in method 1900 have at least one musical aspect that differs between them, but other aspects can be the same. For example, at block 1945, the different piece of music could be similar to the base piece of music, but be in a different key. At block 1950, the music is switched and physiological responses of the human are measured until a detected physiological response of the human is different from the first physiological response. At block 1955, the detected physiological response is compared to a threshold of the desired target physiological response, and if the detected physiological response meets or is past the threshold, then determine that a diagnostic test is to be run on the person. In some cases, method 1900 can further include the block of running the diagnostic test on the person.

Figure 20:
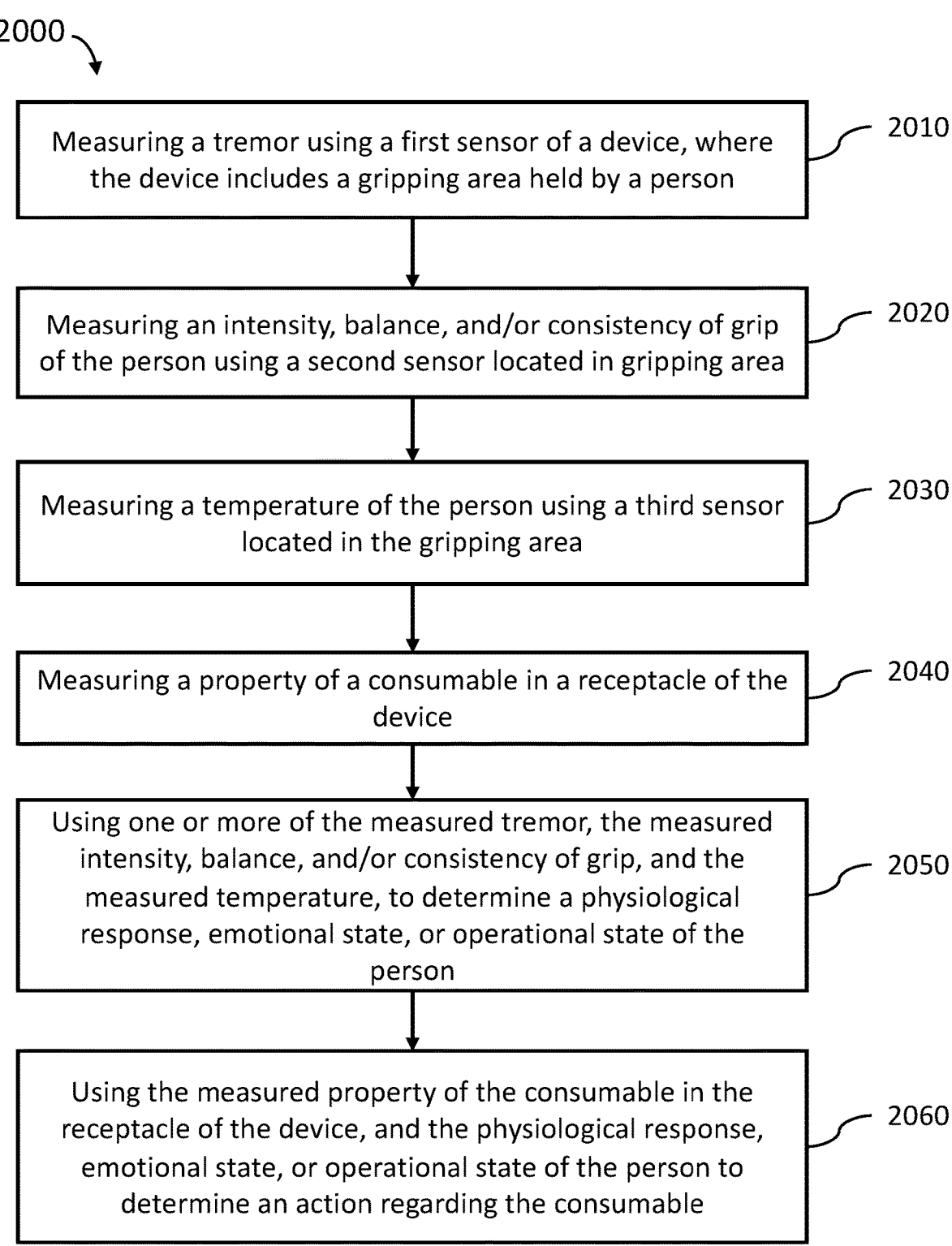
FIG. 20 is a flowchart of an example method for determining a plurality of physiological responses of a person holding a device, in accordance with some embodiments.

FIG. 20 is a flowchart of an example method for determining a plurality of physiological responses of a person holding or interacting with a device, in accordance with some embodiments. At block 2010, a tremor is measured in a person using a first sensor of a device, while the person is holding the device by a gripping area. At block 2020, an intensity, balance, and/or consistency of grip of the person is measured using a second sensor located in the gripping area of the device. At block 2030, a temperature of the person is measured using a third sensor of the device. The temperature sensor can be an IR camera that focuses on the face of the person, or a thermometer located in the gripping area. At block 2040, the presence of or amount of a consumable in a receptacle of the device is measured using a consumables sensor. At block 2050, a processor of the device (or coupled to the device) can use one or more of the measured tremor, the measured intensity, balance, and/or consistency of grip, and the measured temperature, to determine a physiological response, emotional state, or operational state of the person. At block 2060, the processor can use the measured property of the consumable in a receptacle of the device, and the physiological response, emotional state, or operational state of the person to determine an action regarding the consumable. In some cases, the device can also perform the action. For example, the consumable can be magnesium fortified ice cream, and the device can measure how much of the ice cream has been eaten over a period of time (e.g., since the ice cream was detected in the receptacle. In this example, the tremor information, optionally along with the temperature and the intensity, balance, and/or consistency of grip information, from the sensors can be used by the processor of the device to determine if enough magnesium fortified ice cream has been eaten, or if the device should trigger an action regarding the consumable, such as sending or playing an alert than more magnesium fortified ice cream should be eaten by the person. The alert can be an auditory signal, such as a voice asking the person to eat more played by a speaker of the device. The alert can also be an electronic alert, such as a text message or email sent to the person or a caregiver from the device.

The following blocks describe an example method for determining and changing a physiological response, emotional state, or operational state of a person. Each of the blocks can also be functions of the systems and/or devices described herein. For example, device 10 in FIG. 1, or systems 1601 and 1602 in FIGS. 16A and 16B could be used to perform the blocks of this method.

In a first block, a person grips a handle of a mug, where the mug contains a receptacle containing a consumable (e.g., magnesium supplemented ice cream), and sensors for measuring physiological responses of the person.

In a second block, the mug measures the shake or vibration of the mug using one or more sensors of the mug such as a camera and/or an accelerometer.

In a third block, a component (e.g., housing, gripping area, etc.) of the mug measures the person's intensity, balance, and consistency of grip, using sensors of the mug (e.g., a pressure sensor in the handle).

In a fourth block, a component (e.g., housing, gripping area, etc.) of the mug measures the temperature gradient of the grip, using a temperature sensor of the component.

In a fifth block, the mug measures the temperature gradient of the consumable.

In a sixth block, a sensor of the mug (e.g., in a lining of the receptacle) can sample properties of the consumable (e.g., how well the magnesium is mixed with the ice cream).

In a seventh block, a sensor in the mug can sample how much consumable is in the receptacle (e.g., how much is left at the edges of the bowl).

In an eighth block, the mug can optionally vibrate and/or play a message to encourage the person to consume more of the consumable (e.g., to scrape more from the corners).

In a ninth block, the mug can optionally include a stirrer to mix the ingredients, for example, with a special cap and implements, that may be removed before serving. The mug can also optionally measure the mixture and stop the mixing when a homogenous mixing threshold is reached.

In a tenth block, the mug can optionally heat and/or chill a consumable. For example, the device can use a heater (e.g., heating element) or cooling element (e.g., Peltier element) coupled to a battery or a rechargeable battery to heat or cool the consumable within a limited temperature range, and can heat or cool the consumable over a wider temperature range if plugged in to a wall outlet.

In an eleventh block, the mug can optionally include a compartment with an additional consumable (e.g., magnesium) which it can mix in with a consumable in the receptacle. For example, the device could optionally detect a physiological response from person (e.g., an amount of shaking or tremors) and suggest more of a consumable (e.g., magnesium) based on the detected physiological response. In some cases, a caregiver, or the person can add one consumable (e.g., ice cream) and the device can dispense a second consumable (e.g., magnesium) and then mix the first and second consumable in the receptacle. In another example, the mug can optionally dispense flavor packets that can mask the taste of a consumable (e.g., magnesium), to improve the taste of the consumable.

In a twelfth block, the mug optionally has the ability to remember data and create predictive models for a good first approximation for the next visit using the processor, for example using models developed using recurrent neural networks and deep learning.

The following blocks describe a computer-implemented method for performing a diagnostic test on a person.

In a first block, a processor of a device causes music to be played using a speak of the device, where the music includes musical aspects.

In a second block, a processor of the device causes the musical aspects of the music to be changed according to a model or an algorithm.

In a third block, a processor of the device receives information or sensor signals from one or more sensors, uses the received information to determine a physiological response of the person, and associates the physiological response with the musical aspects of the music.

In a fourth block, a processor of the device causes the musical aspects of the music to be changed based on the physiological response of the person, until a threshold or desired physiological response is met.

In a fifth block, a processor of the device causes a diagnostic test to be performed on the person, after the physiological response of the person is at or past the threshold or the desired response is achieved.

In some cases, the physiological response of the above method is a temperature of the person, and the one or more sensors include a temperature sensor or an infrared camera. In some cases, the diagnostic test of the above method is a blood pressure measurement. In some cases, the model of the above method is a model developed using recurrent neural networks and deep learning.

Figure 21:
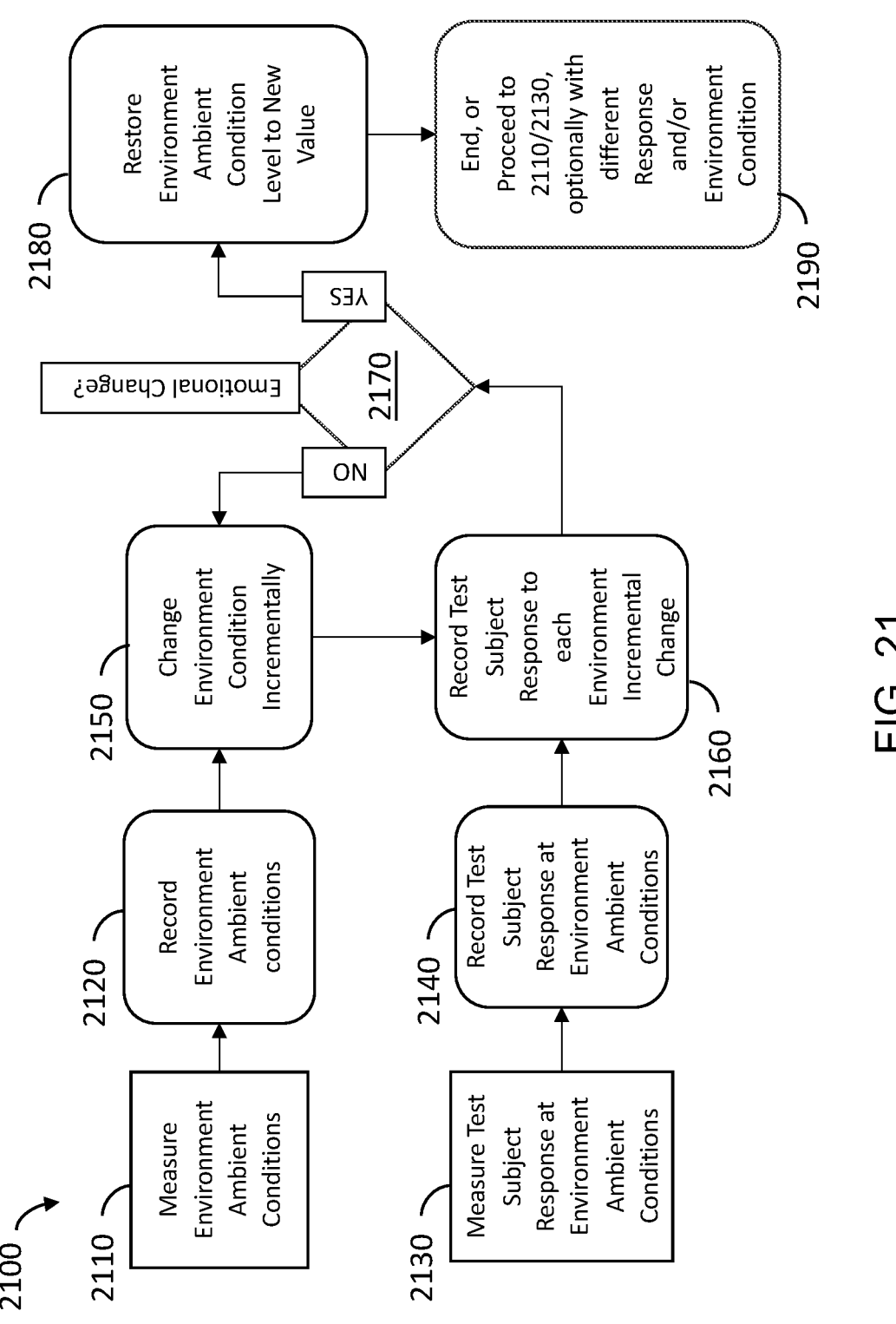
FIG. 21 is a flowchart of an example method 2100 for determining and changing a physiological response, emotional state, or operational state of a person, in accordance with some embodiments.

FIG. 21 is a flowchart of an example method 2100 for determining and changing a physiological response, emotional state, or operational state of a person, in accordance with some embodiments. Each of the blocks of method 2100 can also be functions of the systems and/or devices described herein. For example, device 10 in FIG. 1, or systems 1601 and 1602 in FIGS. 16A and 16B could be used to perform the blocks of this method.

In block 2110, a measurement of ambient conditions of an environment is taken using a sensor array of the system. In block 2120, the measurement of the ambient conditions of the environment is recorded, for example using a processor of the system coupled to memory.

In block 2130, a measurement of a test subject physiological response is taken at the ambient conditions of the environment, using the sensor array of the system. In block 2140, the measurement of the test subject physiological response at the ambient conditions of the environment is recorded, for example using a processor of the system coupled to memory. In some cases, the processor of the system can further determine an emotional state of the person based at least in part on the measurement of the test subject physiological response at the ambient conditions.

In block 2150 an environmental condition is changed incrementally, from the ambient condition level to a new value. In block 2160 measurements of the test subject physiological responses are taken using the sensor array of the system after each incremental change to the environmental conditions. In some cases, the processor of the system can further determine an emotional state of the person based at least in part on the measurement of the test subject physiological responses after each incremental change to the environmental conditions.

For example, the environmental condition can be temperature. In this example, in block 2110 the ambient temperature of the environment is taken and in block 2120 it is recorded. In block 2130 a physiological response (e.g., heart rate, body sweat, facial expression, etc.) of the test subject is determined by the processor using information from the sensor array for the ambient temperature of the environment measured in block 2110. In block 2150, the temperature of the environment can be changed (increased or decreased) incrementally (e.g., in 2-degree increments). In block 2160, the physiological response (e.g., heart rate, body sweat, facial expression, adding/removing/changing clothing, etc.) of the test subject can be determined again by the processor using the new information from the sensor array after each incremental change of the temperature of the environment.

In block 2150, the processor can change the stimulus or environmental condition, taking into account an initial emotional state of the person (determined in block 2130), and additional emotional states of the person (determined in block 2160) determined after each change in the stimulus or environmental condition. In such cases, the processor can determine how to change the stimulus or environmental condition to change the physiological response and/or the emotional state of the person from the current or initial state to a target physiological response and/or emotional state. The target physiological response and/or emotional state can be predetermined or user entered (e.g., by the person or a caregiver). In some cases, the target physiological response and/or emotional state can be determined from the AI model or algorithm based on data from the sensor array. In some cases, the target physiological response and/or emotional state can change based on subsequent data from the sensor array. For example, the processor can determine that a person's initial emotional state is agitated and can determine that the target emotional state is calmness. Subsequently, the processor can determine that the person's emotional state has changed to being distracted, and the processor can automatically update the target emotional state to being attentive. In other words, the AI model or algorithm can include relationships between current or initial physiological responses and/or emotional states and target physiological responses and/or emotional states.

In block 2150, the processor can change the stimulus or environmental condition, taking into account a current physiological response or emotional state of the person (determined in block 2160), and additional physiological responses or emotional states of the person (determined in later iterations of block 2160) after changing the stimulus or environmental condition. If the additional or new emotional state is farther from the target emotional state, then the environmental condition can be set back to the conditions of block 2110 in an attempt to restore the person emotional state to that of block 2130.

In block 2170, the physiological response or emotional state of the test subject determined in block 2130 is compared with the physiological response or emotional state of the test subject determined in block 2160. If a change in physiological response or emotional state of the test subject is detected, then the method proceeds to block 2180. If no change in physiological response or emotional state of the test subject is detected, then the method returns to block 2150 wherein additional incremental changes are made to the environmental conditions until a change in physiological response or emotional state of the test subject is detected in block 2170.

In block 2180, after a change in physiological response or emotional state of the test subject is detected, then the ambient environmental conditions can be changed or restored to the new value introduced in block 2150. In block 2190, the method can end, or can proceed back to blocks 2110 and 2130 where the environmental conditions and the test subject physiological response are measured and correlated to the new environment condition level and the method 2100 can continue. In some cases, a different environment condition can be changed in block 2150, and the change in physiological response or emotional state of the test subject can be detected in response to changing the different environment condition.

Returning to the example of method 2100 from above, the stimulus or the environmental condition being changed is the ambient temperature of a room. In blocks 2110 and 2120, an ambient temperature of the room can be measured and recorded. In blocks 2130 and 2140, a physiological response (e.g., heart rate, body sweat, facial expression, adding/ removing/changing clothing, etc.) of the test subject in the room is determined by the processor using information from the sensor array. In block 2150, the processor can cause the temperature of the environment to be changed incrementally, and in block 2160, the physiological response of the test subject can be determined again by the processor using the new information from the sensor array after each incremental change of the temperature of the environment. In this example, the processor can also determine an initial emotional state of the person in block 2130, and then determine additional emotional states in block 2160 after each change in the temperature of the environment. In such cases, the processor can determine how to change the temperature of the environment to change the person's emotional state from the current or initial state to a new target emotional state.

In another example of method 2100, the stimulus or the environmental condition being changed is ambient sounds in a room. In blocks 2110 and 2120, the ambient sounds of the room can be measured and recorded. In blocks 2130 and 2140, a physiological response (e.g., heart rate, body movement, facial expression, etc.) of the test subject in the room is determined by the processor using information from the sensor array. In block 2150, the processor can cause ambient sounds (e.g., music, tones, etc.) of the room to be changed incrementally using a speaker of a device of the system as described herein. In block 2160, the physiological response of the test subject can be determined again by the processor using the new information from the sensor array after each incremental change of the sounds in the environment. In this example, the processor can also determine an initial emotional state of the person in block 2130, and then determine additional emotional states in block 2160 after each change in the room sounds. In such cases, the processor can determine how to change the room sounds to change the person's emotional state from the current or initial state to a new target emotional state.

In some cases of the above example of method 2100, in block 2150, the processor can change the sounds of the room using a speaker (e.g., in a frequency range from 20 Hz to 20 kHz) using an AI model or algorithm to change a person's initial emotional state to a different or target emotional state. After each of the following iterative changes, the processor can determine the person's physiological response and emotional state in block 2160, and if the method returns to block 2150 after block 2170, then the processor can change the sounds of the room again. In some cases, the AI model or algorithm can determine and store a person's preferences and those preferences can be used in later iterations within a session, or can be saved and used for later sessions (e.g., on a different day). For example, in an iteration of block 2150, the processor can cause the speaker to play 30 seconds of various rhythms (beat only). In some iterations of block 2150, the processor can cause the speaker to play a rhythm starting at about 60 BPM for 30 seconds, the processor can increase the tempo to 120 BPM, and then to 180 BPM. In some iterations of block 2150, the processor can cause the speaker to select the rhythm and/or tempo with the most positive response, where the sound uses tones or pure frequency notes. For example, in the key of C the processor could first cause the speaker to play the primary note, then the dominant note, and then the sub dominant note in sequential order. In an iteration of block 2150, the processor can cause the speaker to shift the key of a sequence of tones up one tone (e.g., from C to D) and play the primary note, then the dominant note, and then the sub dominant in the new key. In some iterations of block 2150, the processor can cause the speaker to play a song or a recognizable simple tune, such as a nursery rhyme. In some cases, the tempo, key, or other attributes of the music can be determined based on the person's preferences as determined from measured physiological response in previous iterations of block 2160. In some cases, the song or tune can be introduced in a major key and played several times in a major key and then changed to a minor key and then repeated.

In another example of method 2100, the stimulus or the environmental condition being changed is ambient humidity and/or pressure in a room. In blocks 2110 and 2120, the ambient humidity and/or pressure of the room can be measured and recorded. In blocks 2130 and 2140, a physiological response (e.g., heart rate, body movement, facial expression, etc.) of the test subject in the room is determined by the processor using information from the sensor array. In block 2150, the processor can cause the ambient humidity and/or pressure of the room to be changed incrementally. In block 2160, the physiological response of the test subject can be determined again by the processor using the new information from the sensor array after each incremental change of the humidity and/or pressure in the environment. In this example, the processor can also determine an initial emotional state of the person in block 2130, and then determine additional emotional states in block 2160 after each change in the room humidity and/or pressure. In such cases, the processor can determine how to change the room humidity and/or pressure to change the person's emotional state from the current or initial state to a new target emotional state.

In another example of method 2100, the stimulus or the environmental condition being changed is haptic vibrations. In blocks 2110 and 2120, the ambient conditions of the room can be measured and recorded. In blocks 2130 and 2140, a physiological response (e.g., heart rate, body movement, facial expression, etc.) of the test subject in the room is determined by the processor using information from the sensor array. In block 2150, the processor can cause the haptic vibrations to be changed incrementally. For example, a person can be holding a device or sitting in a chair that creates haptic vibrations that the person can feel in their hands or body. In block 2160, the physiological response of the test subject can be determined again by the processor using the new information from the sensor array after each incremental change of the haptic vibrations. In this example, the processor can also determine an initial emotional state of the person in block 2130, and then determine additional emotional states in block 2160 after each change in the haptic vibrations. In such cases, the processor can determine how to change the haptic vibrations to change the person's emotional state from the current or initial state to a new target emotional state.

In another example of method 2100, the stimulus or the environmental condition being changed is optical such as the ambient lighting of a room. In blocks 2110 and 2120, the ambient lighting of the room can be measured and recorded. In blocks 2130 and 2140, a physiological response (e.g., heart rate, body movement, facial expression, etc.) of the test subject in the room is determined by the processor using information from the sensor array. In block 2150, the processor can cause the ambient lighting of the room to be changed incrementally. For example, the intensity and/or color of the ambient lighting can be changed, or the amount of natural lighting can be changed. In some cases, the ambient lighting can change intensity in time, for example, to be synchronized to music. In block 2160, the physiological response of the test subject can be determined again by the processor using the new information from the sensor array after each incremental change of the ambient lighting of the room. In this example, the processor can also determine an initial emotional state of the person in block 2130, and then determine additional emotional states in block 2160 after each change in the ambient lighting of the room. In such cases, the processor can determine how to change the ambient lighting of the room to change the person's emotional state from the current or initial state to a new target emotional state.

In another example of method 2100, the stimulus or the environmental condition being changed is an olfactory stimulus. In blocks 2110 and 2120, the ambient conditions of the room can be measured and recorded. In blocks 2130 and 2140, a physiological response (e.g., body movement, facial expression, etc.) of the test subject in the room is determined by the processor using information from the sensor array. In block 2150, the processor can cause the olfactory stimulus to be changed incrementally. In some cases, the processor can cause a small amount of known pleasant and offensive smells (e.g., pastry spray and ammonia) to be introduced into an environment to establish baseline reactions (e.g., facial expressions) for a person. The person's physiological response (e.g., facial expressions) can thereby be used as a detector to determine if an introduced smell is pleasant or offensive to a person. For example, the processor can cause a liquid olfactory stimulus to be sprayed into a room using an automated spraying device, or a volatile substance (e.g., oil, wax, solid, etc.) can be used as the olfactory stimulus and the processor can cause a container to be opened using an actuator such that vapors of the volatile olfactory stimulus can leave the container and enter the room. In block 2160, the physiological response of the test subject can be determined again by the processor using the new information from the sensor array after each incremental change of the olfactory stimulus. In this example, the processor can also determine an initial emotional state of the person in block 2130, and then determine additional emotional states in block 2160 after each change in the olfactory stimulus. In such cases, the processor can determine how to change the olfactory stimulus to change the person's emotional state from the current or initial state to a new target emotional state.

In some cases of method 2100, a processor can perform the steps of method 2100 until a desired a target physiological response or emotional state of the test subject is achieved. For example, a target emotional state of the test subject can be calm or relaxed, and the environmental conditions can be musical aspects of music being played. The processor can perform method 2100 to determine a baseline emotional state in block 2130, change the musical aspects in block 2150, remeasure the person's emotional state in block 2160, determine if there is a change in the emotional state in block 2170, and then continue changing the same musical aspects or different musical aspects in block 2150 until the desired or target emotional state of clam or relaxed is detected.

Unless otherwise expressly stated in the drawings, the sizes, positions, etc., of components, features, elements, etc., as well as any distances therebetween, are not necessarily to scale, and may be disproportionate and/or exaggerated for clarity.

The terminology used herein is for the purpose of describing particular example embodiments only and is not intended to be limiting. As used herein, the singular forms "a," "an" and "the" are intended to include the plural forms as well, unless the context clearly indicates otherwise. It should be recognized that the terms "comprise," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise specified, a range of values, when recited, includes both the upper and lower limits of the range, as well as any sub-ranges therebetween. Unless indicated otherwise, terms such as "first," "second," etc., are only used to distinguish one element from another. For example, one element could be termed a "first element" and similarly, another element could be termed a "second element," or vice versa. The section headings used herein are for organizational purposes only and are not to be construed as limiting the subject matter described.

Unless indicated otherwise, the terms "about," "thereabout," "substantially," etc. mean that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art.

Spatially relative terms, such as "right," 2.9 eft," "below," "beneath," "lower," "above," and "upper," and the like, may be used herein for ease of description to describe one element's or feature's relationship to another element or feature, as illustrated in the drawings. It should be recognized that the spatially relative terms are intended to encompass different orientations in addition to the orientation depicted in the figures. For example, if an object in the figures is turned over, elements described as "below" or "beneath" other elements or features would then be oriented "above" the other elements or features. Thus, the exemplary term "below" can, for example, encompass both an orientation of above and below. An object may be otherwise oriented (e.g., rotated 90 degrees or at other orientations) and the spatially relative descriptors used herein may be interpreted accordingly.

Unless clearly indicated otherwise, all connections and all operative connections may be direct or indirect. Similarly, unless clearly indicated otherwise, all connections and all operative connections may be rigid or non-rigid.

Like numbers refer to like elements throughout. Thus, the same or similar numbers may be described with reference to other drawings even if they are neither mentioned nor described in the corresponding drawing. Also, even elements that are not denoted by reference numbers may be described with reference to other drawings.

Many different forms and embodiments are possible without deviating from the spirit and teachings of this disclosure and so this disclosure should not be construed as limited to the example embodiments set forth herein. Rather, these example embodiments are provided so that this disclosure will be thorough and complete, and will convey the scope of the disclosure to those skilled in the art.

The terms and descriptions used above are set forth by way of illustration and example only and are not meant as limitations. Those skilled in the art will recognize that many variations, enhancements and modifications of the concepts described herein are possible without departing from the underlying principles of the invention. For example, skilled persons will appreciate that the subject matter of any sentence or paragraph can be combined with subject matter of some or all of the other sentences or paragraphs, except where such combinations are mutually exclusive. The scope of the invention should therefore be determined only by the following claims.

The invention claimed is:

1. A system comprising:
a housing comprising a gripping area and an exterior wall portion separating an interior of the housing from an exterior of the housing, wherein the exterior wall portion comprises a material that is opaque or reflective when viewed from the exterior of the housing but is translucent or transparent when viewed from the interior of the housing;
a receptacle at least partially defined by the housing, the receptacle comprising a bottom configured to separate the receptacle from the interior of the housing;
a sensor array, comprising a camera and an accelerometer, wherein the camera is located in the interior of the housing facing toward the exterior wall portion; and
a communication nexus in communication with the sensor array comprising a processor coupled to memory;
wherein the processor is configured to detect a tremor in a person using information from the camera and the accelerometer when the person holds the housing by the gripping area.

2. The system of claim 1, wherein the sensor array further comprises a consumables sensor coupled to the receptacle, wherein the processor is further configured to receive information from the consumables sensor and to use the information to determine if a consumable is present in the receptacle, or a quantity of a consumable in the receptacle.

3. The system of claim 2, wherein the consumables sensor comprises one or more of: a liquid level sensor, a load cell, a temperature sensor, or a camera.

4. The system of claim 1, wherein the sensor array further comprises a load cell or pressure sensor located in the gripping area of the housing configured to measure one or more of a grip intensity, a grip consistency, or a balance of a grip of the person when the person holds the housing by the gripping area.

5. The system of claim 1, wherein the sensor array further comprises sensors configured to detect, in a person, at least one of: heart rate, pupil diameter, facial expression, tearing up, swaying to music.

6. The system of claim 1, wherein the processor is further configured to receive a detected amount or level of tremor in the person using information from the camera and the accelerometer when the person holds the housing by the gripping area.

7. The system of claim 1, wherein the communication nexus is further in communication with a network processor in a cloud that is coupled to memory in the cloud.

8. The system of claim 1, wherein the gripping area comprises a handle that extends from the housing.

9. The system of claim 1, wherein the gripping area comprises one or more textured pads that are substantially flush with the housing.

10. The system of claim 1, wherein the housing comprises a shape of a cup, a mug, or a bowl.

11. The system of claim 1, further comprising a speaker configured to play music or to communicate audibly.

12. The system of claim 11, wherein the processor is further configured to cause the speaker to audibly communicate information about the tremor using the speaker.

13. The system of claim 11, wherein the processor is further configured to:
cause the speaker to play music, wherein the music comprises musical aspects;

cause the musical aspects of the music to be changed according to an algorithm, or according to a model developed using recurrent neural networks or deep learning;

determine a physiological response of the person using information from the sensor array and correlate the physiological response with the musical aspects of the music; and cause the musical aspects of the music to be changed based on the physiological response of the person.

14. The system of claim 13, wherein the physiological response is a temperature of the person, and the sensor array comprises an infrared camera configured to measure the temperature of the person.

15. The system of claim 13, wherein the physiological response is a temperature of the person, and the sensor array comprises a temperature sensor coupled to the gripping area of the housing.

16. The system of claim 13, wherein the processor is further configured to cause the speaker to play an audible alert or voice, based on the physiological response being greater than a threshold.

17. The system of claim 16, wherein the processor is further configured to cause the communication nexus to send an electronic alert, text, or email to the person or a caregiver of the person, based on the physiological response being greater than a threshold.

18. The system of claim 13, wherein the musical aspects include one or more of: volume, tempo, pitch, key, instrumentation, song, lyrics.

19. The system of claim 13, wherein the processor is further configured to determine a first emotional state of the person using the physiological response, and to cause the musical aspects of the music to be changed based on the first emotional state of the person.

20. The system of claim 19, wherein the processor is further configured to cause the musical aspects of the music to change until the processor determines that the first emotional state of the person changes into a second emotional state that is different from the first emotional state, wherein the processor determining that the emotional state of the person has changed into the second emotional state comprises the processor determining a second physiological response of the person using second information from the sensor array and the processor determining a second emotional state of the person using the second physiological response.

* * * * *